(12) United States Patent
Touze et al.

(10) Patent No.: US 12,365,721 B2
(45) Date of Patent: Jul. 22, 2025

(54) ANTIBODY TARGETING THE VP-1 PROTEIN, FRAGMENTS THEREOF, AND USES OF SAME FOR DETECTING INFECTION WITH THE BK POLYOMAVIRUS

(71) Applicants: UNIVERSITÉ DE TOURS, Tours (FR); UNIVERSITE DE PICARDIE JULES VERNE, Amiens (FR); CENTRE HOSPITALIER UNIVERSITAIRE AMIENS-PICARDIE, Amiens (FR)

(72) Inventors: Antoine Touze, Montbazon (FR); Pauline Gaboriaud, Esvres-sur-Indre (FR); Etienne Brochot, Amiens (FR)

(73) Assignees: UNIVERSITÉ DE TOURS, Tours (FR); UNIVERSITE DE PICARDIE JULES VERNE, Amiens (FR); CENTRE HOSPITALIER UNIVERSITAIRE AMIENS-PICARDIE, Amiens (FR)

( * ) Notice: Subject to any disclaimer, the term of this patent is extended or adjusted under 35 U.S.C. 154(b) by 888 days.

(21) Appl. No.: 17/616,391

(22) PCT Filed: Jun. 2, 2020

(86) PCT No.: PCT/EP2020/065213
§ 371 (c)(1),
(2) Date: Dec. 3, 2021

(87) PCT Pub. No.: WO2020/245113
PCT Pub. Date: Dec. 10, 2020

(65) Prior Publication Data
US 2022/0396612 A1    Dec. 15, 2022

(30) Foreign Application Priority Data

Jun. 3, 2019   (FR) ...................... 1905881

(51) Int. Cl.
C07K 16/08   (2006.01)
A61K 39/395   (2006.01)
A61K 39/42   (2006.01)
G01N 33/569   (2006.01)

(52) U.S. Cl.
CPC .......... *C07K 16/084* (2013.01); *A61K 39/395* (2013.01); *A61K 39/42* (2013.01); *G01N 33/56983* (2013.01); *C07K 2317/76* (2013.01); *G01N 2333/025* (2013.01); *G01N 2469/10* (2013.01); *G01N 2800/26* (2013.01)

(58) Field of Classification Search
CPC .... A61K 39/42; A61K 39/395; C07K 16/084; G01N 33/56983; G01N 33/569
See application file for complete search history.

(56) References Cited

PUBLICATIONS

Randhawa et al., J. Gen. Virol., 2009, vol. 90(Pt 3):634-639.*
French Search Report issued on Mar. 19, 2020 in corresponding French Application No. 1905881; 4 pages.
International Search Report (with English translation) and Written Opinion (with Machine translation) issued on Aug. 6, 2020 in corresponding International Application No. PCT/EP2020/065213, 16 pages.
Campanella et al., "MatGAT: An application that generates similarity/identity matrices using protein or DNA sequences"; BMC Bioinformatics; 2003; vol. 4, No. 1, pp. 1-4.
Randhawa et al., "Identification of species-specific and cross-reactive epitopes in human polyomavirus capsids using monoclonal antibodies"; Journal of General Virology; 2009; pp. 634-639.
Viscidi et al., "Serological Cross-Reactivities between Antibodies to Simian Virus 40, BK Virus, and JC Virus Assessed by Virus-Like-Particle-Based Enzyme Immunoassays"; Clinical and Vaccine Immunology; 2003; vol. 10, No. 2, pp. 1-20.
Pastrana et al., "Neutralization serotyping of BK polyomavirus infection in kidney transplant recipients"; PLoS pathogens; 2012; vol. 8, No. 4; pp. 1-11.
Kardas et al., "Optimizing JC and BK polyomavirus IgG testing for seroepidemiology and patient counseling."; Journal of Clinical Virology; 2015; pp. 28-33.
Zhong et al., "Distribution patterns of BK polyomavirus (BKV) subtypes and subgroups in American, European and Asian populations suggest co-migration of BKV and the human race."; Journal of General Virology; 2009; vol. 90, No. 1; pp. 144-152.
Carter et al., "Lack of serologic evidence for prevalent simian virus 40 infection in humans."; Journal of the National Cancer Institute; 2003; vol. 90, No. 20; pp. 1522-1530.
Gardner, et al. "New human papovavirus (BK) isolated from urine after renal transplantation."; The Lancet; 1971; pp. 1253-1257.
Pastrana, et al. "Neutralization serotyping of BK polyomavirus infection in kidney transplant recipients."; PLoS; 2012 pathogens; vol. 8, No. 4; pp. 1-11.
Touzé, et al. "Gene transfer using human polyomavirus BK virus-like particles expressed in insect cells."; Journal of General Virology; 2001; vol. 82, No. 12; pp. 3005-3009.
Prod'hom et al., "Diagnosis of diseases infectious: place of "point of care tests" (POCT)"; Rev Med Suisse; 2008; 13 pages with machine translation.

* cited by examiner

*Primary Examiner* — Xiaozhen Xie
(74) *Attorney, Agent, or Firm* — Maier & Maier, PLLC

(57) ABSTRACT

The invention relates to a new monoclonal antibody targeting the VP-1 protein of the capsid of the BK polyomavirus, fragments thereof, and uses of same for detecting infection with the BK polyomavirus. The monoclonal antibody is capable of recognizing at least all serotypes Ia, Ib2, II, III and IV of the VP-1 protein of the BK polyomavirus.

16 Claims, 10 Drawing Sheets
Specification includes a Sequence Listing.

```
Ib    1   EVLEVKTGVD AITEVECFLN PEMGDPNENL RGFSLKLSAE NDFSSDSPER
II    1   EVLEVKTGVD AITEVECFLN PEMGDPDDNL RGYSLKLTAE NAFDSDSPDK
III   1   EVLEVKTGVD AITEVECFLN PEMGDPDDHL RGYSQHLTAE NAFESDSPDK
IV    1   EVLEVKTGLD AITEVECFLN PEMGDPDNDL RGYSLRLTAE TAFESDSPDR

Ib   51   KMLPCYSTAR IPLPNLNEDL TCGNLLMWEA VTVQTEVIGI TSMLNLHAGS
II   51   KMLPCYSTAR IPLPNLNEDL TCGNLLMWEA VTVKTEVIGI TSMLNLHAGS
III  51   KMLPCYSTAR IPLPNLNEDL TCGNLLMWEA VTVKTEVIGI TSMLNLHAGS
IV   51   KMLPCYSTAR IPLPNLNEDL TCGSLLMWEA VTVKTEVIGI TSMLNLHAGS

Ib  101   QKVHEGGGK  PIQGSNFHFF AVGGDPLEMQ GVLMNYRTKY PEGTITPKNP
II  101   QKVHEGGGK  PVQGSNFHFF AVGGDPLEMQ GVLMNYRTKY PQGTITPKNP
III 101   QKVHEGGGK  PVQGSNFHFF AVGGDPLEMQ GVLMNYRTKY PQGTITPKNP
IV  101   QKVHEGGGK  PIQGSNFHFF AVGGDPLEMQ GVLMNYRTKY PEGTVTPKNP

Ib  151   TAQSQVMNTD HKAYLDKNNA YPVECWIPDP SRNENTRYFG TFTGGENVPP
II  151   TAQSQVMNTD HKAYLDKNNA YPVECWIPDP SRNENTRYFG TYTGGENVPP
III 151   TAQSQVMNTD HKAYLDKNNA YPVECWIPDP SKNENTRYFG TYTGGENVPP
IV  151   TAQSQVMNTD HKAYLDKNNA YPVECWIPDP SRNENTRYFG TYTGGENVPP

Ib  201   VLHVTNTATT VLLDEQGVGP LCKADSLYVS AADICGLFTN SGTQQWRGL
II  201   VLHVTNTATT VLLDEQGVGP LCKADSLYVS AADICGLFTN SGTQQWRGL
III 201   VLHVTNTATT VLLDEQGVGP LCKADSLYVS AADICGLFTN SGTQQWRGL
IV  201   VLHVTNTATT VLLDEQGVGP LCKADSLYVS AADICGLFTN SGTQQWRGL

Ib  251   ARYFKIRLRK RSVKN
II  251   ARYFKIRLRK RSVKN
III 251   ARYFKIRLRK RSVKN
IV  251   PRYFKIRLRK RSVKN
```

EPITOPE RESIDUE

Very highly probable

Highly probable

Probable

*Possible*

FIGURE 8

```
Ib    1  EVLEVKTGVD AITEVECFLN PEMGDPNENL RGFSLKLSAE NDFSSDSPER
II    1  EVLEVKTGVD AITEVECFLN PEMGDPDDNL RGYSLKLTAE NAFDSDSPDK
III   1  EVLEVKTGVD AITEVECFLN PEMGDPDDHL RGYSQHLTAE NAFESDSPDK
IV    1  EVLEVKTGLD AITEVECFLN PEMGDPDNDL RGYSLRLTAE TAFESDSPDR

Ib   51  KMLPCYSTAR IPLPNLNEDL TCGNLLMWEA VTVQTEVIGI TSMLNLHAGS
II   51  KMLPCYSTAR IPLPNLNEDL TCGNLLMWEA VTVKTEVIGI TSMLNLHAGS
III  51  KMLPCYSTAR IPLPNLNEDL TCGNLLMWEA VTVKTEVIGI TSMLNLHAGS
IV   51  KMLPCYSTAR IPLPNLNEDL TCGSLLMWEA VTVKTEVIGI TSMLNLHAGS

Ib  101  QKVHEIGGGK PIQGSNFHFF AVGGDPLEMQ GVLMNYRTKY PEGTITPKNP
II  101  QKVHENGGGK PVQGSNFHFF AVGGDPLEMQ GVLMNYRTKY PQGTITPKNP
III 101  QKVHENGGGK PVQGSNFHFF AVGGDPLEMQ GVLMNYRTKY PQGTITPKNP
IV  101  QKVHENGGGK PIQGSNFHFF AVGGDPLEMQ GVLMNYRTKY PEGTVTPKNP

Ib  151  TAQSQVMNTD HKAYLDKNNA YPVECWIPDP SRNENTRYFG TFTGGENVPP
II  151  TAQSQVMNTD HKAYLDKNNA YPVECWIPDP SRNENTRYFG TYTGGENVPP
III 151  TAQSQVMNTD HKAYLDKNNA YPVECWIPDP SKNENTRYFG TYTGGENVPP
IV  151  TAQSQVMNTD HKAYLDKNNA YPVECWIPDP SRNENTRYFG TYTGGENVPP

Ib  201  VLHVTNTATT VLLDEQGVGP LCKADSLYVS AADICGLFTN SSGTQQWRGL
II  201  VLHVTNTATT VLLDEQGVGP LCKADSLYVS AADICGLFTN SSGTQQWRGL
III 201  VLHVTNTATT VLLDEQGVGP LCKADSLYVS AADICGLFTN SSGTQQWRGL
IV  201  VLHVTNTATT VLLDEQGVGP LCKADSLYVS AADICGLFTN SSGTQQWRGL

Ib  251  ARYFKIRLRK RSVKN
II  251  ARYFKIRLRK RSVKN
III 251  ARYFKIRLRK RSVKN
IV  251  PRYFKIRLRK RSVKN
```

EPITOPE RESIDUE

Very highly probable

Highly probable

Probable

*Possible*

FIGURE 9

```
Ib    1   EVLEVKTGVD AITEVECFLN PEMGDPNSNL RGFSLKLSAE NDFSSDSPER
II    1   EVLEVKTGVD AITEVECFLN PEMGDPDNL  RGYSLKLTAE NAFDSDSPDR
III   1   EVLEVKTGVD AITEVECFLN PEMGDPDHL  RGYSQHLTAE NAFESDSPDR
IV    1   EVLEVKTGLD AITEVECFLN PEMGDPDDL  RGYSLRLTAE TAFESDSPDR

Ib   51   KMLPCYSTAR RLPNLNEDL TCGNLLMWEA VTVQTEVIGI TSMLNLHAGS
II   51   KMLPCYSTAR RLPNLNEDL TCGNLLMWEA VTVKTEVIGI TSMLNLHAGS
III  51   KMLPCYSTAR RLPNLNEDL TCGNLLMWEA VTVKTEVIGI TSMLNLHAGS
IV   51   KMLPCYSTAR RLPNLNEDL TCGSLLMWEA VTVKTEVIGI TSMLNLHAGS

Ib  101   QKVHEHGGGK PIQGSNFHFF AVGGDPLEMQ GVLMNYRTKY PEGTITPKNP
II  101   QKVHENGGGK PVQGSNFHFF AVGGDPLEMQ GVLMNYRTKY PQGTITPKNP
III 101   QKVHENGGGK PVQGSNFHFF AVGGDPLEMQ GVLMNYRTKY PQGTITPKNP
IV  101   QKVHENGGGK PIQGSNFHFF AVGGDPLEMQ GVLMNYRTKY PEGTVTPKNP

Ib  151   TAQSQVMNTL HKAYLDKNNA YPVECWIPDP SRNENTRYFG TFTGGENVPP
II  151   TAQSQVMNTL HKAYLDKNNA YPVECWIPDP SRNENTRYFG TYTGGENVPP
III 151   TAQSQVMNTL HKAYLDKNNA YPVECWIPDP SKNENTRYFG TYTGGENVPP
IV  151   TAQSQVMNTL HKAYLDKNNA YPVECWIPDP SRNENTRYFG TYTGGENVPP

Ib  201   VLHVTNTATT VLLDEQGVGP LCKADSLYVS AADICGLFTN SSGTQQWRGL
II  201   VLHVTNTATT VLLDEQGVGP LCKADSLYVS AADICGLFTN SSGTQQWRGL
III 201   VLHVTNTATT VLLDEQGVGP LCKADSLYVS AADICGLFTN SSGTQQWRGL
IV  201   VLHVTNTATT VLLDEQGVGP LCKADSLYVS AADICGLFTN SSGTQQWRGL

Ib  251   ARYFKIRLRK RSVKN
II  251   ARYFKIRLRK RSVKN
III 251   ARYFKIRLRK RSVKN
IV  251   PRYFKIRLRK RSVKN
```

EPITOPE RESIDUE

Very highly probable

Highly probable

Probable

*Possible*

FIGURE 10

```
Ib    1   EVLEVKTGVD  AITEVECFLN  PEMGDPNENL  RGFSLKLSAE  NDFSSDSPER
II    1   EVLEVKTGVD  AITEVECFLN  PEMGDPDDNL  RGYSLKLTAE  NAFDSDSPDK
III   1   EVLEVKTGVD  AITEVECFLN  PEMGDPDDHL  RGYSQHLTAE  NAFESDSPDK
IV    1   EVLEVKTGLD  AITEVECFLN  PEMGDPDNDL  RGYSLRLTAE  TAFESDSPDR

Ib    51  KMLPCYSTAR  IPLPNLNEDL  TCGNLLMWEA  VTVQTEVIGI  TSMLNLHAGS
II    51  KMLPCYSTAR  IPLPNLNEDL  TCGNLLMWEA  VTVKTEVIGI  TSMLNLHAGS
III   51  KMLPCYSTAR  IPLPNLNEDL  TCGNLLMWEA  VTVKTEVIGI  TSMLNLHAGS
IV    51  KMLPCYSTAR  IPLPNLNEDL  TCGSLLMWEA  VTVKTEVIGI  TSMLNLHAGS

Ib    101 QKVHEHGGGK  PIQGSNFHFF  AVGGDPLEMQ  GVLMNYRTKY  PEGTITPKNP
II    101 QKVHENGGGK  PVQGSNFHFF  AVGGDPLEMQ  GVLMNYRTKY  PQGTITPKNP
III   101 QKVHENGGGK  PVQGSNFHFF  AVGGDPLEMQ  GVLMNYRTKY  PQGTITPKNP
IV    101 QKVHENGGGK  PIQGSNFHFF  AVGGDPLEMQ  GVLMNYRTKY  PEGTVTPKNP

Ib    151 TAQSQVMNID  HKAYLDKNNA  YPVECWIPDP  SKNENTRYFG  TFTGGENVPP
II    151 TASSQVMNID  HKAYLDKNNA  YPVECWIPDP  SKNENTRYFG  TYTGGENVPP
III   151 TAQSQVMNID  HKAYLDKNNA  YPVECWIPDP  SKNENTRYFG  TYTGGENVPP
IV    151 TAQSQVMNID  HKAYLDKNNA  YPVECWIPDP  SKNENTRYFG  TYTGGENVPP

Ib    201 VLHVTNTATT  VLLDEQGVGP  LCKADSLYVS  AADICGLFTN  SSGTQQWRGL
II    201 VLHVTNTATT  VLLDEQGVGP  LCKADSLYVS  AADICGLFTN  SSGTQQWRGL
III   201 VLHVTNTATT  VLLDEQGVGP  LCKADSLYVS  AADICGLFTN  SSGTQQWRGL
IV    201 VLHVTNTATT  VLLDEQGVGP  LCKADSLYVS  AADICGLFTN  SSGTQQWRGL

Ib    251 ARYFKIRLRK  RSVKN
II    251 ARYFKIRLRK  RSVKN
III   251 ARYFKIRLRK  RSVKN
IV    251 PRYFKIRLRK  RSVKN
```

EPITOPE RESIDUE

Very highly probable

Highly probable

Probable

*Possible*

FIGURE 11

ANTIBODY TARGETING THE VP-1 PROTEIN, FRAGMENTS THEREOF, AND USES OF SAME FOR DETECTING INFECTION WITH THE BK POLYOMAVIRUS

FIELD

The invention relates to a new antibody targeting the VP-1 protein, fragments thereof, and uses of same for detecting infection with the BK polyomavirus.

BACKGROUND

The BK virus (BKPyV or BKV) is a Polyomaviridae, which was the first human polyomavirus discovered in 1971 (Gardner et al., Lancet 1971 1:1253-1527). Polyomaviruses are naked viruses with double-stranded circular DNA and have a capsid with an icosahedral symmetry T=7 with a size of 40-45 nm.

The BK virus genome is a circular double-stranded DNA of about 5 kbp and contains three main regions: the early coding region, the late coding region and a non-coding control region. The early coding region codes for the three regulatory proteins (large T antigen (TAg), small T antigen (tAg) and truncated T antigen (truncTAg)), which are the first viral proteins expressed in a newly infected cell and are responsible for initiating viral DNA replication and creating a favourable cellular environment. The late coding region encodes the three structural proteins (VP-1, VP-2 and VP-3) which make up the viral capsid, as well as the agnoprotein, whose role during viral replication is less well defined. The non-coding control region contains the origin of replication as well as the early and late promoters that determine the expression of viral genes.

The BK virus, whose worldwide seroprevalence is around 80% in the adult population, is a ubiquitous virus. After a primary infection, generally during childhood, the virus remains latent for life in the urinary tract (bladder and kidneys). Transmission is probably by aerodigestion, but also by transplacental route or blood transfusion. After infection, the BK virus diffuses via the bloodstream and remains latent for several years in the renal epithelium. Different genotypes of the BK virus exist with varying prevalences worldwide. The most frequent genotypes are genotype I (80%), genotype IV (15%) and genotypes II and III (5%). Each of these genotypes also corresponds to a serotype.

Generally asymptomatic in immunocompetent individuals, the pathogenicity of the BK virus is mainly expressed in a context of immunosuppression, and in particular in kidney transplanted patients in whom the virus can reactivate (approximately 85,000 transplants per year in the world). In order to avoid transplant rejection, immunosuppressive treatments are prescribed to the transplant recipient. Immunosuppression protocols are increasingly powerful (Tracolimus, Mycophenolate mofetil, etc.) and have led to a decrease in the rate of acute rejection. Thus, during the first two years post-transplant, between 30 and 40% of kidney transplant patients will show BK virus replication, which will result in the presence of the virus in the urine (i.e. viruria). The replication of the virus will then intensify, particularly in the cells of the tubular epithelium and induce lesions in this epithelium leading to the passage of the virus into the blood compartment (i.e. viremia) in 15 to 20% of kidney transplant patients. At this stage, the risk is the evolution towards a tubulo-interstitial nephropathy whose incidence at 5 years is 6-7% and which can lead to the loss of the renal graft (up to 5% of transplanted patients) and therefore a return to dialysis for the transplanted patient.

As BK virus infection is partly linked to excessive immunosuppression and in the absence of effective antiviral treatment, the only option for effectively combating viral reactivation is to reduce the doses of immunosuppressive treatment with significant risks of graft rejection in the short term and the appearance of antibodies against the graft in the medium term.

As viral reactivation is generally silent until the first symptoms appear, it is essential to make a regular diagnosis of transplant patients in order to detect the reactivation of the BK virus as early as possible and to manage the infection by modulating the immunosuppressive treatment. In view of the frequency and potential severity of BK virus infection, all the players in the medical community agree on the need for early detection of infection and replication of the BK virus in all kidney transplant patients. This screening is recommended during the 5 years after transplantation and the recommendations of the learned societies specify that screening must be carried out at least every 3 months for the first two years and then at least once a year for the following three years.

Although there are antibodies targeting the BK virus, particularly therapeutic ones, these have the disadvantage of either not interacting with all serotypes or crossing with the JC virus, a polyomavirus close to the BK virus. Therefore, for the detection of infection, the only specific solution available is the quantification of the BK virus by the PCR technique. This quantitative and reliable technique is used to monitor many viral infections. However, it is not ideal and efficient in the context of screening for reactivation of the BK virus. Indeed, the PCR technique is not appropriate at two levels:

(1) At the level of the patient and his post-transplant follow-up: Viral quantification by PCR can only be carried out in a transplant hospital center, which generates significant constraints. The patient will have to travel to the hospital center which does not favour a regular diagnosis and the intervention of the nephrologist following detection of the virus by the analysis laboratory will only take place after a certain delay, requiring a new visit of the patient to the transplant center. These constraints partly explain why the infection is only detected at an advanced stage of the viral pathology.

(2) At the level of the analysis laboratory (hospital virology department): the PCR method is costly (without taking into account the cost of human resources) and requires dedicated infrastructures available only within the transplant hospital. Moreover, results are not immediately available because of (i) the need to carry out the tests in series in order to limit the cost of controls and (ii) the delay between sampling and the transmission of results to clinicians, which can take several days.

Consequently and due to these constraints, only a quarterly monitoring of the reactivation of the BK is set up, which is insufficient, whereas a quicker detection would allow a better follow-up.

SUMMARY

In this context of a search for suitable and effective diagnostic tools to make up for the current lack, a first aim of the invention is to propose an antibody targeting the VP-1 protein of the BK virus capsid. A second aim of the invention is to propose fragments of this antibody. A third aim of the invention is to provide the tools (nucleic acid, vector, etc.) enabling the production of the said antibody and/or its fragments. Last, another aim of the invention is to offer diagnostic methods for easily and rapidly detecting BK virus replication, as well as the kits enabling them to be used.

BRIEF DESCRIPTION OF FIGURES

The following figures will better illustrate the invention, without limiting its scope.

FIGS. 8 to 11 show the residues (amino acids) that are predicted to belong to the epitope of VP-1 proteins serotypes I, II, III and IV recognised by antibodies 'F6' (FIG. 8), 'H6' (FIG. 9), '9B1' (FIG. 10) and '14D6' (FIG. 11).

DETAILED DESCRIPTION

Figure 1:
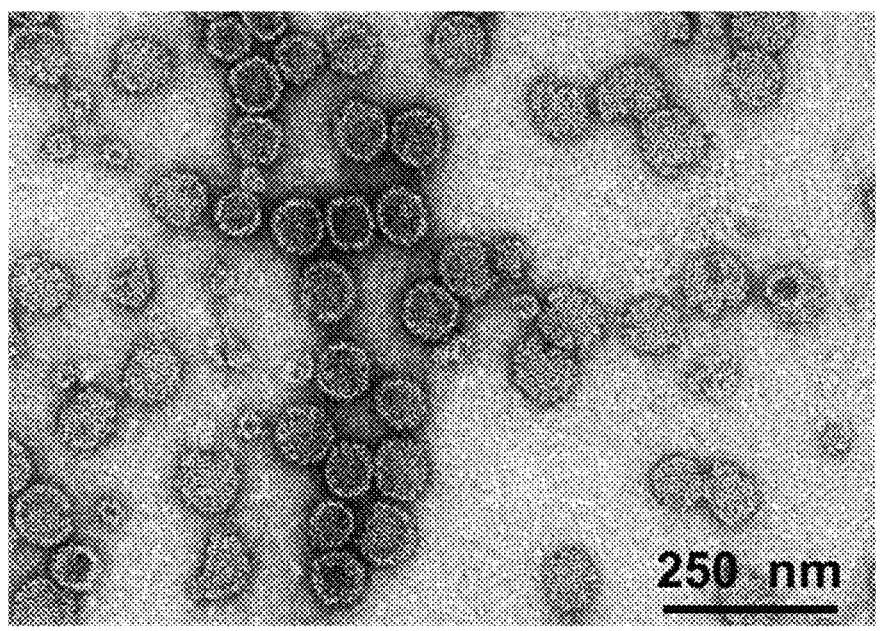
FIG. 1 is an electron micrograph of virus-like particles (VLPs) obtained by expression of the BKPyV VP-1 serotype Ib2 gene in insect cells. The preparation was negatively stained with 5% uranyl acetate and observed at a nominal magnification of ×50,000 with a JEOL 1010 electron microscope.
Bar: 250 nm.

The present invention relates to the subject matter as defined below and as described below. In addition, and unless otherwise specified or the context otherwise requires, all terms shall have their ordinary meaning in the relevant field(s).

According to a first aspect of the invention, it concerns a monoclonal antibody directed against the VP-1 protein of the capsid of the BK virus, said VP-1 viral protein being represented by a sequence having at least 90%, in particular 93%, identity with the sequence SEQ ID NO: 4, said monoclonal antibody being capable of recognizing at least all serotypes Ia, Ib2, II, III and IV of said VP-1 protein of said BK virus, and
said monoclonal antibody not being capable of recognizing the JC virus.

In the invention, the term "antibody" refers to an immunoglobulin, a multimeric protein consisting of 4 chains participating in the acquired immune response.

Immunoglobulins are well known to the man skilled in the art and are made up of an assembly of two dimers, each consisting of a heavy chain and a light chain. The multimeric complex is assembled by linking a light chain and a heavy chain by a disulphide bridge between two cysteines, the two heavy chains being themselves also linked by two disulphide bridges.

Each of the heavy and light chains consists of a constant region and a variable region. The assembly of the chains that make up an antibody defines a characteristic three-dimensional Y-shaped structure, where
the base of the Y corresponds to the constant region Fc which is recognised by the complement and Fc receptors, and
The ends of the Y-arms correspond to the respective assembly of the variable regions of the light and variable regions of the heavy chain.

More precisely, each light chain is made up of a variable region ($V_L$) and a constant region ($C_L$). Each heavy chain consists of a variable region ($V_H$) and a constant region consisting of three constant domains $C_H1$, $C_H2$ and $C_H3$. The $C_H2$ and $C_H3$ domains make up the Fc domain.

The variable region of the light chain consists of three regions determining recognition of the antigen (CDRs) surrounded by four framework domains. The variable region of the heavy chain also consists of three regions determining recognition of the antigen (CDRs) surrounded by four framework domains. The three-dimensional folding of these variable regions is such that the 6 CDRs are exposed on the same side of the protein and allow the formation of a specific structure recognizing a given antigen.

The antibodies described in the invention are isolated and purified, may belong to any isotype/class (e.g. IgG, IgE, IgM, IgD, IgA and IgY) or subclass (e.g. IgG1, IgG2, IgG3, IgG4, IgA1 and IgA2) and are different from natural antibodies. These antibodies are mature, i.e. they have an ad hoc three-dimensional structure enabling them to recognize the antigen, and possess all the post-translational modifications essential for antigen recognition, including glycosylation and the formation of intra- and intermolecular disulphide bridges.

More specifically, these are "monoclonal antibodies", i.e. they recognize only one antigenic determinant of the VP-1 protein of the BK virus capsid, unlike polyclonal antibodies which correspond to a mixture of antibodies, and can therefore recognize several antigenic determinants of the same protein.

The antibodies described in the invention have the advantage of recognizing (detecting) at least all serotypes Ia (SEQ ID NO: 2), Ib2 (SEQ ID NO: 4), II (SEQ ID NO: 6), III (SEQ ID NO: 8) and IV (SEQ ID NO: 10) of said VP-1 protein of said BK virus. In fact, in addition to advantageously recognizing these 5 serotypes (or genotypes), the antibodies described in the invention can also recognize other subtypes or subgroups of the BK virus. More precisely, the antibodies described are therefore capable of recognizing a VP-1 viral protein represented by a sequence having at least 90%, in particular 93%, identity with the sequence SEQ ID NO: 4. In the sense of the invention, this sequence identity between a sequence of interest (VP-1 protein of the BK virus) and a reference sequence (serotype Ib2 (SEQ ID NO: 4)) being at least 90%, this means that it can be at least 91%, at least 92%, at least 93%, at least 94%, at least 95%, at least 96%, at least 97%, at least 98% or at least 99%. In particular, it is at least 93%. The measurement of this sequence identity, as well as all those described in the invention, are measured by the classic tools for comparing sequences known to the skilled person, such as the algorithms of the BLAST platform or preferably the MatGat2.01 programme under the BLOSUM 50 algorithm (Campanella, J. J., Bitincka, L., & Smalley, J. (2003). MatGAT: an application that generates similarity/identity matrices using protein or DNA sequences. *BMC Bioinformatics*, 4, 29).

The antibodies described in the invention also have the advantage of not crossing with the JC virus. In other words, they are unable to recognize (detect) proteins derived from the JC polyomavirus. This characteristic is moreover easily verifiable by the person skilled in the art by means of classic techniques such as ELISA or Western Blot. (cf Examples).

According to a particular embodiment, the invention concerns a monoclonal antibody directed against the VP-1 protein of the capsid of the BK virus, said VP-1 viral protein being represented by a sequence having at least 90%, in particular 93%, identity with the sequence SEQ ID NO: 4, said monoclonal antibody being capable of recognizing at least all serotypes Ia, Ib2, II, III and IV of said VP-1 protein of said BK virus, said serotypes being respectively represented by the sequences SEQ ID NOs: 2, 4, 6, 8 and 10 or those having at least 90% identity with said sequences SEQ ID NOs: 2, 4, 6, 8 and 10, and said monoclonal antibody not being capable of recognizing the JC virus.

For the purposes of the invention, this sequence identity to SEQ ID NOs: 2, 4, 6, 8 and 10 being at least 90%, this means that it may be at least 91%, at least 92%, at least 93%, at least 94%, at least 95%, at least 96%, at least 97%, at least 98% or at least 99%.

According to another particular embodiment, the invention concerns the monoclonal antibody as described above, said monoclonal antibody not being neutralizing. This means that it is capable of binding to its target, i.e. a VP-1 viral protein represented by a sequence having at least 90%, in particular 93%, identity with the sequence SEQ ID NO: 4, without inhibiting/blocking/neutralizing its biological activity, which corresponds to the entry of the BK virus into a target cell. This characteristic is also easily verifiable by the person in the field using conventional techniques such as sero-neutralisation tests. (cf Examples).

According to another particular embodiment, the invention concerns a monoclonal antibody directed against the VP-1 protein of the capsid of the BK virus, said VP-1 viral protein being represented by a sequence having at least 90%, in particular 93%, identity with the sequence SEQ ID NO: 4, said monoclonal antibody being capable of recognizing at least all serotypes Ia, Ib2, II, III and IV of said VP-1 protein of said BK virus, said monoclonal antibody not being able to recognize the JC virus;

in particular said serotypes being respectively represented by the sequences SEQ ID NOs: 2, 4, 6, 8 and 10 or those having at least 90% identity with said SEQ ID NOs: 2, 4, 6, 8 and 10 sequences, and in particular said monoclonal antibody not being neutralizing.

According to another particular embodiment, the invention concerns the monoclonal antibody as described above comprising:

a heavy chain comprising from its N-terminal end to its C-terminal end:
  a CDR1
    having at least 80% identity with the sequence SEQ ID NO: 12 or
    having at least 80% identity with the sequence SEQ ID NO: 42;
  a CDR2
    having at least 80% identity with the sequence SEQ ID NO: 14 or
    having at least 80% identity with the sequence SEQ ID NO: 44; and
  a CDR3
    having at least 80% identity with the sequence SEQ ID NO: 16 or
    having at least 80% identity with the sequence SEQ ID NO: 46 or
    having at least 80% identity with the sequence SEQ ID NO: 58 or
    having at least 80% identity with the sequence SEQ ID NO: 70;

and a light chain comprising from its N-terminal end to its C-terminal end:
  a CDR1
    having at least 80% identity with the sequence SEQ ID NO: 22 or
    having at least 80% identity with the sequence SEQ ID NO: 32 or
    having at least 80% identity with the sequence SEQ ID NO: 50 or
    having at least 80% identity with the sequence SEQ ID NO: 62 or
    having at least 80% identity with the sequence SEQ ID NO: 74;
  a CDR2
    having at least 80% identity with the sequence SEQ ID NO: 24 or
    having at least 80% identity with the sequence SEQ ID NO: 34 or
    having at least 80% identity with the sequence SEQ ID NO: 52 or
    having at least 80% identity with the sequence SEQ ID NO: 64 or
    having at least 80% identity with the sequence SEQ ID NO: 76; and
  a CDR3
    having at least 80% identity with the sequence SEQ ID NO: 26 or
    having at least 80% identity with the sequence SEQ ID NO: 36 or
    having at least 80% identity with the sequence SEQ ID NO: 54 or
    having at least 80% identity with the sequence SEQ ID NO: 66 or having at least 80% identity with the sequence SEQ ID NO: 78.

According to another particular embodiment, the invention concerns the monoclonal antibody as described above comprising:
a heavy chain comprising from its N-terminal end to its C-terminal end:
a CDR1 having at least 80% identity with the sequence SEQ ID NO: 12;
a CDR2 having at least 80% identity with the sequence SEQ ID NO: 14; and
a CDR3 having at least 80% identity with the sequence SEQ ID NO: 16;
and
a light chain comprising from its N-terminal end to its C-terminal end:
a CDR1 having at least 80% identity with the sequence SEQ ID NO: 22;
a CDR2 having at least 80% identity with the sequence SEQ ID NO: 24; and
a CDR3 having at least 80% identity with the sequence SEQ ID NO: 26;
or
a heavy chain comprising from its N-terminal end to its C-terminal end:
a CDR1 having at least 80% identity with the sequence SEQ ID NO: 12;
a CDR2 having at least 80% identity with the sequence SEQ ID NO: 14; and
a CDR3 having at least 80% identity with the sequence SEQ ID NO: 16;
and
a light chain comprising from its N-terminal end to its C-terminal end:
a CDR1 having at least 80% identity with the sequence SEQ ID NO: 32;
a CDR2 having at least 80% identity with the sequence SEQ ID NO: 34; and
a CDR3 having at least 80% identity with the sequence SEQ ID NO: 36;
or
a heavy chain comprising from its N-terminal end to its C-terminal end:
a CDR1 having at least 80% identity with the sequence SEQ ID NO: 42;
a CDR2 having at least 80% identity with the sequence SEQ ID NO: 44; and
a CDR3 having at least 80% identity with the sequence SEQ ID NO: 46;
and
a light chain comprising from its N-terminal end to its C-terminal end:
a CDR1 having at least 80% identity with the sequence SEQ ID NO: 50;
a CDR2 having at least 80% identity with the sequence SEQ ID NO: 52; and
a CDR3 having at least 80% identity with the sequence SEQ ID NO: 54;
or
a heavy chain comprising from its N-terminal end to its C-terminal end:
a CDR1 having at least 80% identity with the sequence SEQ ID NO: 42;
a CDR2 having at least 80% identity with the sequence SEQ ID NO: 44; and
a CDR3 having at least 80% identity with the sequence SEQ ID NO: 58;
and
a light chain comprising from its N-terminal end to its C-terminal end:
a CDR1 having at least 80% identity with the sequence SEQ ID NO: 62;
a CDR2 having at least 80% identity with the sequence SEQ ID NO: 64; and
a CDR3 having at least 80% identity with the sequence SEQ ID NO: 66;
or
a heavy chain comprising from its N-terminal end to its C-terminal end:
a CDR1 having at least 80% identity with the sequence SEQ ID NO: 42;
a CDR2 having at least 80% identity with the sequence SEQ ID NO: 44; and
a CDR3 having at least 80% identity with the sequence SEQ ID NO: 70;
and
a light chain comprising from its N-terminal end to its C-terminal end:
a CDR1 having at least 80% identity with the sequence SEQ ID NO: 74;
a CDR2 having at least 80% identity with the sequence SEQ ID NO: 76; and
a CDR3 having at least 80% identity with the sequence SEQ ID NO: 78.

According to another particular embodiment, the invention concerns the monoclonal antibody as described above comprising:
a heavy chain comprising from its N-terminal end to its C-terminal end:
a CDR1
having the sequence SEQ ID NO: 12 or
having the sequence SEQ ID NO: 42;
a CDR2
having the sequence SEQ ID NO: 14 or
having the sequence SEQ ID NO: 44; and
a CDR3
having the sequence SEQ ID NO: 16 or
having the sequence SEQ ID NO: 46 or
having the sequence SEQ ID NO: 58 or
having the sequence SEQ ID NO: 70;
and
a light chain comprising from its N-terminal end to its C-terminal end:
a CDR1
having the sequence SEQ ID NO: 22 or
having the sequence SEQ ID NO: 32 or
having the sequence SEQ ID NO: 50 or
having the sequence SEQ ID NO: 62 or
having the sequence SEQ ID NO: 74;
a CDR2
having the sequence SEQ ID NO: 24 or
having the sequence SEQ ID NO: 34 or
having the sequence SEQ ID NO: 52 or
having the sequence SEQ ID NO: 64 or
having the sequence SEQ ID NO: 76; and
a CDR3
having the sequence SEQ ID NO: 26 or
having the sequence SEQ ID NO: 36 or
having the sequence SEQ ID NO: 54 or
having the sequence SEQ ID NO: 66 or
having the sequence SEQ ID NO: 78.

According to another particular embodiment, the invention concerns the monoclonal antibody as described above comprising:

a heavy chain comprising from its N-terminal end to its C-terminal end:
the CDR1 having the sequence SEQ ID NO: 12;
the CDR2 having the sequence SEQ ID NO: 14; and
the CDR3 having the sequence SEQ ID NO: 16;
and
a light chain comprising from its N-terminal end to its C-terminal end:
the CDR1 having the sequence SEQ ID NO: 22;
the CDR2 having the sequence SEQ ID NO: 24; and
the CDR3 having the sequence SEQ ID NO: 26;
or
a heavy chain comprising from its N-terminal end to its C-terminal end:
the CDR1 having the sequence SEQ ID NO: 12;
the CDR2 having the sequence SEQ ID NO: 14; and
the CDR3 having the sequence SEQ ID NO: 16;
and
a light chain comprising from its N-terminal end to its C-terminal end:
the CDR1 having the sequence SEQ ID NO: 32;
the CDR2 having the sequence SEQ ID NO: 34; and
the CDR3 having the sequence SEQ ID NO: 36;
or
a heavy chain comprising from its N-terminal end to its C-terminal end:
the CDR1 having the sequence SEQ ID NO: 42;
the CDR2 having the sequence SEQ ID NO: 44; and
the CDR3 having the sequence SEQ ID NO: 46;
and
a light chain comprising from its N-terminal end to its C-terminal end:
the CDR1 having the sequence SEQ ID NO: 50;
the CDR2 having the sequence SEQ ID NO: 52; and
the CDR3 having the sequence SEQ ID NO: 54;
or
a heavy chain comprising from its N-terminal end to its C-terminal end:
the CDR1 having the sequence SEQ ID NO: 42;
the CDR2 having the sequence SEQ ID NO: 44; and
the CDR3 having the sequence SEQ ID NO: 58;
and
a light chain comprising from its N-terminal end to its C-terminal end:
the CDR1 having the sequence SEQ ID NO: 62;
the CDR2 having the sequence SEQ ID NO: 64; and
the CDR3 having the sequence SEQ ID NO: 66;
or
a heavy chain comprising from its N-terminal end to its C-terminal end:
the CDR1 having the sequence SEQ ID NO: 42;
the CDR2 having the sequence SEQ ID NO: 44; and
the CDR3 having the sequence SEQ ID NO: 70;
and
a light chain comprising from its N-terminal end to its C-terminal end:
the CDR1 having the sequence SEQ ID NO: 74;
the CDR2 having the sequence SEQ ID NO: 76; and
the CDR3 having the sequence SEQ ID NO: 78.

"'F6'/'H6'" SET

According to another particular embodiment, the antibodies described in the invention are constructed from (around) amino acid sequences having a certain percentage of identity with the CDRs of the 'F6' and 'H6' antibodies.

Also and according to this other embodiment, the invention concerns the monoclonal antibody as described above comprising:

a heavy chain comprising from its N-terminal end to its C-terminal end:
a CDR1 having at least 80% identity with the sequence SEQ ID NO: 12;
a CDR2 having at least 80% identity with the sequence SEQ ID NO: 14; and
a CDR3 having at least 80% identity with the sequence SEQ ID NO: 16;
and
a light chain comprising from its N-terminal end to its C-terminal end:
a CDR1 having at least 35% identity with the sequence SEQ ID NO: 22;
a CDR2 having at least 42% identity with the sequence SEQ ID NO: 24; and
a CDR3 having at least 77% identity with the sequence SEQ ID NO: 26.

According to this other embodiment, the invention also concerns the monoclonal antibody as described above comprising:

a heavy chain comprising from its N-terminal end to its C-terminal end:
the CDR1 having the sequence SEQ ID NO: 12;
the CDR2 having the sequence SEQ ID NO: 14; and
the CDR3 having the sequence SEQ ID NO: 16;
and
a light chain comprising from its N-terminal end to its C-terminal end:
a CDR1
having at least 80% identity with the sequence SEQ ID NO: 22 or
having at least 80% identity with the sequence SEQ ID NO: 32;
a CDR2
having at least 80% identity with the sequence SEQ ID NO: 24 or
having at least 80% identity with the sequence SEQ ID NO: 34; and
a CDR3
having at least 80% identity with the sequence SEQ ID NO: 26 or
having at least 80% identity with the sequence SEQ ID NO: 36.

According to this other embodiment, the invention also concerns the monoclonal antibody as described above comprising:

a heavy chain comprising from its N-terminal end to its C-terminal end:
the CDR1 having the sequence SEQ ID NO: 12;
the CDR2 having the sequence SEQ ID NO: 14; and
the CDR3 having the sequence SEQ ID NO: 16;
and
a light chain comprising from its N-terminal end to its C-terminal end:
a CDR1
having the sequence SEQ ID NO: 22 or
having the sequence SEQ ID NO: 32;
a CDR2
having the sequence SEQ ID NO: 24 or
having the sequence SEQ ID NO: 34; and
a CDR3
having the sequence SEQ ID NO: 26 or
having the sequence SEQ ID NO: 36.

"'F6'" SUB-SET

According to another particular embodiment, the antibodies described in the invention are constructed from (around) amino acid sequences corresponding to the CDRs of the 'F6' antibody.

Also and according to this other embodiment, the invention concerns the monoclonal antibody as described above comprising:
- a heavy chain comprising from its N-terminal end to its C-terminal end:
  - the CDR1 having the sequence SEQ ID NO: 12;
  - the CDR2 having the sequence SEQ ID NO: 14; and
  - the CDR3 having the sequence SEQ ID NO: 16;
and
- a light chain comprising from its N-terminal end to its C-terminal end:
  - the CDR1 having the sequence SEQ ID NO: 22;
  - the CDR2 having the sequence SEQ ID NO: 24; and
  - the CDR3 having the sequence SEQ ID NO: 26.

According to this other embodiment, the invention also concerns the monoclonal antibody as described above comprising:
- a heavy chain comprising a variable region having at least 80% identity with the sequence SEQ ID NO: 18; and
- a light chain comprising a variable region having at least 80% identity with the sequence SEQ ID NO: 28.

According to this other embodiment, the invention also concerns the monoclonal antibody as described above comprising:
- a heavy chain comprising a variable region of sequence SEQ ID NO: 18; and
- a light chain comprising a variable region of sequence SEQ ID NO: 28.

According to this other embodiment, the invention also concerns the monoclonal antibody as described above comprising:
- a heavy chain comprising or consisting of a sequence having at least 80% identity with the sequence SEQ ID NO: 20; and
- a light chain comprising or consisting of a sequence having at least 80% identity with the sequence SEQ ID NO: 30.

According to this other embodiment, the invention particularly concerns the monoclonal antibody as described above comprising:
- a heavy chain comprising or consisting of the sequence SEQ ID NO: 20; and
- a light chain comprising or consisting of the sequence SEQ ID NO: 30.

More precisely, this very particular embodiment corresponds to the IgG1/kappa isotype 'F6' monoclonal antibody, which recognises a conformational epitope of the VP-1 viral protein represented by a sequence having at least 90%, in particular 93%, identity with the sequence SEQ ID NO: 4. For the purposes of the invention, the expression "conformational epitope" means that the recognised epitope is formed/constituted by amino acids which are not contiguous in the sequence having at least 90%, in particular 93%, identity with the sequence SEQ ID NO: 4. However, some of said amino acids may be immediately adjacent to each other and thus a conformational epitope according to the present invention may contain only one amino acid which is not contiguous to the others in the sequence having at least 90%, in particular 93%, identity with the sequence SEQ ID NO: 4.

"'H6'" SUB-SET

According to another particular embodiment, the antibodies described in the invention are constructed from (around) amino acid sequences corresponding to the CDRs of the 'H6' antibody.

Also and according to this other embodiment, the invention concerns the monoclonal antibody as described above comprising:
- a heavy chain comprising from its N-terminal end to its C-terminal end:
  - the CDR1 having the sequence SEQ ID NO: 12;
  - the CDR2 having the sequence SEQ ID NO: 14; and
  - the CDR3 having the sequence SEQ ID NO: 16;
and
- a light chain having the sequence comprising from its N-terminal end to its C-terminal end:
  - the CDR1 having the sequence SEQ ID NO: 32;
  - the CDR2 having the sequence SEQ ID NO: 34; and
  - the CDR3 having the sequence SEQ ID NO: 36.

According to this other embodiment, the invention also concerns the monoclonal antibody as described above comprising:
- a heavy chain comprising a variable region having at least 80% identity with the sequence SEQ ID NO: 18; and
- a light chain comprising a variable region having at least 80% identity with the sequence SEQ ID NO: 38.

According to this other embodiment, the invention also concerns the monoclonal antibody as described above comprising:
- a heavy chain comprising a variable region of sequence SEQ ID NO: 18; and
- a light chain comprising a variable region of sequence SEQ ID NO: 38.

According to this other embodiment, the invention also concerns the monoclonal antibody as described above comprising:
- a heavy chain comprising or consisting of a sequence having at least 80% identity with the sequence SEQ ID NO: 20; and
- a light chain comprising or consisting of a sequence having at least 80% identity with the sequence SEQ ID NO: 40.

According to this other embodiment, the invention particularly concerns the monoclonal antibody as described above comprising:
- a heavy chain comprising or consisting of the sequence SEQ ID NO: 20; and
- a light chain comprising or consisting of the sequence SEQ ID NO: 40.

More precisely, this very particular embodiment corresponds to the IgG1/kappa 'H6' monoclonal antibody of IgG1/kappa isotype, which recognises a conformational epitope of the VP-1 viral protein represented by a sequence having at least 90%, in particular 93%, identity with the sequence SEQ ID NO: 4.

"'9B1'/'14D6'/'18A2'" SET

According to another particular embodiment, the antibodies described in the invention are constructed from (around) amino acid sequences having a certain percentage of identity with the CDRs of the '9B1'/'14D6'/'18A2' antibodies.

Also and according to this other embodiment, the invention concerns the monoclonal antibody as described above comprising:
- a heavy chain comprising from its N-terminal end to its C-terminal end:
  - a CDR1 having at least 80% identity with the sequence SEQ ID NO: 42;

a CDR2 having at least 80% identity with the sequence SEQ ID NO: 44; and
a CDR3 having at least 20% identity with the sequence SEQ ID NO: 46;
and
a light chain comprising from its N-terminal end to its C-terminal end:
a CDR1 having at least 18% identity with the sequence SEQ ID NO: 50;
a CDR2 having at least 14% identity with the sequence SEQ ID NO: 52; and
a CDR3 having at least 22% identity with the sequence SEQ ID NO: 54.

According to this other embodiment, the invention also concerns the monoclonal antibody as described above comprising:
a heavy chain comprising from its N-terminal end to its C-terminal end:
the CDR1 having the sequence SEQ ID NO: 42;
the CDR2 having the sequence SEQ ID NO: 44; and
a CDR3
having at least 80% identity with the sequence SEQ ID NO: 46 or
having at least 80% identity with the sequence SEQ ID NO: 58 or
having at least 80% identity with the sequence SEQ ID NO: 70;
and
a light chain comprising from its N-terminal end to its C-terminal end:
a CDR1
having at least 80% identity with the sequence SEQ ID NO: 50 or
having at least 80% identity with the sequence SEQ ID NO: 62 or
having at least 80% identity with the sequence SEQ ID NO: 74;
a CDR2
having at least 80% identity with the sequence SEQ ID NO: 52 or
having at least 80% identity with the sequence SEQ ID NO: 64 or
having at least 80% identity with the sequence SEQ ID NO: 76; and
a CDR3
having at least 80% identity with the sequence SEQ ID NO: 54 or
having at least 80% identity with the sequence SEQ ID NO: 66 or
having at least 80% identity with the sequence SEQ ID NO: 78.

According to this other embodiment, the invention also concerns the monoclonal antibody as described above comprising:
a heavy chain comprising from its N-terminal end to its C-terminal end:
the CDR1 having the sequence SEQ ID NO: 42;
the CDR2 having the sequence SEQ ID NO: 44; and
a CDR3
having the sequence SEQ ID NO: 46 or
having the sequence SEQ ID NO: 58 or
having the sequence SEQ ID NO: 70;
and
a light chain comprising from its N-terminal end to its C-terminal end:
a CDR1
having the sequence SEQ ID NO: 50 or
having the sequence SEQ ID NO: 62 or
having the sequence SEQ ID NO: 74;
a CDR2
having the sequence SEQ ID NO: 52 or
having the sequence SEQ ID NO: 64 or
having the sequence SEQ ID NO: 76; and
a CDR3
having the sequence SEQ ID NO: 54 or
having the sequence SEQ ID NO: 66 or
having the sequence SEQ ID NO: 78.

"'9B1'" SUB-SET

According to another particular embodiment, the antibodies described in the invention are constructed from (around) amino acid sequences corresponding to the CDRs of the '9B1' antibody.

Also and according to this other embodiment, the invention concerns the monoclonal antibody as described above comprising:
a heavy chain comprising from its N-terminal end to its C-terminal end:
the CDR1 having the sequence SEQ ID NO: 42;
the CDR2 having the sequence SEQ ID NO: 44; and
the CDR3 having the sequence SEQ ID NO: 46;
and
a light chain comprising from its N-terminal end to its C-terminal end:
the CDR1 having the sequence SEQ ID NO: 50;
the CDR2 having the sequence SEQ ID NO: 52; and
the CDR3 having the sequence SEQ ID NO: 54.

According to this other embodiment, the invention also concerns the monoclonal antibody as described above comprising:
a heavy chain comprising a variable region having at least 80% identity with the sequence SEQ ID NO: 48; and
a light chain comprising a variable region having at least 80% identity with the sequence SEQ ID NO: 56.

According to this other embodiment, the invention particularly concerns the monoclonal antibody as described above comprising:
a heavy chain comprising a variable region of sequence SEQ ID NO: 48; and
a light chain comprising a variable region of sequence SEQ ID NO: 56.

More precisely, this very particular embodiment corresponds to the monoclonal antibody '9B1', which recognises a conformational epitope of the VP-1 viral protein represented by a sequence having at least 90%, in particular 93%, identity with the sequence SEQ ID NO: 4.

"'14D6'" SUB-SET

According to another particular embodiment, the antibodies described in the invention are constructed from (around) amino acid sequences corresponding to the CDRs of the '14D6' antibody.

Also and according to this other embodiment, the invention concerns the monoclonal antibody as described above comprising:
a heavy chain comprising from its N-terminal end to its C-terminal end:
the CDR1 having the sequence SEQ ID NO: 42;
the CDR2 having the sequence SEQ ID NO: 44; and
the CDR3 having the sequence SEQ ID NO: 58;
and
a light chain comprising from its N-terminal end to its C-terminal end:
the CDR1 having the sequence SEQ ID NO: 62;
the CDR2 having the sequence SEQ ID NO: 64; and
the CDR3 having the sequence SEQ ID NO: 66.

According to this other embodiment, the invention also concerns the monoclonal antibody as described above comprising:
a heavy chain comprising a variable region having at least 80% identity with the sequence SEQ ID NO: 60; and
a light chain comprising a variable region having at least 80% identity with the sequence SEQ ID NO: 68.

According to this other embodiment, the invention particularly concerns the monoclonal antibody as described above comprising:
a heavy chain comprising a variable region of sequence SEQ ID NO: 60; and
a light chain comprising a variable region of sequence SEQ ID NO: 68.

More precisely, this very particular embodiment corresponds to the monoclonal antibody '14D6', which recognises a conformational epitope of the VP-1 viral protein represented by a sequence having at least 90%, in particular 93%, identity with the sequence SEQ ID NO: 4.

'"18A2"' SUB-SET

According to another particular embodiment, the antibodies described in the invention are constructed from (around) amino acid sequences corresponding to the CDRs of the '18A2' antibody.

Also and according to this other embodiment, the invention concerns the monoclonal antibody as described above comprising:
a heavy chain comprising from its N-terminal end to its C-terminal end:
the CDR1 having the sequence SEQ ID NO: 42;
the CDR2 having the sequence SEQ ID NO: 44; and
the CDR3 having the sequence SEQ ID NO: 70;
and
a light chain comprising from its N-terminal end to its C-terminal end:
the CDR1 having the sequence SEQ ID NO: 74;
the CDR2 having the sequence SEQ ID NO: 76; and
the CDR3 having the sequence SEQ ID NO: 78.

According to this other embodiment, the invention also concerns the monoclonal antibody as described above comprising:
a heavy chain comprising a variable region having at least 80% identity with the sequence SEQ ID NO: 72; and
a light chain comprising a variable region having at least 80% identity with the sequence SEQ ID NO: 80.

According to this other embodiment, the invention particularly concerns the monoclonal antibody as described above comprising:
a heavy chain comprising a variable region of sequence SEQ ID NO: 72; and
a light chain comprising a variable region of sequence SEQ ID NO: 80.

More precisely, this very particular embodiment corresponds to the monoclonal antibody '18A2', which, unlike the monoclonal antibodies 'F6', 'H6', '9B1' and '14D6', recognises a linear epitope of the VP-1 viral protein represented by a sequence having at least 90%, in particular 93%, identity with the sequence SEQ ID NO: 4. For the purposes of the invention, the expression "linear epitope" means that the recognised epitope is formed/constituted by amino acids which are all contiguous in the sequence having at least 90%, in particular 93%, identity with the sequence SEQ ID NO: 4.

In particular, the invention also relates to the monoclonal antibody as described above further comprising:
a heavy chain comprising or consisting of the sequence SEQ ID NO: 20; and
a light chain comprising or consisting of the sequence SEQ ID NO: 30,
or
a heavy chain comprising or consisting of the sequence SEQ ID NO: 20; and
a light chain comprising or consisting of the sequence SEQ ID NO: 40,
or
a heavy chain comprising a variable region of sequence SEQ ID NO: 48; and
a light chain comprising a variable region of sequence SEQ ID NO: 56,
or
a heavy chain comprising a variable region of sequence SEQ ID NO: 60; and
a light chain comprising a variable region of sequence SEQ ID NO: 68,
or
a heavy chain comprising a variable region of sequence SEQ ID NO: 72; and
a light chain comprising a variable region of sequence SEQ ID NO: 80.

In the invention described above, reference is made to sequence identities in relation to particular CDRs, particular variable regions, particular light chains or particular heavy chains. For all these references, the percentage of identity mentioned can be measured, from the said reference sequences as a whole, by the classical tools for comparing sequences known to the skilled person, such as the algorithms of the BLAST platform or preferably the MatGat2.01 programme under the BLOSUM 50 algorithm (Campanella, J. J., Bitincka, L., & Smalley, J. (2003). MatGAT: an application that generates similarity/identity matrices using protein or DNA sequences. *BMC Bioinformatics*, 4, 29). In addition, it should be noted, for example, that the reference to a sequence identity of at least 14% means that it can be at least 18%, at least 22%, at least 25%; at least 30%, at least 35%, at least 40%, at least 42%, at least 45%, at least 50%, at least 55%, at least 60%, at least 65%, at least 70%, at least 75%, at least 77%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99%. In fact, for the purposes of the invention, the reference to a sequence identity of at least 80% means that it may be at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99%.

A second aspect of the invention concerns a fragment of a monoclonal antibody as described above. In the invention, the term "fragment" refers to any part of an antibody which retains the ability to bind to the epitope recognised by the complete antibody. Examples of such fragments include, but are not limited to, Fab, Fab' and F(ab')$_2$, Fd, single chain Fvs (scFv), single chain antibodies, disulfide bonded Fvs (dsFv) and fragments comprising the $V_L$ or $V_H$ region. Fragments binding to the epitope, including single chain antibodies, may comprise the variable region(s) alone or in combination with all or some of the following: hinge region, $C_H1$, $C_H2$ and $C_H3$ domains.

Such fragments may contain one or both Fab fragments or the F(ab')$_2$ fragment. In addition, the fragments may be or may combine members of any of the following immunoglobulin classes: IgG, IgM, IgA, IgD or IgE and their subclasses.

The Fab and F(ab')₂ fragments can be produced by proteolytic cleavage, using enzymes such as papain (Fab fragment) or pepsin (F(ab')₂ fragment).

Single chain Fv fragments ("scFv") are epitope-binding fragments that contain at least one fragment of an antibody variable region ($V_H$) linked to at least one fragment of a light chain antibody variable region ($V_L$). The linker may be a short, flexible peptide selected to ensure that correct three-dimensional folding of the $V_L$ and $V_H$ regions occurs once they are bound, so as to maintain the binding specificity to the target molecule of the whole antibody from which the single-chain antibody fragment is derived. The carboxyl end of the $V_L$ or $V_H$ sequence may be covalently linked by a binding agent to the amino acid end of a complementary $V_L$ or $V_H$ sequence.

According to a particular embodiment of this aspect, the invention concerns a fragment of a monoclonal antibody as described above, said fragment being selected from the group of fragments consisting of: Fv, Fab, F(ab')₂, Fab', dsFv, scFv, sc(Fv)₂, "diabodies".

A third aspect of the invention concerns a nucleic acid comprising or consisting of a sequence encoding
  the heavy chain of a monoclonal antibody as described above and/or the light chain of a monoclonal antibody as described above; or
  the fragment as described above.

According to a particular embodiment of this aspect, the invention concerns the nucleic acid as described above comprising or consisting of a sequence coding for
  a heavy chain comprising from its N-terminal end to its C-terminal end:
    a CDR1
      having at least 80% identity with the sequence SEQ ID NO: 11 or
      having at least 80% identity with the sequence SEQ ID NO: 41;
    a CDR2
      having at least 80% identity with the sequence SEQ ID NO: 13 or
      having at least 80% identity with the sequence SEQ ID NO: 43; and
    a CDR3
      having at least 80% identity with the sequence SEQ ID NO: 15 or
      having at least 80% identity with the sequence SEQ ID NO: 45 or
      having at least 80% identity with the sequence SEQ ID NO: 57 or
      having at least 80% identity with the sequence SEQ ID NO: 69;
  and/or
  a light chain comprising from its N-terminal end to its C-terminal end:
    a CDR1
      having at least 80% identity with the sequence SEQ ID NO: 21 or
      having at least 80% identity with the sequence SEQ ID NO: 31 or
      having at least 80% identity with the sequence SEQ ID NO: 49 or
      having at least 80% identity with the sequence SEQ ID NO: 61 or
      having at least 80% identity with the sequence SEQ ID NO: 73;
    a CDR2
      having at least 80% identity with the sequence SEQ ID NO: 23 or
      having at least 80% identity with the sequence SEQ ID NO: 33 or
      having at least 80% identity with the sequence SEQ ID NO: 51 or
      having at least 80% identity with the sequence SEQ ID NO: 63 or
      having at least 80% identity with the sequence SEQ ID NO: 75; and
    a CDR3
      having at least 80% identity with the sequence SEQ ID NO: 25 or
      having at least 80% identity with the sequence SEQ ID NO: 35 or
      having at least 80% identity with the sequence SEQ ID NO: 53 or
      having at least 80% identity with the sequence SEQ ID NO: 65 or
      having at least 80% identity with the sequence SEQ ID NO: 77.

According to another particular embodiment of this aspect, the invention concerns the nucleic acid as described above comprising or consisting of a sequence coding for
  a heavy chain comprising from its N-terminal end to its C-terminal end:
    a CDR1 having at least 80% identity with the sequence SEQ ID NO: 11;
    a CDR2 having at least 80% identity with the sequence SEQ ID NO: 13; and
    a CDR3 having at least 80% identity with the sequence SEQ ID NO: 15; and/or
  a light chain comprising from its N-terminal end to its C-terminal end:
    a CDR1 having at least 80% identity with the sequence SEQ ID NO: 21;
    a CDR2 having at least 80% identity with the sequence SEQ ID NO: 23; and
    a CDR3 having at least 80% identity with the sequence SEQ ID NO: 25;
  or
  a heavy chain comprising from its N-terminal end to its C-terminal end:
    a CDR1 having at least 80% identity with the sequence SEQ ID NO: 11;
    a CDR2 having at least 80% identity with the sequence SEQ ID NO: 13; and
    a CDR3 having at least 80% identity with the sequence SEQ ID NO: 15; and/or
  a light chain comprising from its N-terminal end to its C-terminal end:
    a CDR1 having at least 80% identity with the sequence SEQ ID NO: 31;
    a CDR2 having at least 80% identity with the sequence SEQ ID NO: 33; and
    a CDR3 having at least 80% identity with the sequence SEQ ID NO: 35;
  or
  a heavy chain comprising from its N-terminal end to its C-terminal end:
    a CDR1 having at least 80% identity with the sequence SEQ ID NO: 41;
    a CDR2 having at least 80% identity with the sequence SEQ ID NO: 43; and
    a CDR3 having at least 80% identity with the sequence SEQ ID NO: 45; and/or
  a light chain comprising from its N-terminal end to its C-terminal end:
    a CDR1 having at least 80% identity with the sequence SEQ ID NO: 49;

a CDR2 having at least 80% identity with the sequence SEQ ID NO: 51; and
a CDR3 having at least 80% identity with the sequence SEQ ID NO: 53;
or
a heavy chain comprising from its N-terminal end to its C-terminal end:
a CDR1 having at least 80% identity with the sequence SEQ ID NO: 41;
a CDR2 having at least 80% identity with the sequence SEQ ID NO: 43; and
a CDR3 having at least 80% identity with the sequence SEQ ID NO: 57; and/or
a light chain comprising from its N-terminal end to its C-terminal end:
a CDR1 having at least 80% identity with the sequence SEQ ID NO: 61;
a CDR2 having at least 80% identity with the sequence SEQ ID NO: 63; and
a CDR3 having at least 80% identity with the sequence SEQ ID NO: 65;
or
a heavy chain comprising from its N-terminal end to its C-terminal end:
a CDR1 having at least 80% identity with the sequence SEQ ID NO: 41;
a CDR2 having at least 80% identity with the sequence SEQ ID NO: 43; and
a CDR3 having at least 80% identity with the sequence SEQ ID NO: 69;
and/or
a light chain comprising from its N-terminal end to its C-terminal end:
a CDR1 having at least 80% identity with the sequence SEQ ID NO: 73;
a CDR2 having at least 80% identity with the sequence SEQ ID NO: 75; and
a CDR3 having at least 80% identity with the sequence SEQ ID NO: 77.

According to another particular embodiment of this aspect, the invention concerns the nucleic acid as described above comprising or consisting of a sequence coding for
a heavy chain comprising from its N-terminal end to its C-terminal end:
a CDR1
having the sequence SEQ ID NO: 11 or
having the sequence SEQ ID NO: 41;
a CDR2
having the sequence SEQ ID NO: 13 or
having the sequence SEQ ID NO: 43; and
a CDR3
having the sequence SEQ ID NO: 15 or
having the sequence SEQ ID NO: 45 or
having the sequence SEQ ID NO: 57 or
having the sequence SEQ ID NO: 69;
and/or
a light chain comprising from its N-terminal end to its C-terminal end:
a CDR1
having the sequence SEQ ID NO: 21 or
having the sequence SEQ ID NO: 31 or
having the sequence SEQ ID NO: 49 or
having the sequence SEQ ID NO: 61 or
having the sequence SEQ ID NO: 73;
a CDR2
having the sequence SEQ ID NO: 23 or
having the sequence SEQ ID NO: 33 or
having the sequence SEQ ID NO: 51 or
having the sequence SEQ ID NO: 63 or
having the sequence SEQ ID NO: 75; and
a CDR3
having the sequence SEQ ID NO: 25 or
having the sequence SEQ ID NO: 35 or
having the sequence SEQ ID NO: 53 or
having the sequence SEQ ID NO: 65 or
having the sequence SEQ ID NO: 77.

According to another particular embodiment of this aspect, the invention concerns the nucleic acid as described above comprising or consisting of a sequence coding for
a heavy chain comprising from its N-terminal end to its C-terminal end:
the CDR1 having the sequence SEQ ID NO: 11;
the CDR2 having the sequence SEQ ID NO: 13; and
the CDR3 having the sequence SEQ ID NO: 15;
and/or
a light chain comprising from its N-terminal end to its C-terminal end:
the CDR1 having the sequence SEQ ID NO: 21;
the CDR2 having the sequence SEQ ID NO: 23; and
the CDR3 having the sequence SEQ ID NO: 25;
or
a heavy chain comprising from its N-terminal end to its C-terminal end:
the CDR1 having the sequence SEQ ID NO: 11;
the CDR2 having the sequence SEQ ID NO: 13; and
the CDR3 having the sequence SEQ ID NO: 15;
and/or
a light chain comprising from its N-terminal end to its C-terminal end:
the CDR1 having the sequence SEQ ID NO: 31;
the CDR2 having the sequence SEQ ID NO: 33; and
the CDR3 having the sequence SEQ ID NO: 35;
or
a heavy chain comprising from its N-terminal end to its C-terminal end:
the CDR1 having the sequence SEQ ID NO: 41;
the CDR2 having the sequence SEQ ID NO: 43; and
the CDR3 having the sequence SEQ ID NO: 45;
and/or
a light chain comprising from its N-terminal end to its C-terminal end:
the CDR1 having the sequence SEQ ID NO: 49;
the CDR2 having the sequence SEQ ID NO: 51; and
the CDR3 having the sequence SEQ ID NO: 53;
or
a heavy chain comprising from its N-terminal end to its C-terminal end:
the CDR1 having the sequence SEQ ID NO: 41;
the CDR2 having the sequence SEQ ID NO: 43; and
the CDR3 having the sequence SEQ ID NO: 57;
and/or
a light chain comprising from its N-terminal end to its C-terminal end:
the CDR1 having the sequence SEQ ID NO: 61;
the CDR2 having the sequence SEQ ID NO: 63; and
the CDR3 having the sequence SEQ ID NO: 65;
or
a heavy chain comprising from its N-terminal end to its C-terminal end:
the CDR1 having the sequence SEQ ID NO: 41;
the CDR2 having the sequence SEQ ID NO: 43; and
the CDR3 having the sequence SEQ ID NO: 69;
and/or a light chain comprising from its N-terminal end to its C-terminal end:
   the CDR1 having the sequence SEQ ID NO: 73;
   the CDR2 having the sequence SEQ ID NO: 75; and
   the CDR3 having the sequence SEQ ID NO: 77.

"'F6'/'H69'" SET

In another particular way, the antibodies described in the invention are constructed from (around) nucleic acid sequences having a certain percentage of identity with those encoding the CDRs of the 'F6' and 'H6' antibodies.

Also and according to this other embodiment, the invention concerns the nucleic acid as described above comprising or consisting of a sequence coding for
a heavy chain comprising from its N-terminal end to its C-terminal end:
   a CDR1 having at least 80% identity with the sequence SEQ ID NO: 11;
   a CDR2 having at least 80% identity with the sequence SEQ ID NO: 13; and
   a CDR3 having at least 80% identity with the sequence SEQ ID NO: 15;
and/or
a light chain comprising from its N-terminal end to its C-terminal end:
   a CDR1 having at least 49% identity with the sequence SEQ ID NO: 21;
   a CDR2 having at least 61% identity with the sequence SEQ ID NO: 23; and
   a CDR3 having at least 85% identity with the sequence SEQ ID NO: 25.

According to this other mode of implementation, the invention also concerns the nucleic acid as described above comprising or consisting of a sequence coding for
a heavy chain comprising from its N-terminal end to its C-terminal end:
   the CDR1 having the sequence SEQ ID NO: 11;
   the CDR2 having the sequence SEQ ID NO: 13; and
   the CDR3 having the sequence SEQ ID NO: 15;
and/or
a light chain comprising from its N-terminal end to its C-terminal end:
   a CDR1
      having at least 80% identity with the sequence SEQ ID NO: 21 or
      having at least 80% identity with the sequence SEQ ID NO: 31;
   a CDR2
      having at least 80% identity with the sequence SEQ ID NO: 23 or
      having at least 80% identity with the sequence SEQ ID NO: 33; and
   a CDR3
      having at least 80% identity with the sequence SEQ ID NO: 25 or
      having at least 80% identity with the sequence SEQ ID NO: 35.

According to this other mode of implementation, the invention also concerns the nucleic acid as described above comprising or consisting of a sequence coding for
a heavy chain comprising from its N-terminal end to its C-terminal end:
   the CDR1 having the sequence SEQ ID NO: 11;
   the CDR2 having the sequence SEQ ID NO: 13; and
   the CDR3 having the sequence SEQ ID NO: 15;
and/or
a light chain comprising from its N-terminal end to its C-terminal end:
   a CDR1
      having the sequence SEQ ID NO: 21 or
      having the sequence SEQ ID NO: 31;
   a CDR2
      having the sequence SEQ ID NO: 23 or
      having the sequence SEQ ID NO: 33; and
   a CDR3
      having the sequence SEQ ID NO: 25 or
      having the sequence SEQ ID NO: 35.

"'F6'" SUB-SET

In another particular way, the antibodies described in the invention are constructed from (around) nucleic acid sequences coding for the CDRs of the 'F6' antibody.

Also and according to this other embodiment, the invention concerns the nucleic acid as described above comprising or consisting of a sequence coding for
a heavy chain comprising from its N-terminal end to its C-terminal end:
   the CDR1 having the sequence SEQ ID NO: 11;
   the CDR2 having the sequence SEQ ID NO: 13; and
   the CDR3 having the sequence SEQ ID NO: 15;
and/or
a light chain comprising from its N-terminal end to its C-terminal end:
   the CDR1 having the sequence SEQ ID NO: 21;
   the CDR2 having the sequence SEQ ID NO: 23; and
   the CDR3 having the sequence SEQ ID NO: 25.

According to this other mode of implementation, the invention also concerns the nucleic acid as described above comprising or consisting of a sequence coding for
a heavy chain comprising a variable region having at least 80% identity with the sequence SEQ ID NO: 17; and/or
a light chain comprising a variable region having at least 80% identity with the sequence SEQ ID NO: 27.

According to this other mode of implementation, the invention also concerns the nucleic acid as described above comprising or consisting of a sequence coding for
a heavy chain comprising a variable region of sequence SEQ ID NO: 17; and/or
a light chain comprising a variable region of sequence SEQ ID NO: 27.

According to this other mode of implementation, the invention also concerns the nucleic acid as described above comprising or consisting of a sequence coding for
a heavy chain comprising or consisting of a sequence having at least 80% identity with the sequence SEQ ID NO: 19; and/or
a light chain comprising or consisting of a sequence having at least 80% identity with the sequence SEQ ID NO: 29.

According to this other mode of implementation, the invention concerns in particular the nucleic acid as described above comprising or consisting of a sequence coding for
a heavy chain comprising or consisting of the sequence SEQ ID NO: 19; and/or
a light chain comprising or consisting of the sequence SEQ ID NO: 29.

More precisely, this very special method of production corresponds to the nucleic acid encoding the monoclonal antibody 'F6'.

"'H6'" SUB-SET

In another particular way, the antibodies described in the invention are constructed from (around) nucleic acid sequences coding for the CDRs of the 'H6' antibody.

Also and according to this other embodiment, the invention concerns the nucleic acid as described above comprising or consisting of a sequence coding for
a heavy chain comprising from its N-terminal end to its C-terminal end:
the CDR1 having the sequence SEQ ID NO: 11;
the CDR2 having the sequence SEQ ID NO: 13; and
the CDR3 having the sequence SEQ ID NO: 15;
and/or
a light chain comprising from its N-terminal end to its C-terminal end:
the CDR1 having the sequence SEQ ID NO: 31;
the CDR2 having the sequence SEQ ID NO: 33; and
the CDR3 having the sequence SEQ ID NO: 35.

According to this other mode of implementation, the invention also concerns the nucleic acid as described above comprising or consisting of a sequence coding for
a heavy chain comprising a variable region having at least 80% identity with the sequence SEQ ID NO: 17; and/or
a light chain comprising a variable region having at least 80% identity with the sequence SEQ ID NO: 37.

According to this other mode of implementation, the invention also concerns the nucleic acid as described above comprising or consisting of a sequence coding for
a heavy chain comprising a variable region of sequence SEQ ID NO: 17; and/or
a light chain comprising a variable region of sequence SEQ ID NO: 37.

According to this other mode of implementation, the invention also concerns the nucleic acid as described above comprising or consisting of a sequence coding for
a heavy chain comprising or consisting of a sequence having at least 80% identity with the sequence SEQ ID NO: 19; and/or
a light chain comprising or consisting of a sequence having at least 80% identity with the sequence SEQ ID NO: 39.

According to this other mode of implementation, the invention concerns in particular the nucleic acid as described above comprising or consisting of a sequence coding for
a heavy chain comprising or consisting of the sequence SEQ ID NO: 19; and/or
a light chain comprising or consisting of the sequence SEQ ID NO: 39.

More precisely, this very special method of production corresponds to the nucleic acid encoding the monoclonal antibody 'H6'.

'''9B1'/'14D6'/'18A2''' SET

According to another particular embodiment, the antibodies described in the invention are constructed from (around) nucleic acid sequences having a certain percentage of identity with those coding for the CDRs of the '9B1'/'14D6'/'18A2' antibodies.

Also and according to this other embodiment, the invention concerns the nucleic acid as described above comprising or consisting of a sequence coding for
a heavy chain comprising from its N-terminal end to its C-terminal end:
a CDR1 having at least 80% identity with the sequence SEQ ID NO: 41;
a CDR2 having at least 80% identity with the sequence SEQ ID NO: 43; and
a CDR3 having at least 50% identity with the sequence SEQ ID NO: 45; and/or
a light chain comprising from its N-terminal end to its C-terminal end:
a CDR1 having at least 45% identity with the sequence SEQ ID NO: 49;
a CDR2 having at least 42% identity with the sequence SEQ ID NO: 51; and
a CDR3 having at least 40% identity with the sequence SEQ ID NO: 53.

According to this other mode of implementation, the invention also concerns the nucleic acid as described above comprising or consisting of a sequence coding for
a heavy chain comprising from its N-terminal end to its C-terminal end:
the CDR1 having the sequence SEQ ID NO: 41;
the CDR2 having the sequence SEQ ID NO: 43; and
a CDR3
having at least 80% identity with the sequence SEQ ID NO: 45 or
having at least 80% identity with the sequence SEQ ID NO: 57 or
having at least 80% identity with the sequence SEQ ID NO: 69;
and/or
a light chain comprising from its N-terminal end to its C-terminal end:
a CDR1
having at least 80% identity with the sequence SEQ ID NO: 49 or
having at least 80% identity with the sequence SEQ ID NO: 61 or
having at least 80% identity with the sequence SEQ ID NO: 73;
a CDR2
having at least 80% identity with the sequence SEQ ID NO: 51 or
having at least 80% identity with the sequence SEQ ID NO: 63 or
having at least 80% identity with the sequence SEQ ID NO: 75; and
a CDR3
having at least 80% identity with the sequence SEQ ID NO: 53 or
having at least 80% identity with the sequence SEQ ID NO: 65 or
having at least 80% identity with the sequence SEQ ID NO: 77.

According to this other mode of implementation, the invention also concerns the nucleic acid as described above comprising or consisting of a sequence coding for
a heavy chain comprising from its N-terminal end to its C-terminal end:
the CDR1 having the sequence SEQ ID NO: 41;
the CDR2 having the sequence SEQ ID NO: 43; and
a CDR3
having the sequence SEQ ID NO: 45 or
having the sequence SEQ ID NO: 57 or
having the sequence SEQ ID NO: 69;
and/or
a light chain comprising from its N-terminal end to its C-terminal end:
a CDR1
having the sequence SEQ ID NO: 49 or
having the sequence SEQ ID NO: 61 or
having the sequence SEQ ID NO: 73;
a CDR2
having the sequence SEQ ID NO: 51 or
having the sequence SEQ ID NO: 63 or
having the sequence SEQ ID NO: 75; and a CDR3
    having the sequence SEQ ID NO: 53 or
    having the sequence SEQ ID NO: 65 or
    having the sequence SEQ ID NO: 77.

"'9B1'" SUB-SET

According to another particular mode of production, the antibodies described in the invention are constructed from (around) nucleic acid sequences coding for the CDRs of the '9B1' antibody.

Also and according to this other embodiment, the invention concerns the nucleic acid as described above comprising or consisting of a sequence coding for
    a heavy chain comprising from its N-terminal end to its C-terminal end:
        the CDR1 having the sequence SEQ ID NO: 41;
        the CDR2 having the sequence SEQ ID NO: 43; and
        the CDR3 having the sequence SEQ ID NO: 45;
    and/or
    a light chain comprising from its N-terminal end to its C-terminal end:
        the CDR1 having the sequence SEQ ID NO: 49;
        the CDR2 having the sequence SEQ ID NO: 51; and
        the CDR3 having the sequence SEQ ID NO: 53.

According to this other mode of implementation, the invention also concerns the nucleic acid as described above comprising or consisting of a sequence coding for
    a heavy chain comprising a variable region having at least 80% identity with the sequence SEQ ID NO: 47; and/or
    a light chain comprising a variable region having at least 80% identity with the sequence SEQ ID NO: 55.

According to this other mode of implementation, the invention concerns in particular the nucleic acid as described above comprising or consisting of a sequence coding for
    a heavy chain comprising a variable region of sequence SEQ ID NO: 47; and/or
    a light chain comprising a variable region of sequence SEQ ID NO: 55.

More precisely, this very special method of production corresponds to the nucleic acid encoding the monoclonal antibody '9B1'.

"'14D6'" SUB-SET

In another particular way, the antibodies described in the invention are constructed from (around) nucleic acid sequences coding for the CDRs of the '14D6' antibody.

Also and according to this other embodiment, the invention concerns the nucleic acid as described above comprising or consisting of a sequence coding for
    a heavy chain comprising from its N-terminal end to its C-terminal end:
        the CDR1 having the sequence SEQ ID NO: 41;
        the CDR2 having the sequence SEQ ID NO: 43; and
        the CDR3 having the sequence SEQ ID NO: 57;
    and/or
    a light chain comprising from its N-terminal end to its C-terminal end:
        the CDR1 having the sequence SEQ ID NO: 61;
        the CDR2 having the sequence SEQ ID NO: 63; and
        the CDR3 having the sequence SEQ ID NO: 65.

According to this other mode of implementation, the invention also concerns the nucleic acid as described above comprising or consisting of a sequence coding for
    a heavy chain comprising a variable region having at least 80% identity with the sequence SEQ ID NO: 59; and/or
    a light chain comprising a variable region having at least 80% identity with the sequence SEQ ID NO: 67.

According to this other mode of implementation, the invention concerns in particular the nucleic acid as described above comprising or consisting of a sequence coding for
    a heavy chain comprising a variable region of sequence SEQ ID NO: 59; and/or
    a light chain comprising a variable region of sequence SEQ ID NO: 67.

More precisely, this very special production method corresponds to the nucleic acid encoding the monoclonal antibody '14D6'.

"'18A2'" SUB-SET

According to another particular embodiment, the antibodies described in the invention are constructed from (around) nucleic acid sequences coding for the CDRs of the '18A2' antibody.

Also and according to this other embodiment, the invention concerns the nucleic acid as described above comprising or consisting of a sequence coding for
    a heavy chain comprising from its N-terminal end to its C-terminal end:
        the CDR1 having the sequence SEQ ID NO: 41;
        the CDR2 having the sequence SEQ ID NO: 43; and
        the CDR3 having the sequence SEQ ID NO: 69;
    and/or
    a light chain comprising from its N-terminal end to its C-terminal end:
        the CDR1 having the sequence SEQ ID NO: 73;
        the CDR2 having the sequence SEQ ID NO: 75; and
        the CDR3 having the sequence SEQ ID NO: 77.

According to this other mode of implementation, the invention also concerns the nucleic acid as described above comprising or consisting of a sequence coding for
    a heavy chain comprising a variable region having at least 80% identity with the sequence SEQ ID NO: 71; and/or
    a light chain comprising a variable region having at least 80% identity with the sequence SEQ ID NO: 79.

According to this other mode of implementation, the invention concerns in particular the nucleic acid as described above comprising or consisting of a sequence coding for
    a heavy chain comprising a variable region of sequence SEQ ID NO: 71; and/or
    a light chain comprising a variable region of sequence SEQ ID NO: 79.

More precisely, this very special production method corresponds to the nucleic acid encoding the monoclonal antibody '18A2'.

In particular, the invention also relates to nucleic acid as described above further comprising:
    a heavy chain comprising or consisting of the sequence SEQ ID NO: 19; and
    a light chain comprising or consisting of the sequence SEQ ID NO: 29,
or
    a heavy chain comprising or consisting of the sequence SEQ ID NO: 19; and
    a light chain comprising or consisting ofthe sequence SEQ ID NO: 39,
or
    a heavy chain comprising a variable region of sequence SEQ ID NO: 47; and
    a light chain comprising a variable region of sequence SEQ ID NO: 55,
or
    a heavy chain comprising a variable region of sequence SEQ ID NO: 59; and a light chain comprising a variable region of sequence SEQ ID NO: 67, or a heavy chain comprising a variable region of sequence SEQ ID NO: 71; and a light chain comprising a variable region of sequence SEQ ID NO: 79.

In the invention described above, reference is made to sequence identities with respect to nucleic acids encoding particular CDRs, particular variable regions, particular light chains or particular heavy chains. For all these references, the percentage of identity mentioned can be measured, from the said reference sequences as a whole, by the classical tools for comparing sequences known to the skilled person, such as the algorithms of the BLAST platform or preferably the MatGat2.01 programme (Campanella, J. J., Bitincka, L., & Smalley, J. (2003). MatGAT: an application that generates similarity/identity matrices using protein or DNA sequences. *BMC Bioinformatics*, 4, 29). In addition, it should be noted, for example, that the reference to a sequence identity of at least 40% means that it may be at least 42%, at least 45%, at least 49%, at least 50%, at least 55%, at least 60%, at least 61%, at least 65%, at least 70%, at least 75%, at least 77%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99%. In fact, for the purposes of the invention, the reference to a sequence identity of at least 80% means that it may be at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99%.

According to another embodiment of this third aspect, the invention concerns an expression vector comprising at least one nucleic acid as described above, said nucleic acid being under the control of elements allowing its expression.

The term "expression vector" is defined in the invention as a DNA molecule that possesses elements that allow its replication (duplication) in at least one living organism. These replication-permitting elements are, in particular, yeast or bacterial replication origins, or elements for controlling the replication of a virus.

The vectors according to the invention are in particular plasmids, phages, artificial chromosomes of yeast (YAC), artificial chromosomes of bacteria (BAC), modified genomes of replicative or integrative viruses, etc.

These vectors are called "expression" vectors because they have nucleotide sequences that allow the expression, i.e. transcription into RNA, of the nucleotide sequences they control.

In the invention, the said nucleic acid sequence contained in the said vector is placed "under the control of the elements allowing its expression". This means that said expression vector has at least one transcription initiation sequence such as a virus promoter such as the early promoter of the simian virus SV40, or of the Cytomegalovirus (CMV) or the promoter sequences of the Rous sarcoma virus (RSV), and in particular a sequence or promoter comprising a TATAA box. In addition, said vector also has at least one transcription termination sequence, and in particular a polyadenylation sequence from a mammalian gene, in particular a human gene.

To these sequences, which are indispensable for the expression of the nucleotide sequence contained in the said vector, other sequences may be added which make it possible to regulate or modulate the expression of the said sequence. A non-exhaustive list includes: introns of mammalian genes, in particular human genes, enhancer-type transcription regulation sequences ("enhancers") or transcribed but untranslated sequences of mammalian genes, in particular human genes.

A particular embodiment of the invention concerns a vector of expression as defined above, comprising a first nucleic acid selected from those encoding all or part of the heavy chain of the monoclonal antibody as described above, said first nucleic acid being under the control of the elements permitting its expression; and a second nucleic acid selected from those encoding all or part of the light chain of the monoclonal antibody as described above, said second nucleic acid being under the control of the elements permitting its expression.

This expression vector therefore comprises two nucleic acid sequences as mentioned above, and more specifically comprises a nucleic acid sequence encoding the heavy chain of the monoclonal antibody as described above, and a nucleic acid sequence encoding the light chain of the monoclonal antibody as described above.

Preferentially, said expression vector contains a first element allowing the expression of the nucleic acid sequence encoding the heavy chain of the monoclonal antibody as described above and a second element allowing the expression of the nucleic acid sequence encoding the light chain of the monoclonal antibody as described above, said first and said second element allowing the expression of said nucleic acid sequences being identical or different, and preferably identical. These control elements are in particular the long terminal repeated sequences (LTR) of the RSV virus.

According to another embodiment of this third aspect, the invention concerns a host cell or cell line transformed by a nucleic acid as described above and/or an expression vector as described above.

According to another aspect of the invention, it concerns an antibody/antigen immune complex, in which:

said antibody is the monoclonal antibody as previously described or a fragment as previously described; and the antigen is the VP-1 protein of the capsid of the BK virus, said VP-1 viral protein being represented by a sequence having at least 90%, in particular 93%, identity with the sequence SEQ ID NO: 4, or a fragment thereof comprising at least the epitope recognised by said antibody as described above or said fragment as described above.

According to a particular way of carrying out this aspect, the invention concerns the immune antibody/antigen complex as described above, in which said viral protein VP-1 is represented by at least one of the serotypes Ia, Ib2, II, III and/or IV of said VP-1 protein of said BK virus, said serotypes being respectively represented by the sequences SEQ ID NOs: 2, 4, 6, 8 and/or 10 or those having at least 90% identity with said sequences SEQ ID NOs: 2, 4, 6, 8 and/or 10.

In particular, the invention also relates to an antibody/antigen immune complex, in which:

said antibody is the monoclonal antibody as previously described or a fragment as previously described; and the antigen is the VP-1 protein of the capsid of the BK virus, said VP-1 viral protein being represented by a sequence having at least 90%, in particular 93%, identity with the sequence SEQ ID NO: 4, or a fragment thereof comprising at least the epitope recognised by said antibody as described above or a fragment as described above, in particular said VP-1 viral protein being represented by at least one of the serotypes Ia, Ib2, II, III and/or IV of said VP-1 protein of said BK virus, said serotypes being respectively represented by the sequences SEQ ID NOs: 2, 4, 6, 8 and/or 10 or those having at least 90% identity with said sequences SEQ ID NOs: 2, 4, 6, 8 and/or 10.

According to the same aspect, the invention also relates to an in vitro or ex vivo diagnostic method for detecting a BK virus infection in a patient comprising:
a step of detection in a biological sample from said patient of the immune antibody/antigen complex as described above using a monoclonal antibody as described above or a fragment as described above,
said biological sample being in particular blood or urine.

According to the same aspect, the invention also concerns a diagnostic kit for detecting in a biological sample the VP-1 protein of the capsid of the BK virus, said VP-1 viral protein being represented by a sequence having at least 90%, in particular 93%, identity with the sequence SEQ ID NO: 4, or one of its fragments comprising at least the epitope recognised by said antibody as described above or one of its fragments as described above,
comprising a monoclonal antibody as described above or a fragment as described above.

According to a particular embodiment, the invention also concerns the above diagnostic kit, in which said VP-1 viral protein is represented by at least one of the serotypes Ia, Ib2, II, III and/or IV of said VP-1 protein of said BK virus, said serotypes being respectively represented by the sequences SEQ ID NOs: 2, 4, 6, 8 and/or 10 or those having at least 90% identity with said sequences SEQ ID NOs: 2, 4, 6, 8 and/or 10.

In particular, the invention also concerns a diagnostic kit for detecting in a biological sample the VP-1 protein of the capsid of the BK virus, said VP-1 viral protein being represented by a sequence having at least 90%, in particular 93%, identity with the sequence SEQ ID NO: 4, or one of its fragments comprising at least the epitope recognised by said as previously described or said fragment as previously described,
comprising a monoclonal antibody as previously described or said fragment as previously described,
in particular said VP-1 viral protein being represented by at least one of the serotypes Ia, Ib2, II, III and/or IV of said VP-1 protein of said BK virus, said serotypes being respectively represented by the sequences SEQ ID NOs: 2, 4, 6, 8 and/or 10 or those having at least 90% identity with said sequences SEQ ID NOs: 2, 4, 6, 8 and/or 10.

As the man skilled in the art, most diagnostic kits include immuno-chromatography tests on strips, which are modelled on the format of enzyme immunoassays, i.e. sandwich type assays. Many variations are therefore possible, but they all have in common the formation of an antibody/antigen immune complex between:
a particle to be detected, here the BK virus via its capsid protein VP-1, said particle being free in the biological sample stream (e.g. blood and/or urine); and
a capture reagent, here the monoclonal antibody of the invention or one of its fragments, said monoclonal antibody of the invention or one of its fragments being coupled with a tracer, for example colloidal gold or latex beads or charcoal or a fluorescent marker.

The strips are generally made up of three zones fixed together on a plastic support: an absorption zone, a reaction zone and a biological sample deposition zone. The strips can also be housed in plastic cassettes. These cassettes facilitate the use of the test and the deposit of the biological sample.

The deposition zone of the biological sample is formed of a cellulose or glass fibre membrane on which the monoclonal antibody of the invention or the fragment of the invention, targeting a first epitope, which is coupled to a tracer (e.g. colloidal gold, latex beads, charcoal or fluorescent marker) and which is not immobilised on said membrane, may be present. Indeed, the latter has physico-chemical characteristics which do not retain the antibody of the invention or the fragment of the invention, targeting a first epitope and coupled to a tracer. Thus, it can migrate along the membrane that constitutes the strip after the addition of the biological sample to be tested.

The reaction zone is formed of a nitrocellulose membrane comprising two lines or strips, one of which is described below as one of the possible and non-limiting ways of creating the said reaction zone. The first of these lines, known as the "test" line, is achieved by immobilising antibodies capable of capturing the BK virus, which may be:
those of the invention or their fragments, targeting a first epitope (i.e. the same as those in the deposit zone); or
those of the invention or their fragments, or even other antibodies, all targeting a second epitope of the VP-1 protein of the capsid of the BK virus (i.e. different from that recognised by the antibody of the invention or the fragment of the invention coupled to a tracer and used at the deposition zone).

It is the signal obtained on this line that indicates the presence or absence of the BK virus, whether or not it is serotype (genotype) Ia, Ib2, II, III and/or IV. The second line, known as the "control" line, consists in most cases of the immobilisation of antibodies directed against the antibodies of the invention (e.g. mouse anti-IgG) or fragments of the invention. The fixation of these proteins on the membrane is carried out by a set of hydrophobic and electrostatic interactions and hydrogen bonds.

The patient's biological sample, once in contact with (or mixed with) the monoclonal antibody of the invention or the fragment of the invention, which is coupled with a tracer (e.g. colloidal gold, latex beads, charcoal or fluorescent marker), migrates along the nitrocellulose membrane by capillarity from the deposition zone and comes into contact with the various immobilised elements described above. The migration of the biological sample is maintained by the absorbent paper at the other end of the strip. These strip tests are therefore simple to use. They are performed either by directly "dipping" the strip into the biological sample or by aspirating a small volume of biological sample with a pipette which is then discharged onto the strip. These tests usually allow a response time of 10-15 minutes. On the nitrocellulose membrane, the results are interpreted by the presence or absence of the strips at the "test" and/or "control" lines following the tracer revelation. These results can be evaluated with the naked eye (e.g. colorimetric plotters) or by using a reader.

In the invention, the presence of strips:
on the "test" line of the test strip means that the antibody/antigen immune complex as described above is detected in the biological sample; and
on the "control" line of the test strip means that the migration has been successful and therefore the test is valid.

Therefore, only the observation of these 2 bands indicates that the test is positive and that the patient from whom the biological sample was taken is infected with the BK virus.

It should be noted that the antibody of the invention or the fragment of the invention in a particular mode of production of the strip is found at the same time:
- on the deposition zone in a non-immobilized manner and coupled with a tracer (e.g. colloidal gold, latex beads, charcoal or fluorescent marker) to form an immune complex with the VP-1 capsid protein of the BK virus present in the biological sample in the event of infection with said BK virus, said immune complex being capable of migrating through the strip; and
- on the "test" line where it is immobilised to bind to the immune complex as described above during migration and retain it.

Figure 7:
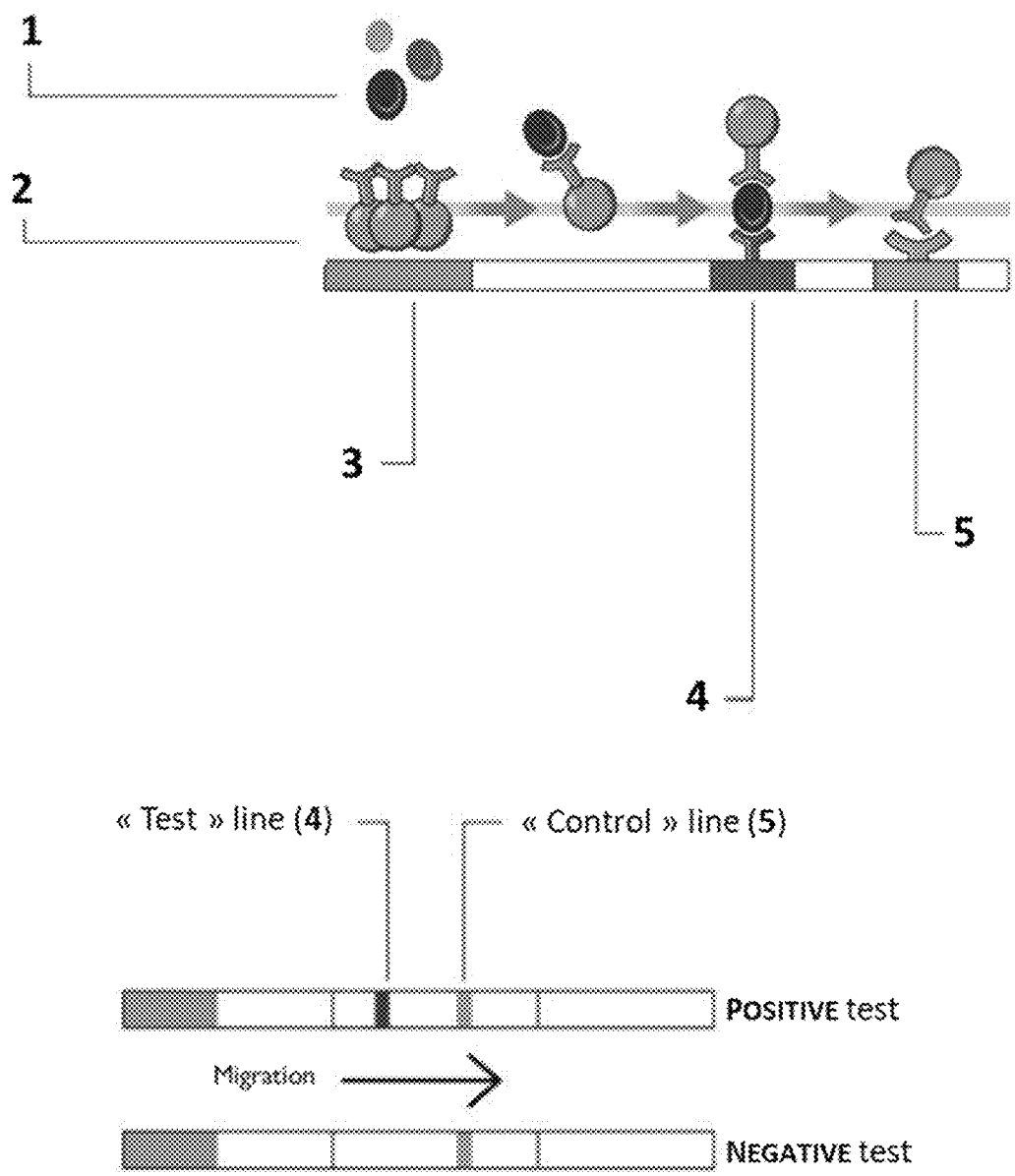
FIG. 7 is a set of diagrams illustrating the operation of strip testing (adapted from G. Prod'hom et al., Rev Med Switzerland 2008; 4: 908-13). The legend used is as follows:
[1] Sample (e.g. blood and/or urine) containing the BK virus;
[2] Antibody (Ac) of the invention directed against a first epitope of the VP-1 protein of the BK virus (antigen, Ag) coupled to a tracer;
[3] Cellulose membrane: Migration of the Ac—Ag mixture by capillary action;
"Test" line: Capture of the Ag by an antibody, e.g. that of the invention directed against the said first epitope or a second epitope of the VP-1 protein of the BK virus;
"Control" line: Capture of excess Ac.

It should also be noted that the patient's biological sample is exposed to an excess of the monoclonal antibody of the invention or fragment of the invention which is coupled to a tracer (e.g. colloidal gold, latex beads, charcoal or fluorescent marker), either by prior mixing with said biological sample, or by the presence of an excess of said monoclonal antibody or fragment coupled to a tracer (e.g. colloidal gold, latex beads, charcoal or fluorescent marker) on the deposition zone. Thus, even if an amount of said monoclonal antibody or tracer-coupled fragment (e.g. colloidal gold, latex beads, charcoal or fluorescent marker) is retained on the test line due to the recognition of the immune complex as described above, due to the excess, an excess amount will continue to migrate within the strip until it reaches the control line, which ensures the proper functioning of the strip and validates the test. For greater precision, the attention of the skilled person is drawn to FIG. 7, which will illustrate this point further without limiting its realization.

In view of the foregoing, a particular embodiment, the invention also concerns the diagnostic kit as described above, the said kit making it possible to detect in a biological sample the said VP-1 protein of the capsid of the BK virus by means of a strip test.

According to another particular embodiment, the invention concerns the diagnostic kit above, wherein said strip comprises at least:
- a deposition zone comprising a cellulose or glass fibre membrane on which is present the monoclonal antibody as described above or a fragment as described above which is
  coupled with a tracer (e.g. colloidal gold, latex beads, charcoal or fluorescent marker);
  capable of recognising a first epitope of the VP-1 protein of the BK virus capsid; and
  capable of migrating along said strip after the biological sample has been added, and
- a reaction zone comprising a nitrocellulose membrane on which is present at least one "test" line on which is immobilised the monoclonal antibody as previously described or a fragment as previously described which is capable of recognising said first epitope or a second epitope of the VP-1 protein of the capsid of the BK virus, or an antibody other than those of the invention and capable of also recognising the protein VP-1 of the capsid of the BK virus;
  and a "control" line on which is immobilised an antibody capable of recognising said monoclonal antibody as described above or a fragment as described above and originating from the deposition zone following migration.

In the invention, the antibodies 'F6', 'H6', '9B1', '14D6' and '18A2' are described. Also, another particular embodiment of the invention concerns the above diagnostic kit, comprising at least one or at least two monoclonal antibodies as described above or at least one or at least two fragments as described above,
in particular said at least one or at least two monoclonal antibodies being selected from the group comprising or consisting of 'F6' (SEQ ID NOs: 20 and 30), 'H6' (SEQ ID NOs: 20 and 40), '9B1' (SEQ ID NOs: 48 and 56), '14D6' (SEQ ID NOs: 60 and 68) and '18A2' (SEQ ID NOs: 72 and 80).

Similarly, it is understood that another particular mode of implementation of the invention relates to an in vitro or ex vivo diagnostic method for detecting a BK virus infection in a patient as described above, said detection step comprising:
- a step of prior mixing of said biological sample with the monoclonal antibody of the invention or the fragment of the invention, said monoclonal antibody or said fragment being coupled to a tracer (e.g. colloidal gold, latex beads, charcoal or fluorescent marker);
- optionally an incubation stage of the said mixture to obtain an incubated mixture;
- a step of deposition of said mixture possibly incubated at one end of a test strip (deposition zone) or a step of dipping one end of a test strip (deposition zone) in said mixture possibly incubated;
- a step of migration by capillarity of said mixture possibly incubated towards the other end of the test strip; and
- a step of observation of the presence or absence of strips at the "test" and "control" lines of the test strip.

It is also understood that another particular embodiment of the invention relates to an in vitro or ex vivo diagnostic method for detecting a BK virus infection in a patient as described above, said detection step comprising:
- a step of depositing said biological sample at one end of a test strip or a step of dipping one end of a test strip into said biological sample, said end being the deposition zone on which the monoclonal antibody of the invention or the fragment of the invention is present, said monoclonal antibody or fragment being coupled to a tracer (e.g. or colloidal, latex beads, charcoal or fluorescent marker);
- a capillary migration step from said biological sample to the other end of the test strip; and
- a step of observation of the presence or absence of strips at the "test" and "control" lines of the test strip.

In the invention, the presence of strips at the "test" line of the test strip and the "control" line of the test strip means respectively that the antibody/antigen immune complex as described above is detected in the biological sample and that migration has taken place, thus validating the test. The test is then positive, indicating that the patient from whom the biological sample was taken is infected with the BK virus.

The following examples will better illustrate the invention, without limiting its scope.

EXAMPLES

Example 1: Generation of VLPs Ib2

The production of VLPs used to generate monoclonal antibodies according to the invention is described in Touzé, A., Bousarghin, L., Ster, C., Combita, A. L., Roingeard, P., & Coursaget, P. (2001). Gene transfer using human polyomavirus BK virus-like particles expressed in insect cells. *The Journal of General Virology*, 82(Pt 12), 3005-9. Briefly, the VP-1 gene from the PA strain belongs to serotype Ib2. Its sequence (SEQ ID NO: 3) has been amplified by PCR by introducing the BclI and HindIII sites in order to clone it into the expression plasmid pFastBac1 (SEQ ID NO: 81) used to generate a recombinant baculovirus encoding the VP-1 protein of the BK polyomavirus. Cells of the lepidopteran *Spodoptera frugiperda* (Sf21) were infected with this baculovirus. The VLPs were purified by a CICs gradient from the nuclei of the infected cells. Transmission electron microscopy (TEM) analysis revealed VLPs (FIG. 1).

Example 2: Generation of BK Virus VLPs Ta, II, III and IV

Figure 2:
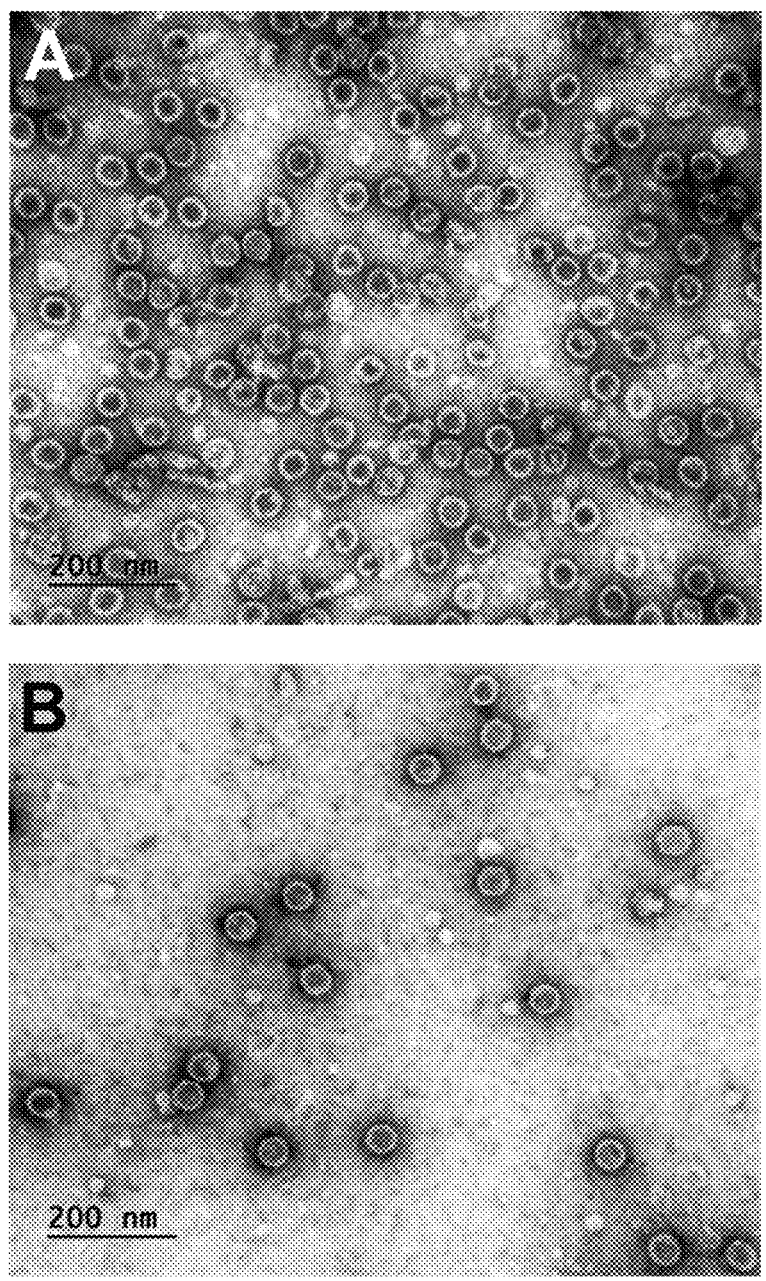
FIG. 2 shows an electron micrograph of VLPs obtained by expression of the BKPyV VP-1 serotype Ia (A) or IV (B) gene in insect cells. The preparation was negatively stained with 5% uranyl acetate and observed at a nominal magnification of ×50,000 with a JEOL 1010 electron microscope.
Bar: 200 nm.
Figure 3:
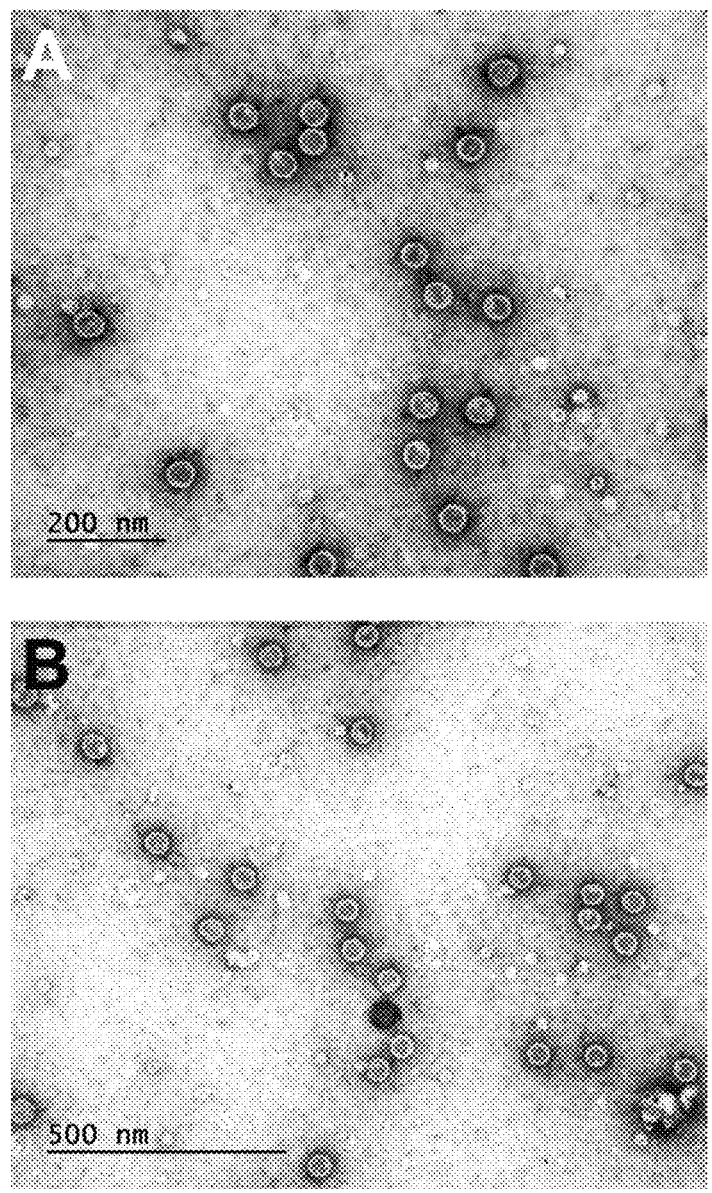
FIG. 3 shows an electron micrograph of VLPs obtained by expression of the BKPyV serotype II VP-1 gene in insect cells. The preparation was negatively stained with 5% uranyl acetate and observed at a nominal magnification of ×50,000 with a JEOL 1010 electron microscope.
Bar: (A) 200 nm and (B) 500 nm.

The VP-1 gene of viruses of serotype Ia (SEQ ID NO: 1), II (SEQ ID NO: 5) and IV (SEQ ID NO: 9) was amplified by PCR by introducing the SalI and HindIII sites from the urine of patients infected with the serotypes of interest and cloned into the insect cell baculovirus system to generate the corresponding VLPs (FIGS. 2 and 3).

Figure 4:
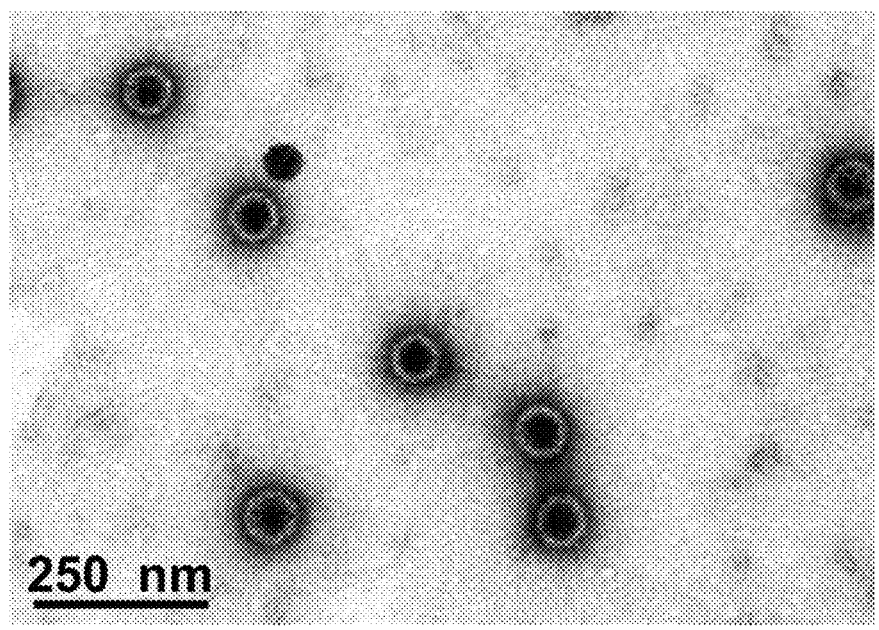
FIG. 4 shows an electron micrograph of VLPs obtained by expression of the BKPyV serotype III VP-1 gene in HEK293T cells. The preparation was negatively stained with 5% uranyl acetate and observed at a nominal magnification of ×50,000 with a JEOL 1010 electron microscope.
Bar: 250 nm.

VP-1 VLPs for serotype III (SEQ ID NO: 7) were obtained by transfecting HEK293T cells (ATCC® CRL-3216™) with the plasmid pIIIw (CB Buck, NCI-NIH; SEQ ID NO: 82). The VLPs were purified as before and observed in ME (FIG. 4).

Example 3: Generation of JC Virus VLPs

Figure 5:
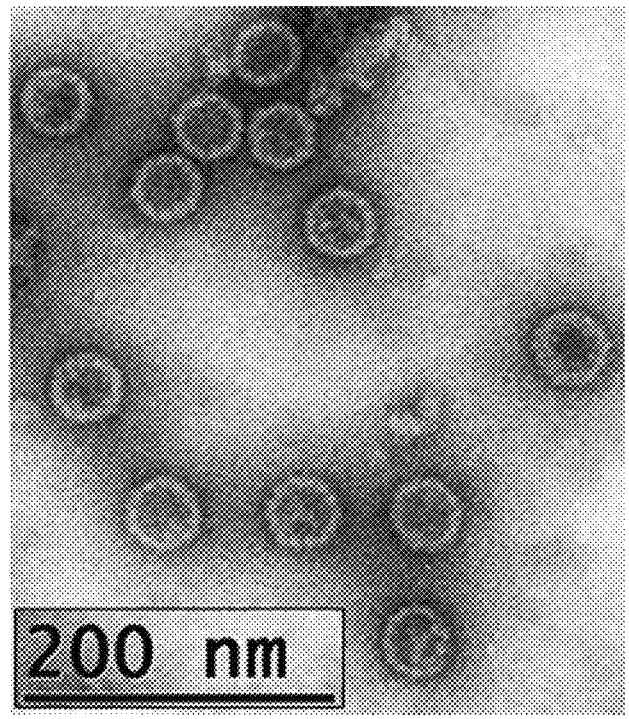
FIG. 5 shows an electron micrograph of VLPs obtained by expression of the JCPyV VP-1 gene in insect cells. The preparation was negatively stained with 5% uranyl acetate and observed at a nominal magnification of ×50,000 with a JEOL 1010 electron microscope.
Bar: 200 nm.

The VP-1 gene of the JC virus (SEQ ID NO: 84) was amplified by PCR by introducing the HindII and SalI sites from the CSF of a subject with progressive multifocal leukoencephalopathy and cloned into the insect cell baculovirus system to generate the corresponding VLPs (FIG. 5).

Example 4: Generation of Monoclonal Antibodies and Study of their Characteristics The monoclonal antibodies according to the invention were generated by immunising Balb/C mice with 10 μg VLPs of polyomavirus BK serotype Ib2 in combination with QuilA (2 μg). Two mice were injected intra-podally with the antigen preparation in a volume of 50 μL/hind leg. The mice were re-immunised with the same preparation 11 days after the first injection. On day 14, the mice were sacrificed and the popliteal lymph nodes were recovered. The lymph nodes were then washed in RPMI and perfused to release lymphocytes. The lymphocytes were then counted and mixed with the myeloma cells (Sp20; ATCC® CRL-1581™) in a ratio of 5:1. After centrifugation, the polyethylene glycol/dimethyl sulfoxide (PEG/DMSO) mixture was added (1 mL in one minute). After addition of RPMI medium enriched with horse serum, OPI (oxaloacetic acid, pyruvate and insulin) and HAT (hypoxanthine, aminopterin and thymidine), the cells were distributed in P24 plate at 10,000 Sp20/well (1 mL). After 15 days of selection (half change of medium 2×/week), the selection was lifted (replacement of TAH by HT (hypoxanthine and thymidine)) and the culture supernatants from the saturation wells were tested for the presence of anti-BK IgG serotype Ib2. After cloning a part of the hybridomas, five hybridomas secreting IgGs recognising the immunogen were produced in two fusions (Tables 1 and 2).

Reactivity of Anti-Bk Monoclonal Antibodies to the Bk Virus

The reactivity of the antibodies produced above was tested by ELISA (enzyme-linked immunosorbent assay). To do this, the VLPs produced were deposited at a concentration of 1 μg/mL in PBS and incubated overnight at +4° C. The wells were then blocked for 1 h at +37° C. with a PBS/FCS (phosphate-buffered saline/fetal calf serum) mixture. After dilution in a dilution buffer containing FCS, PBS and Tween® 20, the various hybridoma culture supernatants were added for 1 h at +37° C. The wells were washed four times in a row with Wash Buffer and a secondary anti-mouse antibody coupled to peroxidase was added to the 1:2000 dilution for 1 h at +37° C. The wells were washed four more times and the substrate (OPD (ortho phenylene diamine)+ $H_2O_2$) was added for 30 min at room temperature. A stop solution ($H_2SO_4$ 4N) was then added and each well was read by measuring the absorbance at 492 nm with a spectrophotometer. The value obtained for the average of the control wells (PBS in the first step) is subtracted from the optical density values obtained for each well.

TABLE 1

Reactivity of 5 of the anti-BK monoclonal antibodies generated

| | VLP | Supernatant Ac Dilution | | | | | | | | | | | |
| --- | --- | --- | --- | --- | --- | --- | --- | --- | --- | --- | --- | --- | --- |
| | | 1/10 | 1/20 | 1/40 | 1/80 | 1/160 | 1/320 | 1/640 | 1/1 280 | 1/2 560 | 1/5 120 | 1/10 240 | 1/20 480 |
| BK6A2F6. | IV | 3.25 | 3.16 | 3.19 | 3.11 | 3.46 | 3.16 | 2.86 | 2.04 | 1.28 | 0.77 | 0.48 | 0.26 |
| | II | 3.00 | 1.65 | 0.90 | 0.44 | 0.27 | 0.16 | 0.14 | 0.09 | 0.07 | 0.07 | 0.08 | 0.10 |
| | IB2 | 2.70 | 1.22 | 1.03 | 0.59 | 0.40 | 0.29 | 0.19 | 0.11 | 0.09 | 0.08 | 0.08 | 0.11 |
| | IA | 3.08 | 3.23 | 3.16 | 3.26 | 3.21 | 3.16 | 3.07 | 2.11 | 1.06 | 0.57 | 0.19 | 0.27 |
| BK4B6G6 | IV | 0.12 | 0.10 | 0.08 | 0.08 | 0.08 | 0.07 | 0.07 | 0.08 | 0.07 | 0.06 | 0.07 | 0.09 |
| | II | 0.09 | 0.06 | 0.06 | 0.06 | 0.07 | 0.06 | 0.07 | 0.06 | 0.07 | 0.07 | 0.07 | 0.09 |
| | IB2 | 3.13 | 3.13 | 3.07 | 2.05 | 1.20 | 0.64 | 0.37 | 0.08 | 0.07 | 0.11 | 0.08 | 0.09 |
| | IA | 0.23 | 0.20 | 0.14 | 0.12 | 0.11 | 0.09 | 0.09 | 0.08 | 0.09 | 0.08 | 0.08 | 0.07 |
| BK6A2AT | IV | 0.13 | 0.11 | 0.08 | 0.08 | 0.07 | 0.06 | 0.06 | 0.06 | 0.06 | 0.05 | 0.05 | 0.05 |
| | II | 0.09 | 0.08 | 0.07 | 0.06 | 0.06 | 0.06 | 0.05 | 0.05 | 0.05 | 0.05 | 0.05 | 0.05 |
| | IB2 | 2.93 | 2.70 | 1.97 | 1.06 | 0.65 | 0.40 | 0.19 | 0.13 | 0.08 | 0.07 | 0.06 | 0.05 |
| | IA | 0.19 | 0.17 | 0.14 | 0.13 | 0.10 | 0.09 | 0.09 | 0.07 | 0.06 | 0.07 | 0.08 | 0.06 |
| BK6A2H6 | IV | 3.29 | 3.21 | 3.38 | 3.14 | 3.14 | 2.66 | 1.59 | 0.91 | 0.54 | 0.26 | 0.17 | 0.12 |
| | II | 2.96 | 0.86 | 0.44 | 0.22 | 0.14 | 0.13 | 0.08 | 0.08 | 0.06 | 0.05 | 0.06 | 0.06 |
| | IB2 | 1.71 | 0.82 | 0.67 | 0.49 | 0.40 | 0.29 | 0.17 | 0.14 | 0.10 | 0.09 | 0.06 | 0.06 |
| | IA | 2.99 | 3.06 | 3.18 | 3.13 | 3.06 | 3.03 | 2.49 | 0.81 | 0.46 | 0.86 | 0.22 | 0.16 |
| BK8G5D6 | IV | 0.17 | 0.10 | 0.08 | 0.09 | 0.06 | 0.08 | 0.07 | 0.07 | 0.08 | 0.08 | 0.11 | 0.11 |
| | II | 0.08 | 0.05 | 0.07 | 0.22 | 0.20 | 0.05 | 0.05 | 0.11 | 0.06 | 0.06 | 0.08 | 0.09 |
| | IB2 | 1.19 | 1.14 | 1.02 | 0.78 | 0.64 | 0.33 | 0.19 | 0.15 | 0.12 | 0.08 | 0.07 | 0.08 |
| | IA | 0.87 | 0.79 | 0.82 | 0.85 | 0.64 | 0.61 | 0.47 | 0.28 | 0.21 | 0.14 | 0.13 | 0.21 |

TABLE 2

Summary of the reactivity of 5 of the anti-BK monoclonal antibodies generated

|     |      | Monoclonal antibody | | | | |
| --- | ---- | --- | --- | --- | --- | --- |
|     |      | BK6A2F6 | BK4B6G6 | BK6A2AT | BK6A2H6 | BK8G5D6 |
| VLP | Ia   | + | − | − | + | + |
|     | Ib-2 | + | + | + | + | + |
|     | II   | + | − | − | + | − |
|     | IV   | + | − | − | + | − |

The antibodies generated by the BK6A2F6 ('F6') and BK6A2H6 ('H6') clones were found to be cross-reactive with all serotynes evaluated (Tables 1 and 2). These two clones were selected and amplified and the antibodies purified by chromatography using a pre-conditioned Protein A column HiTrap™ (Fisher Scientific; GE Healthcare Life Sciences™ HiTrap™ Protein A HP; Cat #10676315, GE Healthcare brand 17-0402-01).

Reactivates Other Anti-Bk Monoclonal Antibodies to the Bk Virus

As other hybridomas were produced in Example 4 (but not tested), it was decided to thaw them and test their reactivity as described above, against the 5 BK polyomavirus serotypes (Table 3). The monoclonal antibodies 'F6' and 'H6' are cross-reactive with these 5 genotypes (or serotypes) and are used as references.

TABLE 3

Cross-reactivity of new antibodies

|  |  | VLP | | | | | |
| --- | --- | --- | --- | --- | --- | --- | --- |
|  |  | Ia | Ib2 | II | III | IV | Background |
| Monoclonal antibody | 'F6' | 3.230 | 2.886 | 1.650 | 0.420 | 3.160 | *0.133* |
|  | 'H6' | 3.060 | 3.185 | 0.860 | 0.481 | 3.210 | *0.130* |
|  | 19B6 | 0.076 | 3.246 | 3.128 | 0.083 | 0.072 | *0.173* |
|  | 9B1 | 3.128 | 3.304 | 1.745 | 1.744 | 2.515 | *0.073* |
|  | 14D6 | 3.237 | 3.237 | 3.079 | 2.549 | 2.615 | *0.107* |
|  | 16B3 | 1.723 | 2.927 | 0.782 | 0.182 | 0.134 | *0.443* |
|  | 18A2 | 2.223 | 3.025 | 1.055 | 0.763 | 1.217 | *0.296* |

Only the antibodies in bold, i.e. 'F6', 'H6' and those derived from hybridomas 9B1 ('9B1'), 14D6 ('14D6') and 18A2 ('18A2'), are capable of recognising the 5 serotypes Ia, Ib2, II, III and IV of the BK virus.

Example 5: Serum Neutralisation

Production and Infection of BKPyV Pseudovirions

The pseudovirions of BKPyV were produced by the techniques described in Pastrana, D. V., Brennan, D. C., Çuburu, N., Storch, G. A., Viscidi, R. P., Randhawa, P. S., & Buck, C. B. (2012). Neutralization Serotyping of BK Polyomavirus Infection in Kidney Transplant Recipients. *PLoS Pathogens*, 8(4), e1002650. Briefly, the VP-1 protein expression plasmids of the respective serotypes, as well as the reporter plasmid pGL4.10 (SEQ ID NO: 83), were co-transfected into HEK293T cells (ATCC® CRL-3216™). Three days after transfection, the cells were lysed and the pseudovirions were matured overnight with 0.1% Ambion® RNase Cocktail™. The pseudovirions were harvested and purified by ultracentrifugation using an iodixanol gradient. To minimise any variation, a single stock of pseudovirions was produced for each serotype, aliquoted and used for all experiments.

Neutralization Test with BKPyV

The BKPyV pseudovirions were mixed either with the various hybridoma supernatants diluted in series, or with a serially diluted positive control or negative control and pre-incubated for 1 h at 4° C., and then added to HEK293T cells (ATCC® CRL-3216™) for 72 h at 37° C. The cells are then lysed and the luciferase measurement is performed on this lysate using a luminometer. Antibodies inducing a decrease in luciferase activity of more than 50% compared to controls are considered neutralising.

TABLE 4

Neutralisation tests with 'F6' antibody

| CELLS | +BKPyV pseudovirions of serotype Ib2 |  | Luciferase activity | 1,189,236 | | |
| --- | --- | --- | --- | --- | --- | --- |
|  | +BKPyV pseudovirions of serotype Ib2 | +neutralising serum (Control+) | Dilution | $1/50^e$ | $1/250^e$ | $1/1\,250^e$ |
|  |  |  | Luciferase activity | 551 | 727 | 1,088 |
|  |  |  | Neutralization (%) | 100 | 100 | 100 |
|  |  | +'F6' | Dilution | $1/10^e$ | $1/500^e$ | $1/2,500^e$ |
|  |  |  | Luciferase activity | 2,087,956 | 1,248,518 | 977,763 |
|  |  |  | Neutralization (%) | 0 | 0 | 18 |

TABLE 5

Neutralisation tests with antibodies 'H6', '9B1', '14D6'.

| CELLS | +BKPyV pseudovirions of serotype Ib2 |  | Luciferase activity | 8,292,738 | |
| --- | --- | --- | --- | --- | --- |
|  | +BKPyV pseudovirions of serotype Ib2 | +'9B1' | Dilution | $1/50^e$ | $1/500^e$ |
|  |  |  | Luciferase activity | 4,598,960 | 6,050,416 |
|  |  |  | Neutralization (%) | 28 | 27 |

TABLE 5-continued

| Neutralisation tests with antibodies 'H6', '9B1', '14D6'. | | | |
|---|---|---|---|
| +'14D6' | Dilution | 1/50$^e$ | 1/500$^e$ |
| | Luciferase activity | 6,209,272 | 7,848,148 |
| | Neutralization (%) | 25 | 5 |
| +'H6' | Dilution | | 1/500$^e$ |
| | Luciferase activity | | 9,662,741 |
| | Neutralization (%) | | 0 |

Despite the presence of 'F6', 'H6', '91B1', '14D6' antibodies, BKPyV pseudoviruses of serotype Ib2 retain their ability to infect cells. Consequently, 'F6', 'H6', '91B1', '14D6' antibodies are not able to neutralise the BKPyV pseudoviruses (Tables 4 and 5).

Example 6: Antibody Isotyping and Sequencing

Materials & Methods

The antibodies secreted by clones BK6A2F6 (F6') and BK6A2H6 (H6') have been isotyped using the Rapid ELISA Mouse mAb Isotyping Kit (Thermo Scientific™; Cat #37503). Briefly, 50 μL of the correctly diluted antibody sample and 50 μL of goat antibody to IgG+IgA+IgM conjugated to HRP (horseradish peroxidase) were added to each well. The plate was homogenised and incubated for 1 h at room temperature. The plate was then washed 3 times with 250 μL Wash Buffer and 75 μL TMB (3,3',5,5'-Tetramethylbenzidine) substrate was added to each well. The reaction was stopped by the addition of 75 μL of Stop Solution and the plate was read using a spectrophotometer at 450 nm.

The antibodies secreted by clones BK6A2F6 ('F6'), BK6A2H6 ('H6'), 9B1 ('9B1'), 14D6 ('14D6') and 18A2 ('18A2') have been sequenced as follows: Total RNA was isolated from hybridoma cells according to the TRIzol© Reagent Technical Manual. The total RNA was then classically retro-transcribed to complementary DNA (cDNA) using either isotype-specific antisense primers or universal primers. Antibody fragments corresponding to the variable regions of the heavy ($V_H$) and light ($V_L$) chains, and constant regions of the heavy ($C_H$) and light ($C_L$) chains were amplified according to the standard operating procedure (SOP) of rapid cDNA endpoint amplification (RACE) known to the skilled person. These amplified antibody fragments were then separately cloned into a standard cloning vector. A colony-based polymerase chain reaction (PCR) was performed to detect the presence of clones with the correct sized inserts. As many as five colonies with correctly sized inserts were sequenced for each fragment. The sequences of the different clones were aligned and the consensus sequence was obtained for each fragment.

Results

The antibodies secreted by clones BK6A2F6 ('F6') and BK6A2H6 ('H6') have been IgG1/kappa isotyped and their sequences are provided in a sequence listing in WIPO ST.25 format filed with this Application (Table 6 below).

The sequences of the antibodies secreted by clones 9B1 ('9B1'), 14D6 ('14D6') and 18A2 ('18A2') are provided in a sequence listing in WIPO ST.25 format filed with this Application (Table 6 below).

TABLE 6

Correspondence between sequence numbers, sequence type and antibodies

| | | 'F6' SEQ ID NO: | | 'H6' SEQ ID NO: | | '9B1' SEQ ID NO: | | '14D6' SEQ ID NO: | | '18A2' SEQ ID NO: | |
|---|---|---|---|---|---|---|---|---|---|---|---|
| | | Nucleic acid | Amino acid | Nucleic acid | Amino acid | Nucleic acid | Amino acid | Nucleic acid | Amino acid | Nucleic acid | Amino acid |
| Heavy chain | CDR1 | 11 | 12 | 11 | 12 | *41* | *42* | *41* | *42* | *41* | *42* |
| | CDR2 | 13 | 14 | 13 | 14 | *43* | *44* | *43* | *44* | *43* | *44* |
| | CDR3 | 15 | 16 | 15 | 16 | 45 | 46 | 57 | 58 | 69 | 70 |
| | Variable region | 17 | 18 | 17 | 18 | 47 | 48 | 59 | 60 | 71 | 72 |
| | Heavy chain | 19 | 20 | 19 | 20 | | | | | | |
| Light chain | CDR1 | 21 | 22 | 31 | 32 | 49 | 50 | 61 | 62 | 73 | 74 |
| | CDR2 | 23 | 24 | 33 | 34 | 51 | 52 | 63 | 64 | 75 | 76 |
| | CDR3 | 25 | 26 | 35 | 36 | 53 | 54 | 65 | 66 | 77 | 78 |
| | Variable region | 27 | 28 | 37 | 38 | 55 | 56 | 67 | 68 | 79 | 80 |
| | Light chain | 29 | 30 | 39 | 40 | | | | | | |

Numbers in bold indicate sequences that are common to 'F6' and 'H6' antibodies, and numbers in italics indicate sequences that are common to '9B1', '14D6' and '18A2' antibodies.

Example 7: Reactivity of Anti-BK Monoclonal Antibodies to the JC Virus

JCPyV VLPs were developed using the same technology as for BK virus (FIG. 5) and the reactivity of 'H6', 'F6', '9B1', '14D6' and '18A2' antibodies to these VLPs was tested as previously described (detection limit: OD>0.5) and compared with that for BK virus serotype Ib2 VLPs (Table 7).

TABLE 7

Reactivity of anti-BK monoclonal antibodies
to the BK and JC viruses

| VLP | Antibodies | | | | |
|---|---|---|---|---|---|
| | 'F6' | 'H6' | '9B1' | '14D6' | '18A2' |
| BK Ib2 | 2.996 | 2.972 | 1.406 | 1.546 | 0.565 |
| JCPyV | 0.028 | 0.013 | 0.119 | 0.112 | 0.116 |

None of the monoclonal antibodies of the invention (i.e. 'F6', 'H6', '9B1', '14D6' and '18A2') are not reactive with JCPyV VLPs (Table 7).

Example 8: Determining the Type of Epitope Recognised and Predicting it (I) Materials & Methods Native or denatured VLPs were deposited at a concentration of 1 µg/mL with PBS and incubated overnight at +4° C. The denatured VLPs were obtained by treatment with 0.1 M carbonate buffer (pH 10.6) and 0.01 M dithiothreitol (DTT) in PBS for 30 minutes at 37° C.

The wells were then blocked for 1 hour at +37° C. with a PBS/SVF mixture. After dilution in a dilution buffer containing SVF, PBS and Tween® 20, the individual culture supernatants or purified antibodies were added for 1 hour at +37° C. The wells were washed four times in a row with Wash Buffer and a secondary anti-mouse peroxidase antibody was added to the 1/2000 dilution for 1 hour at +37° C. The wells were washed again four times in a row and the substrate was added for 30 minutes at room temperature. A stop solution was added and then each well was read by measuring the absorbance at 492 nm with a spectrophotometer. The value obtained for the average of the control wells (PBS in the first step) was subtracted from the optical density values obtained for each well (detection threshold: OD>0.5).

Results

TABLE 8

Reactivity of the 4 anti-BK monoclonal antibodies 'F6', '9B1', '14D6' and '18A2' to native (undenatured) or denatured VLPs

| | 'F6' | | '9B1' | | '14D6' | | '18A2' | |
|---|---|---|---|---|---|---|---|---|
| Antibodies VLPs | not denatured | denatured | not denatured | denatured | not denatured | denatured | not denatured | denatured |
| Ia | 3.936 | 0.41 | 4.211 | 0.41 | 4.04 | 0.467 | 3.844 | 3.975 |
| Ib2 | 2.70 | 0.163 | 1.406 | 0.167 | 1.546 | 0.126 | 0.565 | 0.16 |
| II | 3.00 | 0.275 | 1.069 | 0.463 | 1.659 | 0.402 | 1.709 | 0.63 |
| IV | 0.788 | 0.149 | 2.125 | 0.184 | 2.633 | 0.191 | 2.994 | 0.709 |

The 'F6', '9B1' and '14D6' antibodies recognise VLPs only when they are in their native state, i.e. in a state where the VP-1 protein has its three-dimensional folding (Table 8). This means that these 3 antibodies target a conformational epitope, which only exists if the VP-1 protein is correctly folded. By extension, the 'H6' antibody, which shares its heavy chain with the 'F6' antibody, also recognises a conformational epitope of the VP-1 protein of the BK virus capsid.

The '18A2' antibody has the ability to recognise VLPs in both native and linearised states (Table 8). This particular antibody therefore targets a linear epitope of the VP-1 protein of the BK virus capsid.

(II) Materials & Methods

The VLPs (BKV VP-1, serotype Ia) were denatured in Laemmli buffer at 95° C. for 5 min, then the samples were loaded into SDS-PAGE gels and transferred to membranes (Millipore®). The membranes were blocked for one hour at room temperature in PBS-Tween®-milk and then the primary anti-BK antibodies were incubated overnight at +4° C. For detection, peroxidase-conjugated secondary anti-mouse antibodies were added for one hour at room temperature. Revelation was carried out using the ECL® substrate (Pierce®).

Results

Figure 6:
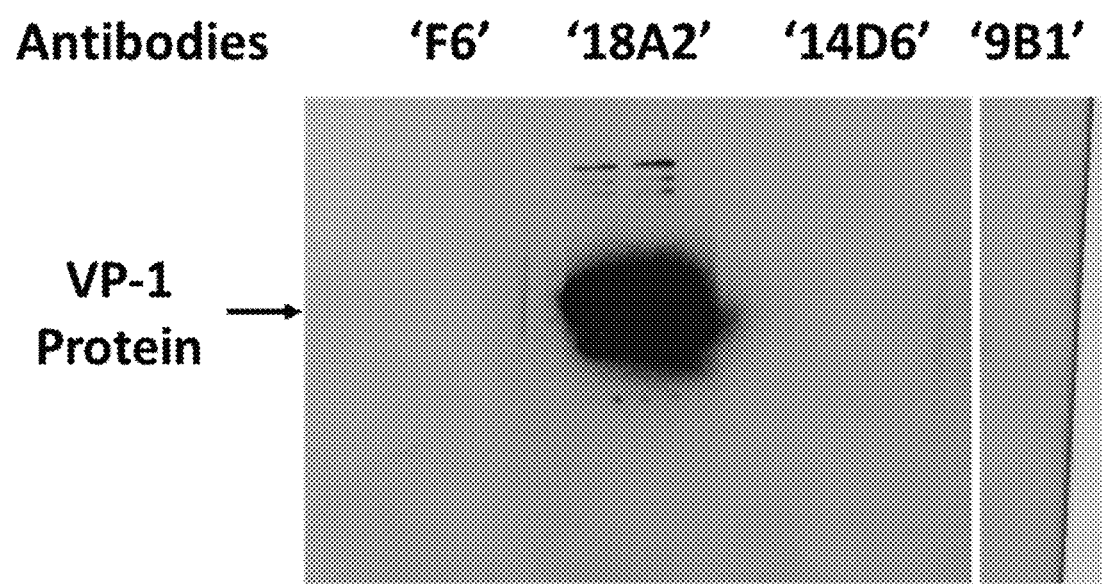
FIG. 6 shows a photograph of the photo film revealed following the Western Blot in Example 7. Following the denaturation of the VLPs, the VP-1 protein of the BK virus capsid is only recognised by the '18A2' antibody.

Following denaturation of the VLPs, which involves linearisation of the VP-1 protein of the BK virus capsid, only the '18A2' antibody gives a signal following the Western blot (FIG. 6).

The '18A2' antibody, unlike the 'F6', '9B1' and '14D6' antibodies, is therefore able to target the linearised VP-1 protein, i.e. it does not show any three-dimensional folding.

These results therefore confirm those obtained by ELISA (Table 7): the 'F6', 'H6', '9B1' and '14D6' antibodies target a conformational epitope of the VP-1 protein of the BK virus capsid, while the '18A2' antibody targets a linear epitope.

(III) Materials & Methods

The prediction of the conformational epitope recognised by the 'F6', 'H6', '9B1' and '14D6' antibodies was carried out by MabSilico SAS using the MAbTope method, which consists of the computer prediction of a list of amino acids likely to belong to the epitope. To this end, a computer model was constructed from the three-dimensional 4MJ0 model of the VP-1 protein and the sequence of the variable part of the 'F6', 'H6', '9B1' and '14D6' antibodies. This model was used to model the epitope of the VP-1 protein:

of serotype Ib from the fragment of sequence SEQ ID NO: 86, which corresponds to amino acids 34 to 298 of sequence SEQ ID NO: 4;

II from the fragment of sequence SEQ ID NO: 87, which corresponds to amino acids 34 to 298 of SEQ ID NO: 6;

III from the fragment of sequence SEQ ID NO: 88, which corresponds to amino acids 34 to 298 of sequence SEQ ID NO: 8; and IV from the fragment of sequence SEQ ID NO: 89, which corresponds to amino acids 34 to 298 of sequence SEQ ID NO: 10, recognised by each of the 'F6', 'H6', '9B1' and '14D6' antibodies.

In addition and from the sequence of the VP-1 protein of serotype Ib2 (SEQ ID NO: 91), the mutants of sequence:

SEQ ID NO: 92 (R93E);

SEQ ID NO: 93 (T192A D193K);

SEQ ID NO: 94 (D199N K200N N201A N202A);

SEQ ID NO: 95 (E73_S77del);

SEQ ID NO: 96 (S71_D82del);

SEQ ID NO: 97 (K135A E138A H139A);

SEQ ID NO: 98 (K135_H139del);

SEQ ID NO: 99 (S274A S275A);

SEQ ID NO: 100 (S274_T277del);

SEQ ID NO: 101 (R83A K84A); and
SEQ ID NO: 102 (R83_L86del),
are expressed to observe the absence of antibody reactivity, thus confirming the predictions of the MAbTope method.

Results

The predictions of the epitopes recognised by the 'F6', 'H6', '9B1' and '14D6' antibodies are shown in FIGS. 8 to 11 respectively.

The invention claimed is:

1. A monoclonal antibody directed against VP-1 protein of capsid of BK virus, said VP-1 protein being represented by a sequence having at least 90% of identity with the sequence of SEQ ID NO: 4,
said monoclonal antibody being capable of recognizing at least all serotypes Ia, Ib2, II, III and IV of said VP-1 protein of said BK virus,
said monoclonal antibody not being able to recognise JC virus,
wherein said monoclonal antibody comprising:
a heavy chain comprising from its N-terminal end to its C-terminal end:
  a CDR1 having the sequence of SEQ ID NO: 12;
  a CDR2 having the sequence of SEQ ID NO: 14; and
  a CDR3 having the sequence of SEQ ID NO: 16;
and
a light chain comprising from its N-terminal end to its C-terminal end:
  a CDR1 having the sequence of SEQ ID NO: 22;
  a CDR2 having the sequence of SEQ ID NO: 24; and
  a CDR3 having the sequence of SEQ ID NO: 26;
or
a heavy chain comprising from its N-terminal end to its C-terminal end:
  a CDR1 having the sequence of SEQ ID NO: 12;
  a CDR2 having the sequence of SEQ ID NO: 14; and
  a CDR3 having the sequence of SEQ ID NO: 16;
and
a light chain comprising from its N-terminal end to its C-terminal end:
  a CDR1 having the sequence of SEQ ID NO: 32;
  a CDR2 having the sequence of SEQ ID NO: 34; and
  a CDR3 having the sequence of SEQ ID NO: 36;
or
a heavy chain comprising from its N-terminal end to its C-terminal end:
  a CDR1 having the sequence of SEQ ID NO: 42;
  a CDR2 having the sequence of SEQ ID NO: 44; and
  a CDR3 having the sequence of SEQ ID NO: 46;
and
a light chain comprising from its N-terminal end to its C-terminal end:
  a CDR1 having the sequence of SEQ ID NO: 50;
  a CDR2 having the sequence of SEQ ID NO: 52; and
  a CDR3 having the sequence of SEQ ID NO: 54;
or
a heavy chain comprising from its N-terminal end to its C-terminal end:
  a CDR1 having the sequence of SEQ ID NO: 42;
  a CDR2 having the sequence of SEQ ID NO: 44; and
  a CDR3 having the sequence of SEQ ID NO: 58;
and
a light chain comprising from its N-terminal end to its C-terminal end:
  a CDR1 having the sequence of SEQ ID NO: 62;
  a CDR2 having the sequence of SEQ ID NO: 64; and
  a CDR3 having the sequence of SEQ ID NO: 66;
or
a heavy chain comprising from its N-terminal end to its C-terminal end:
  a CDR1 having the sequence of SEQ ID NO: 42;
  a CDR2 having the sequence of SEQ ID NO: 44; and
  a CDR3 having the sequence of SEQ ID NO: 70;
and
a light chain comprising from its N-terminal end to its C-terminal end:
  a CDR1 having the sequence of SEQ ID NO: 74;
  a CDR2 having the sequence of SEQ ID NO: 76; and
  a CDR3 having the sequence of SEQ ID NO: 78.

2. The monoclonal antibody according to claim 1, comprising:
a heavy chain comprising from its N-terminal end to its C-terminal end:
  the CDR1 having the sequence of SEQ ID NO: 12;
  the CDR2 having the sequence of SEQ ID NO: 14; and
  the CDR3 having the sequence of SEQ ID NO: 16;
and
a light chain comprising from its N-terminal end to its C-terminal end:
  the CDR1 having the sequence of SEQ ID NO: 22;
  the CDR2 having the sequence of SEQ ID NO: 24; and
  the CDR3 having the sequence of SEQ ID NO: 26.

3. The monoclonal antibody according to claim 2, comprising:
a heavy chain variable region having at least 80% identity with the sequence of SEQ ID NO: 18; and
a light chain variable region having at least 80% identity with the sequence of SEQ ID NO: 28.

4. The monoclonal antibody according to claim 2, comprising:
a heavy chain comprising or consisting of a sequence having at least 80% identity with the sequence of SEQ ID NO: 20, said heavy chain comprising a variable region having at least 80% identity with the sequence of SEQ ID NO: 18; and
a light chain comprising or consisting of a sequence having at least 80% identity with the sequence of SEQ ID NO: 30, said light chain comprising a variable region having at least 80% identity with the sequence of SEQ ID NO: 28.

5. The monoclonal antibody according to claim 1, comprising:
a heavy chain comprising from its N-terminal end to its C-terminal end:
the CDR1 having the sequence of SEQ ID NO: 12;
the CDR2 having the sequence of SEQ ID NO: 14; and
the CDR3 having the sequence of SEQ ID NO: 16;
and
a light chain comprising from its N-terminal end to its C-terminal end:
the CDR1 having the sequence of SEQ ID NO: 32;
the CDR2 having the sequence of SEQ ID NO: 34; and
the CDR3 having the sequence of SEQ ID NO: 36.

6. The monoclonal antibody according to claim 5, comprising:
a heavy chain variable region having at least 80% identity with the sequence of SEQ ID NO: 18; and
a light chain variable region having at least 80% identity with the sequence of SEQ ID NO: 38.

7. The monoclonal antibody according to claim 5, comprising:
a heavy chain comprising or consisting of a sequence having at least 80% identity with the sequence of SEQ ID NO: 20, said heavy chain comprising a variable region having at least 80% identity with the sequence of SEQ ID NO: 18; and
a light chain comprising or consisting of a sequence having at least 80% identity with the sequence of SEQ ID NO: 40, said light chain comprising a variable region having at least 80% identity with the sequence of SEQ ID NO: 38.

8. The monoclonal antibody according to claim 1, comprising:
a heavy chain comprising from its N-terminal end to its C-terminal end:
the CDR1 having the sequence of SEQ ID NO: 42;
the CDR2 having the sequence of SEQ ID NO: 44; and
the CDR3 having the sequence of SEQ ID NO: 46;
and
a light chain comprising from its N-terminal end to its C-terminal end:
the CDR1 having the sequence of SEQ ID NO: 50;
the CDR2 having the sequence of SEQ ID NO: 52; and
the CDR3 having the sequence of SEQ ID NO: 54.

9. The monoclonal antibody according to claim 8, comprising:
a heavy chain variable region having at least 80% identity with the sequence of SEQ ID NO: 48; and
a light chain variable region having at least 80% identity with the sequence of SEQ ID NO: 56.

10. The monoclonal antibody according to claim 1, comprising:
a heavy chain comprising from its N-terminal end to its C-terminal end:
the CDR1 having the sequence of SEQ ID NO: 42;
the CDR2 having the sequence of SEQ ID NO: 44; and
the CDR3 having the sequence of SEQ ID NO: 58;
and
a light chain comprising from its N-terminal end to its C-terminal end:
the CDR1 having the sequence of SEQ ID NO: 62;
the CDR2 having the sequence of SEQ ID NO: 64; and
the CDR3 having the sequence of SEQ ID NO: 66.

11. The monoclonal antibody according to claim 10, comprising:
a heavy chain variable region having at least 80% identity with the sequence of SEQ ID NO: 60; and
a light chain variable region having at least 80% identity with the sequence of SEQ ID NO: 68.

12. The monoclonal antibody according to claim 1, comprising:
a heavy chain comprising from its N-terminal end to its C-terminal end:
the CDR1 having the sequence of SEQ ID NO: 42;
the CDR2 having the sequence of SEQ ID NO: 44; and
the CDR3 having the sequence of SEQ ID NO: 70;
and
a light chain comprising from its N-terminal end to its C-terminal end:
the CDR1 having the sequence of SEQ ID NO: 74;
the CDR2 having the sequence of SEQ ID NO: 76; and
the CDR3 having the sequence of SEQ ID NO: 78.

13. The monoclonal antibody according to claim 12, comprising:
a heavy chain variable region having at least 80% identity with the sequence of SEQ ID NO: 72; and
a light chain variable region having at least 80% identity with the sequence of SEQ ID NO: 80.

14. The monoclonal antibody according to claim 1, comprising:
a heavy chain comprising or consisting of the sequence of SEQ ID NO: 20; and
a light chain comprising or consisting of the sequence of SEQ ID NO: 30,
or
a heavy chain comprising or consisting of the sequence of SEQ ID NO: 20; and
a light chain comprising or consisting of the sequence of SEQ ID NO: 40,
or
a heavy chain comprising a variable region of sequence SEQ ID NO: 48; and
a light chain comprising a variable region of sequence SEQ ID NO: 56,
or
a heavy chain comprising a variable region of sequence SEQ ID NO: 60; and
a light chain comprising a variable region of sequence SEQ ID NO: 68,
or
a heavy chain comprising a variable region of sequence SEQ ID NO: 72; and
a light chain comprising a variable region of sequence SEQ ID NO: 80.

15. A fragment of a monoclonal antibody according to claim 1, said fragment being selected from the group consisting of: Fv, Fab, F(ab')$_2$, Fab', dsFv, scFv, sc (Fv)$_2$, and diabodies.

16. An in vitro or ex vivo diagnostic method for detecting a BK virus infection in a patient comprising the steps of:
   (i) contacting a biological sample from the patient with the monoclonal antibody according to claim 1 or a fragment of said monoclonal antibody, said fragment being selected from the group consisting of: Fv, Fab, F(ab')$_2$, Fab', dsFv, scFv, sc (Fv)$_2$, and diabodies; and
   (ii) detecting an antibody/antigen immune complex in the biological sample.

* * * * *

SEQUENCE LISTING

```
<160> NUMBER OF SEQ ID NOS: 102

<210> SEQ ID NO 1
<211> LENGTH: 1089
<212> TYPE: DNA
<213> ORGANISM: BK virus
<220> FEATURE:
<221> NAME/KEY: CDS
<222> LOCATION: (1)..(1089)
<223> OTHER INFORMATION: VP-1 gene, serotype Ia

<400> SEQUENCE: 1 atg gcc cca acc aaa aga aag gga gag tgt cca ggg gca gct ccc aaa       48
Met Ala Pro Thr Lys Arg Lys Gly Glu Cys Pro Gly Ala Ala Pro Lys
1               5                   10                  15 aag cca aag gaa ccc gtg caa gtg cca aaa cta cta ata aaa gga gga       96
Lys Pro Lys Glu Pro Val Gln Val Pro Lys Leu Leu Ile Lys Gly Gly
            20                  25                  30 gta gaa gtt cta gaa gtt aaa act ggg gta gat gct att aca gag gta      144
Val Glu Val Leu Glu Val Lys Thr Gly Val Asp Ala Ile Thr Glu Val
        35                  40                  45 gaa tgc ttc cta aac cca gaa atg ggg gat cca gat gaa aac ctt agg      192
Glu Cys Phe Leu Asn Pro Glu Met Gly Asp Pro Asp Glu Asn Leu Arg
    50                  55                  60 ggc ttt agt cta aag cta agt gtt caa aat gac ttt agc agt gat agc      240
Gly Phe Ser Leu Lys Leu Ser Val Gln Asn Asp Phe Ser Ser Asp Ser
65                  70                  75                  80 cca cag aga aaa atg ctt ccc tgt tac agc aca gca aga att ccc ctg      288
Pro Gln Arg Lys Met Leu Pro Cys Tyr Ser Thr Ala Arg Ile Pro Leu
                85                  90                  95 ccc aat tta aat gag gac cta acc tgt gga aat cta ctg atg tgg gag      336
Pro Asn Leu Asn Glu Asp Leu Thr Cys Gly Asn Leu Leu Met Trp Glu
            100                 105                 110 gct gta act gta caa aca gag gtt att gga ata act agc atg ctt aac      384
Ala Val Thr Val Gln Thr Glu Val Ile Gly Ile Thr Ser Met Leu Asn
        115                 120                 125 ctt cat gca ggg tca caa aaa gtg cat gag aat ggt gga gga aaa cct      432
Leu His Ala Gly Ser Gln Lys Val His Glu Asn Gly Gly Gly Lys Pro
    130                 135                 140 att caa ggc agt aat ttc cac ttc ttt gct gtt ggt gga gac ccc ttg      480
Ile Gln Gly Ser Asn Phe His Phe Phe Ala Val Gly Gly Asp Pro Leu
145                 150                 155                 160 gaa atg cag gga gtg cta atg aat tac aag aca aag tac cca gat ggt      528
Glu Met Gln Gly Val Leu Met Asn Tyr Lys Thr Lys Tyr Pro Asp Gly
                165                 170                 175 act gta acc cct aaa aac cca aca gcc cag tcc cag gta atg aat act      576
Thr Val Thr Pro Lys Asn Pro Thr Ala Gln Ser Gln Val Met Asn Thr
            180                 185                 190 gac cat aag gcc tat ttg gac aaa aac aat gct tat cca gtt gag tgc      624
Asp His Lys Ala Tyr Leu Asp Lys Asn Asn Ala Tyr Pro Val Glu Cys
        195                 200                 205 tgg gtt cct gat ccc agt aga aat gaa aat act agg tat ttt ggg act      672
Trp Val Pro Asp Pro Ser Arg Asn Glu Asn Thr Arg Tyr Phe Gly Thr
    210                 215                 220
```

| | | | | | | | | | | | | | | | | |
|---|---|---|---|---|---|---|---|---|---|---|---|---|---|---|---|---|
| ttc | aca | gga | ggg | gaa | aat | gtt | ccc | cca | gta | ctt | cat | gtg | acc | aac | aca | 720 |
| Phe | Thr | Gly | Gly | Glu | Asn | Val | Pro | Pro | Val | Leu | His | Val | Thr | Asn | Thr | |
| 225 | | | | 230 | | | | | 235 | | | | 240 | | | |
| gct | acc | aca | gtg | ttg | cta | gat | gaa | cag | ggt | gtg | ggg | ccc | ctt | tgt | aaa | 768 |
| Ala | Thr | Thr | Val | Leu | Leu | Asp | Glu | Gln | Gly | Val | Gly | Pro | Leu | Cys | Lys | |
| | | | | 245 | | | | | 250 | | | | | 255 | | |
| gct | gat | agc | ctg | tat | gtt | tca | gct | gct | gat | att | tgt | ggc | ctg | ttt | act | 816 |
| Ala | Asp | Ser | Leu | Tyr | Val | Ser | Ala | Ala | Asp | Ile | Cys | Gly | Leu | Phe | Thr | |
| | | | 260 | | | | | 265 | | | | | 270 | | | |
| aac | agc | tct | gga | aca | caa | cag | tgg | aga | ggc | ctt | gca | aga | tat | ttt | aag | 864 |
| Asn | Ser | Ser | Gly | Thr | Gln | Gln | Trp | Arg | Gly | Leu | Ala | Arg | Tyr | Phe | Lys | |
| | | 275 | | | | | 280 | | | | | 285 | | | | |
| atc | cgc | ctg | aga | aaa | aga | tct | gta | aag | aat | cct | tac | cca | att | tcc | ttt | 912 |
| Ile | Arg | Leu | Arg | Lys | Arg | Ser | Val | Lys | Asn | Pro | Tyr | Pro | Ile | Ser | Phe | |
| | 290 | | | | | 295 | | | | | 300 | | | | | |
| ttg | cta | agt | gac | ctt | ata | aac | agg | aga | acc | cag | aga | gtg | gat | ggg | cag | 960 |
| Leu | Leu | Ser | Asp | Leu | Ile | Asn | Arg | Arg | Thr | Gln | Arg | Val | Asp | Gly | Gln | |
| 305 | | | | 310 | | | | | 315 | | | | | 320 | | |
| cct | atg | tat | ggt | atg | gaa | tcc | cag | gta | gag | gag | gtt | agg | gtg | ttt | gat | 1008 |
| Pro | Met | Tyr | Gly | Met | Glu | Ser | Gln | Val | Glu | Glu | Val | Arg | Val | Phe | Asp | |
| | | | | 325 | | | | | 330 | | | | | 335 | | |
| ggc | aca | gaa | aga | ctt | cca | ggg | gac | cca | gat | atg | ata | aga | tat | att | gac | 1056 |
| Gly | Thr | Glu | Arg | Leu | Pro | Gly | Asp | Pro | Asp | Met | Ile | Arg | Tyr | Ile | Asp | |
| | | 340 | | | | | 345 | | | | | 350 | | | | |
| aaa | cag | gga | caa | ttg | caa | aca | aaa | atg | gtt | taa | | | | | | 1089 |
| Lys | Gln | Gly | Gln | Leu | Gln | Thr | Lys | Met | Val | | | | | | | |
| | | 355 | | | | | 360 | | | | | | | | | |

<210> SEQ ID NO 2
<211> LENGTH: 362
<212> TYPE: PRT
<213> ORGANISM: BK virus

<400> SEQUENCE: 2

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Val Gln Asn Asp Phe Ser Ser Asp Ser
65                  70                  75                  80

Pro Gln Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu Asn Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Lys Thr Lys Tyr Pro Asp Gly
                165                 170                 175

Thr Val Thr Pro Lys Asn Pro Thr Ala Gln Ser Gln Val Met Asn Thr
            180                 185                 190

-continued

```
Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Val
        355                 360
```

<210> SEQ ID NO 3
<211> LENGTH: 1089
<212> TYPE: DNA
<213> ORGANISM: BK virus
<220> FEATURE:
<221> NAME/KEY: CDS
<222> LOCATION: (1)..(1089)
<223> OTHER INFORMATION: VP-1 gene, serotype Ib2

<400> SEQUENCE: 3

```
atg gcc cca acc aaa aga aaa gga gag tgt cca ggg gca gct ccc aaa      48
Met Ala Pro Thr Lys Arg Lys Gly Glu Cys Pro Gly Ala Ala Pro Lys
1               5                   10                  15 aag cca aag gaa ccc gtg caa gtg cca aaa ctg cta ata aaa gga gga      96
Lys Pro Lys Glu Pro Val Gln Val Pro Lys Leu Leu Ile Lys Gly Gly
            20                  25                  30 gta gaa gtt cta gaa gtt aaa act ggg cta gat gct ata aca gag gta     144
Val Glu Val Leu Glu Val Lys Thr Gly Leu Asp Ala Ile Thr Glu Val
        35                  40                  45 gaa tgc ttc cta aac cca gaa atg ggg gat cca aat gaa aac ctt agg     192
Glu Cys Phe Leu Asn Pro Glu Met Gly Asp Pro Asn Glu Asn Leu Arg
    50                  55                  60 ggc ttt agt cta aag cta agt gct gaa aat gac ttt agc agt gat agc     240
Gly Phe Ser Leu Lys Leu Ser Ala Glu Asn Asp Phe Ser Ser Asp Ser
65                  70                  75                  80 cca gaa aga aaa atg ctt ccc tgt tac agc aca gca aga att ccc ctc     288
Pro Glu Arg Lys Met Leu Pro Cys Tyr Ser Thr Ala Arg Ile Pro Leu
                85                  90                  95 ccc aat tta aat gag gac cta acc tgt gga aat cta ctg atg tgg gag     336
Pro Asn Leu Asn Glu Asp Leu Thr Cys Gly Asn Leu Leu Met Trp Glu
            100                 105                 110 gct gta aca gta caa aca gag gtc att gga ata act agc atg ctt aac     384
Ala Val Thr Val Gln Thr Glu Val Ile Gly Ile Thr Ser Met Leu Asn
        115                 120                 125 ctt cat gca ggg tca caa aaa gtg cat gag cat ggt gga ggt aaa cct     432
```

-continued

| | | |
|---|---|---|
| Leu His Ala Gly Ser Gln Lys Val His Glu His Gly Gly Lys Pro<br>130                         135                        140 | | |
| att caa ggc agt aat ttc cac ttt ttt gct gtt ggt gga gac ccc ttg<br>Ile Gln Gly Ser Asn Phe His Phe Phe Ala Val Gly Gly Asp Pro Leu<br>145                       150                     155                   160 | | 480 |
| gaa atg cag gga gtg cta atg aat tac agg aca aag tac cca gaa ggt<br>Glu Met Gln Gly Val Leu Met Asn Tyr Arg Thr Lys Tyr Pro Glu Gly<br>                     165                     170                   175 | | 528 |
| act ata acc cca aaa aac cca aca gcc cag tcc cag gta atg aat act<br>Thr Ile Thr Pro Lys Asn Pro Thr Ala Gln Ser Gln Val Met Asn Thr<br>180                       185                     190 | | 576 |
| gac cat aag gcc tat ttg gac aaa aac aat gct tat cca gtt gag tgc<br>Asp His Lys Ala Tyr Leu Asp Lys Asn Asn Ala Tyr Pro Val Glu Cys<br>                   195                   200                   205 | | 624 |
| tgg att cct gat ccc agt aga aat gaa aat act agg tat ttt ggg act<br>Trp Ile Pro Asp Pro Ser Arg Asn Glu Asn Thr Arg Tyr Phe Gly Thr<br>210                       215                     220 | | 672 |
| ttc aca gga ggg gaa aat gtt ccc cca gta ctt cat gtg acc aac aca<br>Phe Thr Gly Gly Glu Asn Val Pro Pro Val Leu His Val Thr Asn Thr<br>225                       230                     235                   240 | | 720 |
| gct acc aca gtg ttg cta gat gaa cag ggt gtg ggg cct ctt tgt aaa<br>Ala Thr Thr Val Leu Leu Asp Glu Gln Gly Val Gly Pro Leu Cys Lys<br>                   245                   250                   255 | | 768 |
| gct gat agc ctg tat gtt tca gct gct gat att tgt ggc ctg ttt act<br>Ala Asp Ser Leu Tyr Val Ser Ala Ala Asp Ile Cys Gly Leu Phe Thr<br>260                       265                     270 | | 816 |
| aac agc tct gga aca caa cag tgg aga ggc ctt gca aga tat ttt aag<br>Asn Ser Ser Gly Thr Gln Gln Trp Arg Gly Leu Ala Arg Tyr Phe Lys<br>                   275                   280                   285 | | 864 |
| att cgc ctg aga aaa aga tct gta aaa aat cct tac cca att tcc ttt<br>Ile Arg Leu Arg Lys Arg Ser Val Lys Asn Pro Tyr Pro Ile Ser Phe<br>290                       295                     300 | | 912 |
| ttg cta agt gac ctt ata aac agg aga acc cag aga gtg gat ggg cag<br>Leu Leu Ser Asp Leu Ile Asn Arg Arg Thr Gln Arg Val Asp Gly Gln<br>305                       310                     315                   320 | | 960 |
| cct atg tat ggt atg gaa tcc cag gta gaa gag gtt agg gtg ttt gat<br>Pro Met Tyr Gly Met Glu Ser Gln Val Glu Glu Val Arg Val Phe Asp<br>                   325                   330                   335 | | 1008 |
| ggc aca gaa aaa ctt cca ggg gac cca gat atg ata aga tat att gac<br>Gly Thr Glu Lys Leu Pro Gly Asp Pro Asp Met Ile Arg Tyr Ile Asp<br>340                       345                     350 | | 1056 |
| aaa caa gga caa ttg caa acc aaa atg ctt taa<br>Lys Gln Gly Gln Leu Gln Thr Lys Met Leu<br>                   355                   360 | | 1089 |

<210> SEQ ID NO 4
<211> LENGTH: 362
<212> TYPE: PRT
<213> ORGANISM: BK virus

<400> SEQUENCE: 4

Met Ala Pro Thr Lys Arg Lys Gly Glu Cys Pro Gly Ala Ala Pro Lys
1               5                   10                   15

Lys Pro Lys Glu Pro Val Gln Val Pro Lys Leu Leu Ile Lys Gly Gly
                  20                   25                   30

Val Glu Val Leu Glu Val Lys Thr Gly Leu Asp Ala Ile Thr Glu Val
                 35                   40                   45

Glu Cys Phe Leu Asn Pro Glu Met Gly Asp Pro Asn Glu Asn Leu Arg
50                       55                   60

-continued

```
Gly Phe Ser Leu Lys Leu Ser Ala Glu Asn Asp Phe Ser Ser Asp Ser
 65                  70                  75                  80

Pro Glu Arg Lys Met Leu Pro Cys Tyr Ser Thr Ala Arg Ile Pro Leu
                 85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360

<210> SEQ ID NO 5
<211> LENGTH: 1089
<212> TYPE: DNA
<213> ORGANISM: BK virus
<220> FEATURE:
<221> NAME/KEY: CDS
<222> LOCATION: (1)..(1089)
<223> OTHER INFORMATION: VP-1 gene, serotype II

<400> SEQUENCE: 5 atg gcc cca acc aaa aga aag gga gag tgt cca ggg gca gct ccc aga      48
Met Ala Pro Thr Lys Arg Lys Gly Glu Cys Pro Gly Ala Ala Pro Arg
 1               5                  10                  15 aag cca aag gaa ccc gtg caa gtg cca aaa cta cta ata aaa gga gga      96
Lys Pro Lys Glu Pro Val Gln Val Pro Lys Leu Leu Ile Lys Gly Gly
             20                  25                  30 gta gaa gtt cta gaa gtt aaa act ggg gta gat gct ata aca gag gta     144
Val Glu Val Leu Glu Val Lys Thr Gly Val Asp Ala Ile Thr Glu Val
```

```
                    35                  40                  45
gaa tgc ttt cta aac cca gaa atg ggg gat cca gat gat aac ctt agg        192
Glu Cys Phe Leu Asn Pro Glu Met Gly Asp Pro Asp Asp Asn Leu Arg
     50                  55                  60 ggc tat agt cta aag cta act gct gaa aat gcc ttt gac agt gat agc        240
Gly Tyr Ser Leu Lys Leu Thr Ala Glu Asn Ala Phe Asp Ser Asp Ser
 65                  70                  75                  80 cca gac aaa aaa atg ctt cct tgt tac agc aca gca aga att cca ctg        288
Pro Asp Lys Lys Met Leu Pro Cys Tyr Ser Thr Ala Arg Ile Pro Leu
                 85                  90                  95 ccc aat cta aat gag gac cta acc tgt gga aat cta cta atg tgg gag        336
Pro Asn Leu Asn Glu Asp Leu Thr Cys Gly Asn Leu Leu Met Trp Glu
            100                 105                 110 gct gta act gta aaa aca gag gtt att gga ata act agc atg ctt aac        384
Ala Val Thr Val Lys Thr Glu Val Ile Gly Ile Thr Ser Met Leu Asn
        115                 120                 125 ctt cat gca ggg tcc caa aaa gtt cat gag aat ggt gga ggc aaa cct        432
Leu His Ala Gly Ser Gln Lys Val His Glu Asn Gly Gly Gly Lys Pro
    130                 135                 140 gtc caa ggc agt aat ttc cac ttc ttt gct gtg ggt gga gac ccc ttg        480
Val Gln Gly Ser Asn Phe His Phe Phe Ala Val Gly Gly Asp Pro Leu
145                 150                 155                 160 gaa atg cag gga gtg cta atg aat tac aga aca aag tac cca caa ggt        528
Glu Met Gln Gly Val Leu Met Asn Tyr Arg Thr Lys Tyr Pro Gln Gly
                165                 170                 175 act ata acc cct aaa aac cct aca gct cag tcc cag gta atg aat act        576
Thr Ile Thr Pro Lys Asn Pro Thr Ala Gln Ser Gln Val Met Asn Thr
            180                 185                 190 gat cat aag gcc tat ttg gac aaa aac aat gct tat cca gtt gag tgc        624
Asp His Lys Ala Tyr Leu Asp Lys Asn Asn Ala Tyr Pro Val Glu Cys
        195                 200                 205 tgg att cct gat cct agt aga aat gaa aat act agg tat ttt gga act        672
Trp Ile Pro Asp Pro Ser Arg Asn Glu Asn Thr Arg Tyr Phe Gly Thr
    210                 215                 220 tac aca gga ggg gaa aat gtt ccc cca gta ctt cat gtt acc aac aca        720
Tyr Thr Gly Gly Glu Asn Val Pro Pro Val Leu His Val Thr Asn Thr
225                 230                 235                 240 gct acc aca gtg ttg ctg gat gaa cag ggt gtg ggg cct ctg tgt aaa        768
Ala Thr Thr Val Leu Leu Asp Glu Gln Gly Val Gly Pro Leu Cys Lys
                245                 250                 255 gct gat agc ctg tat gtt tca gct gct gat att tgt ggg ctg ttt act        816
Ala Asp Ser Leu Tyr Val Ser Ala Ala Asp Ile Cys Gly Leu Phe Thr
            260                 265                 270 aac agc tct ggg aca caa cag tgg aga ggc ctt gca aga tat ttt aag        864
Asn Ser Ser Gly Thr Gln Gln Trp Arg Gly Leu Ala Arg Tyr Phe Lys
        275                 280                 285 att cgc ctg aga aaa aga tct gtg aag aat cct tac cca att tcc ttt        912
Ile Arg Leu Arg Lys Arg Ser Val Lys Asn Pro Tyr Pro Ile Ser Phe
    290                 295                 300 ttg cta agt gac ctt ata aac agg aga acc caa aaa gtg gat ggg cag        960
Leu Leu Ser Asp Leu Ile Asn Arg Arg Thr Gln Lys Val Asp Gly Gln
305                 310                 315                 320 cct atg tat ggt atg gaa tct cag gtt gag gag gtg agg gtg ttt gat       1008
Pro Met Tyr Gly Met Glu Ser Gln Val Glu Glu Val Arg Val Phe Asp
                325                 330                 335 ggc aca gaa cag ctt cca ggg gac cca gat atg ata aga tat att gac       1056
Gly Thr Glu Gln Leu Pro Gly Asp Pro Asp Met Ile Arg Tyr Ile Asp
            340                 345                 350 aga caa gga caa ttg caa aca aaa atg gtt taa                           1089
```

Arg Gln Gly Gln Leu Gln Thr Lys Met Val
        355                 360

<210> SEQ ID NO 6
<211> LENGTH: 362
<212> TYPE: PRT
<213> ORGANISM: BK virus

<400> SEQUENCE: 6

Met Ala Pro Thr Lys Arg Lys Gly Glu Cys Pro Gly Ala Ala Pro Arg
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asp Asn Leu Arg
    50                  55                  60

Gly Tyr Ser Leu Lys Leu Thr Ala Glu Asn Ala Phe Asp Ser Asp Ser
65                  70                  75                  80

Pro Asp Lys Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360

<210> SEQ ID NO 7
<211> LENGTH: 1089
<212> TYPE: DNA
<213> ORGANISM: BK virus
<220> FEATURE:
<221> NAME/KEY: CDS
<222> LOCATION: (1)..(1089)
<223> OTHER INFORMATION: VP-1 gene, serotype III

<400> SEQUENCE: 7

```
atg gcc cca acc aaa aga aaa gga gag tgt cca ggg gca gct ccc aaa      48
Met Ala Pro Thr Lys Arg Lys Gly Glu Cys Pro Gly Ala Ala Pro Lys
1               5                  10                  15 aag cca aag gaa ccc gtg caa gtg cca aaa cta cta ata aaa gga gga      96
Lys Pro Lys Glu Pro Val Gln Val Pro Lys Leu Leu Ile Lys Gly Gly
            20                  25                  30 gta gaa gtt cta gaa gtt aaa act ggg gta gat gct ata aca gag gta     144
Val Glu Val Leu Glu Val Lys Thr Gly Val Asp Ala Ile Thr Glu Val
        35                  40                  45 gaa tgc ttt cta aac cca gaa atg ggg gat cca gat gat cac ctt agg     192
Glu Cys Phe Leu Asn Pro Glu Met Gly Asp Pro Asp Asp His Leu Arg
    50                  55                  60 ggc tat agt cag cac cta act gct gaa aat gcc ttt gac agt gat agc     240
Gly Tyr Ser Gln His Leu Thr Ala Glu Asn Ala Phe Asp Ser Asp Ser
65                  70                  75                  80 cca gac aaa aaa atg ctt cct tgt tac agt aca gca aga att cca ctg     288
Pro Asp Lys Lys Met Leu Pro Cys Tyr Ser Thr Ala Arg Ile Pro Leu
                85                  90                  95 ccc aac cta aat gag gac cta acc tgt gga aat cta cta atg tgg gag     336
Pro Asn Leu Asn Glu Asp Leu Thr Cys Gly Asn Leu Leu Met Trp Glu
            100                 105                 110 gct gta act gta aaa aca gag gtt att gga ata act agc atg ctt aac     384
Ala Val Thr Val Lys Thr Glu Val Ile Gly Ile Thr Ser Met Leu Asn
        115                 120                 125 ctt cat gca ggg tcc caa aaa gtt cat gag aat ggt gga ggt aaa cct     432
Leu His Ala Gly Ser Gln Lys Val His Glu Asn Gly Gly Gly Lys Pro
    130                 135                 140 gtc caa ggc agt aat ttc cac ttc ttt gct gtg ggt gga gac ccc ttg     480
Val Gln Gly Ser Asn Phe His Phe Phe Ala Val Gly Gly Asp Pro Leu
145                 150                 155                 160 gaa atg cag gga gtg cta atg aat tac aga aca aag tac cca caa ggt     528
Glu Met Gln Gly Val Leu Met Asn Tyr Arg Thr Lys Tyr Pro Gln Gly
                165                 170                 175 act ata acc cct aaa aac cct aca gct cag tcc cag gta atg aat act     576
Thr Ile Thr Pro Lys Asn Pro Thr Ala Gln Ser Gln Val Met Asn Thr
            180                 185                 190 gat cat aag gcc tat ttg gac aaa aac aat gct tat cca gtt gag tgc     624
Asp His Lys Ala Tyr Leu Asp Lys Asn Asn Ala Tyr Pro Val Glu Cys
        195                 200                 205 tgg att cct gat cct agt aaa aat gaa aat act agg tat ttt gga act     672
Trp Ile Pro Asp Pro Ser Lys Asn Glu Asn Thr Arg Tyr Phe Gly Thr
    210                 215                 220 tac aca gga ggg gaa aat gtt cct cca gta ctt cat gtt acc aac aca     720
Tyr Thr Gly Gly Glu Asn Val Pro Pro Val Leu His Val Thr Asn Thr
225                 230                 235                 240 gct acc aca gtg ttg ctg gat gaa cag ggt gtg ggg cct ctg tgt aaa     768
Ala Thr Thr Val Leu Leu Asp Glu Gln Gly Val Gly Pro Leu Cys Lys
                245                 250                 255 gct gat agc ctg tat gtt tca gct gct gat att tgt ggg ctg ttt act     816
Ala Asp Ser Leu Tyr Val Ser Ala Ala Asp Ile Cys Gly Leu Phe Thr
```

|  |  |  |  |  |  |  |  |  |  |  |  |  |  |  |  |
|---|---|---|---|---|---|---|---|---|---|---|---|---|---|---|---|
|  |  |  |  | 260 |  |  |  |  | 265 |  |  |  |  | 270 |  |
| aac | agc | tct | ggg | aca | caa | cag | tgg | aga | ggc | ctt | gca | aga | tat | ttt | aag | 864 |
| Asn | Ser | Ser | Gly | Thr | Gln | Gln | Trp | Arg | Gly | Leu | Ala | Arg | Tyr | Phe | Lys |  |
|  |  | 275 |  |  |  |  | 280 |  |  |  |  | 285 |  |  |  |  |
| att | cgc | ctg | aga | aaa | aga | tct | gtg | aag | aat | cct | tac | cca | att | tcc | ttt | 912 |
| Ile | Arg | Leu | Arg | Lys | Arg | Ser | Val | Lys | Asn | Pro | Tyr | Pro | Ile | Ser | Phe |  |
|  | 290 |  |  |  |  | 295 |  |  |  |  | 300 |  |  |  |  |  |
| ttg | cta | agt | gac | ctt | ata | aac | agg | aga | acc | caa | aaa | gtg | gat | ggg | cag | 960 |
| Leu | Leu | Ser | Asp | Leu | Ile | Asn | Arg | Arg | Thr | Gln | Lys | Val | Asp | Gly | Gln |  |
| 305 |  |  |  |  | 310 |  |  |  |  | 315 |  |  |  |  | 320 |  |
| cct | atg | tat | ggt | atg | gaa | tct | cag | gtt | gag | gag | gta | agg | gtg | ttt | gat | 1008 |
| Pro | Met | Tyr | Gly | Met | Glu | Ser | Gln | Val | Glu | Glu | Val | Arg | Val | Phe | Asp |  |
|  |  |  |  | 325 |  |  |  |  | 330 |  |  |  |  | 335 |  |  |
| ggc | aca | gaa | cag | ctt | cca | ggg | gac | cca | gat | atg | ata | aga | tat | att | gac | 1056 |
| Gly | Thr | Glu | Gln | Leu | Pro | Gly | Asp | Pro | Asp | Met | Ile | Arg | Tyr | Ile | Asp |  |
|  |  | 340 |  |  |  |  | 345 |  |  |  |  | 350 |  |  |  |  |
| aga | caa | gga | caa | ttg | caa | aca | aaa | atg | gtt | taa |  |  |  |  |  | 1089 |
| Arg | Gln | Gly | Gln | Leu | Gln | Thr | Lys | Met | Val |  |  |  |  |  |  |  |
|  |  | 355 |  |  |  |  | 360 |  |  |  |  |  |  |  |  |  |

<210> SEQ ID NO 8
<211> LENGTH: 362
<212> TYPE: PRT
<213> ORGANISM: BK virus

<400> SEQUENCE: 8

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
                20                  25                  30

Val Glu Val Leu Glu Val Lys Thr Gly Val Asp Ala Ile Thr Glu Val
            35                  40                  45

Glu Cys Phe Leu Asn Pro Glu Met Gly Asp Pro Asp His Leu Arg
        50                  55                  60

Gly Tyr Ser Gln His Leu Thr Ala Glu Asn Ala Phe Asp Ser Asp Ser
65                  70                  75                  80

Pro Asp Lys Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Lys Pro
    130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Lys Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

```
Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360

<210> SEQ ID NO 9
<211> LENGTH: 1089
<212> TYPE: DNA
<213> ORGANISM: BK virus
<220> FEATURE:
<221> NAME/KEY: CDS
<222> LOCATION: (1)..(1089)
<223> OTHER INFORMATION: VP-1 gene, serotype IV

<400> SEQUENCE: 9 atg gcc cca acc aaa aga aag gga gag tgt cca ggg gca gct ccc aaa       48
Met Ala Pro Thr Lys Arg Lys Gly Glu Cys Pro Gly Ala Ala Pro Lys
1               5                   10                  15 aag cca aag gaa ccc gtg caa gtg cca aaa cta cta ata aaa gga gga       96
Lys Pro Lys Glu Pro Val Gln Val Pro Lys Leu Leu Ile Lys Gly Gly
                20                  25                  30 gta gaa gtt cta gaa gtt aaa act ggg cta gat gct ata aca gaa gta      144
Val Glu Val Leu Glu Val Lys Thr Gly Leu Asp Ala Ile Thr Glu Val
            35                  40                  45 gaa tgc ttt cta aat cca gaa atg ggg gat cca gat aat gac ctt agg      192
Glu Cys Phe Leu Asn Pro Glu Met Gly Asp Pro Asp Asn Asp Leu Arg
        50                  55                  60 ggc tat agt cta aga cta act gct gaa act gcc ttt gag agt gat agc      240
Gly Tyr Ser Leu Arg Leu Thr Ala Glu Thr Ala Phe Glu Ser Asp Ser
65                  70                  75                  80 cca gac aga aaa atg ctt ccc tgt tac agc aca gca aga att cca cta      288
Pro Asp Arg Lys Met Leu Pro Cys Tyr Ser Thr Ala Arg Ile Pro Leu
                85                  90                  95 cct aat ttg aat gag gat cta acc tgt gga agt cta cta atg tgg gag      336
Pro Asn Leu Asn Glu Asp Leu Thr Cys Gly Ser Leu Leu Met Trp Glu
            100                 105                 110 gct gtg act gta aaa aca gag gtt att gga ata act agt atg ctt aac      384
Ala Val Thr Val Lys Thr Glu Val Ile Gly Ile Thr Ser Met Leu Asn
        115                 120                 125 ctt cat gca ggg tca cag aaa gta cat gaa aat ggt gga ggc aaa cct      432
Leu His Ala Gly Ser Gln Lys Val His Glu Asn Gly Gly Gly Lys Pro
    130                 135                 140 att caa ggc agc aat ttt cac ttt ttt gct gtg ggt ggg gac ccc ttg      480
Ile Gln Gly Ser Asn Phe His Phe Phe Ala Val Gly Gly Asp Pro Leu
145                 150                 155                 160 gaa atg cag gga gta ctt atg aac tac aga aca aag tac cca gaa ggt      528
Glu Met Gln Gly Val Leu Met Asn Tyr Arg Thr Lys Tyr Pro Glu Gly
                165                 170                 175
```

```
act gtc acc cca aaa aat ccc aca gct cag tcc cag gta atg aat act      576
Thr Val Thr Pro Lys Asn Pro Thr Ala Gln Ser Gln Val Met Asn Thr
            180                 185                 190 gac cat aag gcc tac ttg gac aaa aac aat gct tat cca gtt gaa tgc      624
Asp His Lys Ala Tyr Leu Asp Lys Asn Asn Ala Tyr Pro Val Glu Cys
        195                 200                 205 tgg att cct gac cct agt aga aat gaa aat act agg tat ttt gga aca      672
Trp Ile Pro Asp Pro Ser Arg Asn Glu Asn Thr Arg Tyr Phe Gly Thr
    210                 215                 220 tac aca gga ggg gaa aat gtt ccc cca gta ctt cat gta acc aac aca      720
Tyr Thr Gly Gly Glu Asn Val Pro Pro Val Leu His Val Thr Asn Thr
225                 230                 235                 240 gct acc aca gtg ttg ctg gat gaa cag ggt gtg ggg cct ctg tgt aaa      768
Ala Thr Thr Val Leu Leu Asp Glu Gln Gly Val Gly Pro Leu Cys Lys
                245                 250                 255 gct gat agc ctg tat gtt tca gct gct gat att tgt gga ctg ttt act      816
Ala Asp Ser Leu Tyr Val Ser Ala Ala Asp Ile Cys Gly Leu Phe Thr
            260                 265                 270 aac agc tct gga aca caa cag tgg agg ggc ctt cca aga tat ttt aag      864
Asn Ser Ser Gly Thr Gln Gln Trp Arg Gly Leu Pro Arg Tyr Phe Lys
        275                 280                 285 att cgc ctg aga aaa aga tct gta aag aac cct tac cca att tcc ttt      912
Ile Arg Leu Arg Lys Arg Ser Val Lys Asn Pro Tyr Pro Ile Ser Phe
    290                 295                 300 ttg ctt agt gac ctt ata aac agg aga acc cag aga gtg gat ggg cag      960
Leu Leu Ser Asp Leu Ile Asn Arg Arg Thr Gln Arg Val Asp Gly Gln
305                 310                 315                 320 cct atg tat ggt atg gag tct cag gtg gag gag gtc agg gtg ttt gat     1008
Pro Met Tyr Gly Met Glu Ser Gln Val Glu Glu Val Arg Val Phe Asp
                325                 330                 335 ggc aca gaa cag ctt cca ggg gac cca gat atg ata aga tat att gac     1056
Gly Thr Glu Gln Leu Pro Gly Asp Pro Asp Met Ile Arg Tyr Ile Asp
            340                 345                 350 aga cag gga caa ttg caa aca aaa atg gtt taa                         1089
Arg Gln Gly Gln Leu Gln Thr Lys Met Val
        355                 360

<210> SEQ ID NO 10
<211> LENGTH: 362
<212> TYPE: PRT
<213> ORGANISM: BK virus

<400> SEQUENCE: 10

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Asn Asp Leu Arg
    50                  55                  60

Gly Tyr Ser Leu Arg Leu Thr Ala Glu Thr Ala Phe Glu Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Ser Leu Leu Met Trp Glu
            100                 105                 110

Ala Val Thr Val Lys Thr Glu Val Ile Gly Ile Thr Ser Met Leu Asn
```

```
                    115                 120                 125
Leu His Ala Gly Ser Gln Lys Val His Glu Asn Gly Gly Lys Pro
        130                 135                 140
Ile Gln Gly Ser Asn Phe His Phe Phe Ala Val Gly Gly Asp Pro Leu
145                 150                 155                 160
Glu Met Gln Gly Val Leu Met Asn Tyr Arg Thr Lys Tyr Pro Glu Gly
                165                 170                 175
Thr Val Thr Pro Lys Asn Pro Thr Ala Gln Ser Gln Val Met Asn Thr
            180                 185                 190
Asp His Lys Ala Tyr Leu Asp Lys Asn Asn Ala Tyr Pro Val Glu Cys
                195                 200                 205
Trp Ile Pro Asp Pro Ser Arg Asn Glu Asn Thr Arg Tyr Phe Gly Thr
            210                 215                 220
Tyr Thr Gly Gly Glu Asn Val Pro Pro Val Leu His Val Thr Asn Thr
225                 230                 235                 240
Ala Thr Thr Val Leu Leu Asp Glu Gln Gly Val Gly Pro Leu Cys Lys
                245                 250                 255
Ala Asp Ser Leu Tyr Val Ser Ala Ala Asp Ile Cys Gly Leu Phe Thr
            260                 265                 270
Asn Ser Ser Gly Thr Gln Gln Trp Arg Gly Leu Pro Arg Tyr Phe Lys
                275                 280                 285
Ile Arg Leu Arg Lys Arg Ser Val Lys Asn Pro Tyr Pro Ile Ser Phe
            290                 295                 300
Leu Leu Ser Asp Leu Ile Asn Arg Arg Thr Gln Arg Val Asp Gly Gln
305                 310                 315                 320
Pro Met Tyr Gly Met Glu Ser Gln Val Glu Val Arg Val Phe Asp
                325                 330                 335
Gly Thr Glu Gln Leu Pro Gly Asp Pro Asp Met Ile Arg Tyr Ile Asp
            340                 345                 350
Arg Gln Gly Gln Leu Gln Thr Lys Met Val
        355                 360

<210> SEQ ID NO 11
<211> LENGTH: 15
<212> TYPE: DNA
<213> ORGANISM: Artificial Sequence
<220> FEATURE:
<223> OTHER INFORMATION: 'F6' and 'H6' antibodies, heavy chain, CDR1
<220> FEATURE:
<221> NAME/KEY: CDS
<222> LOCATION: (1)..(15)

<400> SEQUENCE: 11 ggc tac ttt atg aac                                              15
Gly Tyr Phe Met Asn
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Gly Tyr Phe Met Asn
1               5

<210> SEQ ID NO 13
```

```
<211> LENGTH: 51
<212> TYPE: DNA
<213> ORGANISM: Artificial Sequence
<220> FEATURE:
<223> OTHER INFORMATION: 'F6' and 'H6' antibodies, heavy chain, CDR2
<220> FEATURE:
<221> NAME/KEY: CDS
<222> LOCATION: (1)..(51)

<400> SEQUENCE: 13 cgt att aat cct tac aat ggt gat act ttc tac aac cag aag ttc aag    48
Arg Ile Asn Pro Tyr Asn Gly Asp Thr Phe Tyr Asn Gln Lys Phe Lys
1               5                   10                  15 ggc                                                                51
Gly

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Arg Ile Asn Pro Tyr Asn Gly Asp Thr Phe Tyr Asn Gln Lys Phe Lys
1               5                   10                  15

Gly

<210> SEQ ID NO 15
<211> LENGTH: 27
<212> TYPE: DNA
<213> ORGANISM: Artificial Sequence
<220> FEATURE:
<223> OTHER INFORMATION: 'F6' and 'H6' antibodies, heavy chain, CDR3
<220> FEATURE:
<221> NAME/KEY: CDS
<222> LOCATION: (1)..(27)

<400> SEQUENCE: 15 tat tac tac ggc gac tac ttt gac tac                                27
Tyr Tyr Tyr Gly Asp Tyr Phe Asp Tyr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Tyr Tyr Tyr Gly Asp Tyr Phe Asp Tyr
1               5

<210> SEQ ID NO 17
<211> LENGTH: 411
<212> TYPE: DNA
<213> ORGANISM: Artificial Sequence
<220> FEATURE:
<223> OTHER INFORMATION: 'F6' and 'H6' antibodies, heavy chain, variable
      region
<220> FEATURE:
<221> NAME/KEY: CDS
<222> LOCATION: (1)..(411)

<400> SEQUENCE: 17 atg gga tgg agc tgt atc ttt ctc ttt ctc ctg tca gta act gta ggt    48
Met Gly Trp Ser Cys Ile Phe Leu Phe Leu Leu Ser Val Thr Val Gly
```

|  |  |  |  |  |  |  |  |  |  |  |  |  |  |  |  |
|---|---|---|---|---|---|---|---|---|---|---|---|---|---|---|---|
| 1 |  |  |  | 5 |  |  |  |  | 10 |  |  |  |  | 15 |  |

```
gtg ttc tct gag gtt cag ctg cag cag tct gga cct gag ctg gtg aag      96
Val Phe Ser Glu Val Gln Leu Gln Gln Ser Gly Pro Glu Leu Val Lys
             20                  25                  30 cct ggg gct tca gtg aag ata tcc tgc aag gct tct ggt tac tca ttt     144
Pro Gly Ala Ser Val Lys Ile Ser Cys Lys Ala Ser Gly Tyr Ser Phe
         35                  40                  45 act ggc tac ttt atg aac tgg gtg aag cag agc cat gga aag agc ctt     192
Thr Gly Tyr Phe Met Asn Trp Val Lys Gln Ser His Gly Lys Ser Leu
     50                  55                  60 gag tgg att gga cgt att aat cct tac aat ggt gat act ttc tac aac     240
Glu Trp Ile Gly Arg Ile Asn Pro Tyr Asn Gly Asp Thr Phe Tyr Asn
 65                  70                  75                  80 cag aag ttc aag ggc aag gcc aca ttg act gta gac aaa tcc tct agc     288
Gln Lys Phe Lys Gly Lys Ala Thr Leu Thr Val Asp Lys Ser Ser Ser
                 85                  90                  95 aca gcc cac atg gag ctc ctg agc ctg aca tct gag gac tct gca gtc     336
Thr Ala His Met Glu Leu Leu Ser Leu Thr Ser Glu Asp Ser Ala Val
            100                 105                 110 tat tat tgt gga agt tat tac tac ggc gac tac ttt gac tac tgg ggc     384
Tyr Tyr Cys Gly Ser Tyr Tyr Tyr Gly Asp Tyr Phe Asp Tyr Trp Gly
        115                 120                 125 caa ggc acc act ctc aca gtc tcc tca                                 411
Gln Gly Thr Thr Leu Thr Val Ser Ser
    130                 135
```

<210> SEQ ID NO 18
<211> LENGTH: 137
<212> TYPE: PRT
<213> ORGANISM: Artificial Sequence
<220> FEATURE:
<223> OTHER INFORMATION: Synthetic Construct

<400> SEQUENCE: 18

```
Met Gly Trp Ser Cys Ile Phe Leu Phe Leu Leu Ser Val Thr Val Gly
  1               5                  10                  15

Val Phe Ser Glu Val Gln Leu Gln Gln Ser Gly Pro Glu Leu Val Lys
             20                  25                  30

Pro Gly Ala Ser Val Lys Ile Ser Cys Lys Ala Ser Gly Tyr Ser Phe
         35                  40                  45

Thr Gly Tyr Phe Met Asn Trp Val Lys Gln Ser His Gly Lys Ser Leu
     50                  55                  60

Glu Trp Ile Gly Arg Ile Asn Pro Tyr Asn Gly Asp Thr Phe Tyr Asn
 65                  70                  75                  80

Gln Lys Phe Lys Gly Lys Ala Thr Leu Thr Val Asp Lys Ser Ser Ser
                 85                  90                  95

Thr Ala His Met Glu Leu Leu Ser Leu Thr Ser Glu Asp Ser Ala Val
            100                 105                 110

Tyr Tyr Cys Gly Ser Tyr Tyr Tyr Gly Asp Tyr Phe Asp Tyr Trp Gly
        115                 120                 125

Gln Gly Thr Thr Leu Thr Val Ser Ser
    130                 135
```

<210> SEQ ID NO 19
<211> LENGTH: 1386
<212> TYPE: DNA
<213> ORGANISM: Artificial Sequence
<220> FEATURE:
<223> OTHER INFORMATION: 'F6' and 'H6' antibodies, heavy chain
<220> FEATURE:

```
<221> NAME/KEY: CDS
<222> LOCATION: (1)..(1386)

<400> SEQUENCE: 19
```

| | | | | | | | | | | | | | | | | |
|---|---|---|---|---|---|---|---|---|---|---|---|---|---|---|---|---|
| atg | gga | tgg | agc | tgt | atc | ttt | ctc | ttt | ctc | ctg | tca | gta | act | gta | ggt | 48 |
| Met | Gly | Trp | Ser | Cys | Ile | Phe | Leu | Phe | Leu | Leu | Ser | Val | Thr | Val | Gly | |
| 1 | | | | 5 | | | | | 10 | | | | | 15 | | |
| gtg | ttc | tct | gag | gtt | cag | ctg | cag | cag | tct | gga | cct | gag | ctg | gtg | aag | 96 |
| Val | Phe | Ser | Glu | Val | Gln | Leu | Gln | Gln | Ser | Gly | Pro | Glu | Leu | Val | Lys | |
| | | | 20 | | | | | 25 | | | | | 30 | | | |
| cct | ggg | gct | tca | gtg | aag | ata | tcc | tgc | aag | gct | tct | ggt | tac | tca | ttt | 144 |
| Pro | Gly | Ala | Ser | Val | Lys | Ile | Ser | Cys | Lys | Ala | Ser | Gly | Tyr | Ser | Phe | |
| | 35 | | | | | 40 | | | | | 45 | | | | | |
| act | ggc | tac | ttt | atg | aac | tgg | gtg | aag | cag | agc | cat | gga | aag | agc | ctt | 192 |
| Thr | Gly | Tyr | Phe | Met | Asn | Trp | Val | Lys | Gln | Ser | His | Gly | Lys | Ser | Leu | |
| 50 | | | | | 55 | | | | | 60 | | | | | | |
| gag | tgg | att | gga | cgt | att | aat | cct | tac | aat | ggt | gat | act | ttc | tac | aac | 240 |
| Glu | Trp | Ile | Gly | Arg | Ile | Asn | Pro | Tyr | Asn | Gly | Asp | Thr | Phe | Tyr | Asn | |
| 65 | | | | | 70 | | | | | 75 | | | | | 80 | |
| cag | aag | ttc | aag | ggc | aag | gcc | aca | ttg | act | gta | gac | aaa | tcc | tct | agc | 288 |
| Gln | Lys | Phe | Lys | Gly | Lys | Ala | Thr | Leu | Thr | Val | Asp | Lys | Ser | Ser | Ser | |
| | | | | 85 | | | | | 90 | | | | | 95 | | |
| aca | gcc | cac | atg | gag | ctc | ctg | agc | ctg | aca | tct | gag | gac | tct | gca | gtc | 336 |
| Thr | Ala | His | Met | Glu | Leu | Leu | Ser | Leu | Thr | Ser | Glu | Asp | Ser | Ala | Val | |
| | | | 100 | | | | | 105 | | | | | 110 | | | |
| tat | tat | tgt | gga | agt | tat | tac | tac | ggc | gac | tac | ttt | gac | tac | tgg | ggc | 384 |
| Tyr | Tyr | Cys | Gly | Ser | Tyr | Tyr | Tyr | Gly | Asp | Tyr | Phe | Asp | Tyr | Trp | Gly | |
| | | 115 | | | | | 120 | | | | | 125 | | | | |
| caa | ggc | acc | act | ctc | aca | gtc | tcc | tca | gcc | aaa | acg | aca | ccc | cca | tct | 432 |
| Gln | Gly | Thr | Thr | Leu | Thr | Val | Ser | Ser | Ala | Lys | Thr | Thr | Pro | Pro | Ser | |
| 130 | | | | | 135 | | | | | 140 | | | | | | |
| gtc | tat | cca | ctg | gcc | cct | gga | tct | gct | gcc | caa | act | aac | tcc | atg | gtg | 480 |
| Val | Tyr | Pro | Leu | Ala | Pro | Gly | Ser | Ala | Ala | Gln | Thr | Asn | Ser | Met | Val | |
| 145 | | | | | 150 | | | | | 155 | | | | | 160 | |
| acc | ctg | gga | tgc | ctg | gtc | aag | ggc | tat | ttc | cct | gag | cca | gtg | aca | gtg | 528 |
| Thr | Leu | Gly | Cys | Leu | Val | Lys | Gly | Tyr | Phe | Pro | Glu | Pro | Val | Thr | Val | |
| | | | | 165 | | | | | 170 | | | | | 175 | | |
| acc | tgg | aac | tct | gga | tcc | ctg | tcc | agc | ggt | gtg | cac | acc | ttc | cca | gct | 576 |
| Thr | Trp | Asn | Ser | Gly | Ser | Leu | Ser | Ser | Gly | Val | His | Thr | Phe | Pro | Ala | |
| | | | 180 | | | | | 185 | | | | | 190 | | | |
| gtc | ctg | cag | tct | gac | ctc | tac | act | ctg | agc | agc | tca | gtg | act | gtc | ccc | 624 |
| Val | Leu | Gln | Ser | Asp | Leu | Tyr | Thr | Leu | Ser | Ser | Ser | Val | Thr | Val | Pro | |
| | | 195 | | | | | 200 | | | | | 205 | | | | |
| tcc | agc | acc | tgg | ccc | agc | gag | acc | gtc | acc | tgc | aac | gtt | gcc | cac | ccg | 672 |
| Ser | Ser | Thr | Trp | Pro | Ser | Glu | Thr | Val | Thr | Cys | Asn | Val | Ala | His | Pro | |
| 210 | | | | | 215 | | | | | 220 | | | | | | |
| gcc | agc | agc | acc | aag | gtg | gac | aag | aaa | att | gtg | ccc | agg | gat | tgt | ggt | 720 |
| Ala | Ser | Ser | Thr | Lys | Val | Asp | Lys | Lys | Ile | Val | Pro | Arg | Asp | Cys | Gly | |
| 225 | | | | | 230 | | | | | 235 | | | | | 240 | |
| tgt | aag | cct | tgc | ata | tgt | aca | gtc | cca | gaa | gta | tca | tct | gtc | ttc | atc | 768 |
| Cys | Lys | Pro | Cys | Ile | Cys | Thr | Val | Pro | Glu | Val | Ser | Ser | Val | Phe | Ile | |
| | | | | 245 | | | | | 250 | | | | | 255 | | |
| ttc | ccc | cca | aag | ccc | aag | gat | gtg | ctc | acc | att | act | ctg | act | cct | aag | 816 |
| Phe | Pro | Pro | Lys | Pro | Lys | Asp | Val | Leu | Thr | Ile | Thr | Leu | Thr | Pro | Lys | |
| | | | 260 | | | | | 265 | | | | | 270 | | | |
| gtc | acg | tgt | gtt | gtg | gta | gac | atc | agc | aag | gat | gat | ccc | gag | gtc | cag | 864 |
| Val | Thr | Cys | Val | Val | Val | Asp | Ile | Ser | Lys | Asp | Asp | Pro | Glu | Val | Gln | |
| | | 275 | | | | | 280 | | | | | 285 | | | | |
| ttc | agc | tgg | ttt | gta | gat | gat | gtg | gag | gtg | cac | aca | gct | cag | acg | caa | 912 |
| Phe | Ser | Trp | Phe | Val | Asp | Asp | Val | Glu | Val | His | Thr | Ala | Gln | Thr | Gln | |

```
                 290                 295                 300
ccc cgg gag gag cag ttc aac agc act ttc cgc tca gtc agt gaa ctt    960
Pro Arg Glu Glu Gln Phe Asn Ser Thr Phe Arg Ser Val Ser Glu Leu
305                 310                 315                 320 ccc atc atg cac cag gac tgg ctc aat ggc aag gag ttc aaa tgc agg   1008
Pro Ile Met His Gln Asp Trp Leu Asn Gly Lys Glu Phe Lys Cys Arg
                325                 330                 335 gtc aac agt gca gct ttc cct gcc ccc atc gag aaa acc atc tcc aaa   1056
Val Asn Ser Ala Ala Phe Pro Ala Pro Ile Glu Lys Thr Ile Ser Lys
            340                 345                 350 acc aaa ggc aga ccg aag gct cca cag gtg tac acc att cca cct ccc   1104
Thr Lys Gly Arg Pro Lys Ala Pro Gln Val Tyr Thr Ile Pro Pro Pro
        355                 360                 365 aag gag cag atg gcc aag gat aaa gtc agt ctg acc tgc atg ata aca   1152
Lys Glu Gln Met Ala Lys Asp Lys Val Ser Leu Thr Cys Met Ile Thr
    370                 375                 380 gac ttc ttc cct gaa gac att act gtg gag tgg cag tgg aat ggg cag   1200
Asp Phe Phe Pro Glu Asp Ile Thr Val Glu Trp Gln Trp Asn Gly Gln
385                 390                 395                 400 cca gcg gag aac tac aag aac act cag ccc atc atg gac aca gat ggc   1248
Pro Ala Glu Asn Tyr Lys Asn Thr Gln Pro Ile Met Asp Thr Asp Gly
                405                 410                 415 tct tac ttc gtc tac agc aag ctc aat gtg cag aag agc aac tgg gag   1296
Ser Tyr Phe Val Tyr Ser Lys Leu Asn Val Gln Lys Ser Asn Trp Glu
            420                 425                 430 gca gga aat act ttc acc tgc tct gtg tta cat gag ggc ctg cac aac   1344
Ala Gly Asn Thr Phe Thr Cys Ser Val Leu His Glu Gly Leu His Asn
        435                 440                 445 cac cat act gag aag agc ctc tcc cac tct cct ggt aaa tga            1386
His His Thr Glu Lys Ser Leu Ser His Ser Pro Gly Lys
    450                 455                 460

<210> SEQ ID NO 20
<211> LENGTH: 461
<212> TYPE: PRT
<213> ORGANISM: Artificial Sequence
<220> FEATURE:
<223> OTHER INFORMATION: Synthetic Construct

<400> SEQUENCE: 20

Met Gly Trp Ser Cys Ile Phe Leu Phe Leu Leu Ser Val Thr Val Gly
1               5                   10                  15

Val Phe Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Phe Met Asn Trp Val Lys Gln Ser His Gly Lys Ser Leu
    50                  55                  60

Glu Trp Ile Gly Arg Ile Asn Pro Tyr Asn Gly Asp Thr Phe Tyr Asn
65                  70                  75                  80

Gln Lys Phe Lys Gly Lys Ala Thr Leu Thr Val Asp Lys Ser Ser Ser
                85                  90                  95

Thr Ala His Met Glu Leu Leu Ser Leu Thr Ser Glu Asp Ser Ala Val
            100                 105                 110

Tyr Tyr Cys Gly Ser Tyr Tyr Gly Asp Tyr Phe Asp Tyr Trp Gly
        115                 120                 125

Gln Gly Thr Thr Leu Thr Val Ser Ser Ala Lys Thr Thr Pro Pro Ser
    130                 135                 140
```

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
            165                 170                 175

Thr Trp Asn Ser Gly Ser Leu Ser Ser Gly Val His Thr Phe Pro Ala
        180                 185                 190

Val Leu Gln Ser Asp Leu Tyr Thr Leu Ser Ser Val Thr Val Pro
    195                 200                 205

Ser Ser Thr Trp Pro Ser Glu Thr Val Thr Cys Asn Val Ala His Pro
210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Gln
290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
        435                 440                 445

His His Thr Glu Lys Ser Leu Ser His Ser Pro Gly Lys
450                 455                 460

<210> SEQ ID NO 21
<211> LENGTH: 51
<212> TYPE: DNA
<213> ORGANISM: Artificial Sequence
<220> FEATURE:
<223> OTHER INFORMATION: 'F6' antibody, light chain, CDR1
<220> FEATURE:
<221> NAME/KEY: CDS
<222> LOCATION: (1)..(51)

<400> SEQUENCE: 21 aag tcc agt cag agc ctt tta tat agt agc aat caa aag aac tac ttg    48
Lys Ser Ser Gln Ser Leu Leu Tyr Ser Ser Asn Gln Lys Asn Tyr Leu
1               5                   10                  15 gcc                                                                51
Ala

<210> SEQ ID NO 22
<211> LENGTH: 17
<212> TYPE: PRT
<213> ORGANISM: Artificial Sequence
<220> FEATURE:
<223> OTHER INFORMATION: Synthetic Construct

<400> SEQUENCE: 22

Lys Ser Ser Gln Ser Leu Leu Tyr Ser Ser Asn Gln Lys Asn Tyr Leu
1               5                   10                  15

Ala

<210> SEQ ID NO 23
<211> LENGTH: 21
<212> TYPE: DNA
<213> ORGANISM: Artificial Sequence
<220> FEATURE:
<223> OTHER INFORMATION: 'F6' antibody, light chain, CDR2
<220> FEATURE:
<221> NAME/KEY: CDS
<222> LOCATION: (1)..(21)

<400> SEQUENCE: 23 tgg gca tcc act agg gaa tct                                     21
Trp Ala Ser Thr Arg Glu Ser
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

Trp Ala Ser Thr Arg Glu Ser
1               5

<210> SEQ ID NO 25
<211> LENGTH: 27
<212> TYPE: DNA
<213> ORGANISM: Artificial Sequence
<220> FEATURE:
<223> OTHER INFORMATION: 'F6' antibody, light chain, CDR3
<220> FEATURE:
<221> NAME/KEY: CDS
<222> LOCATION: (1)..(27)

<400> SEQUENCE: 25 cag caa tat tat agc tat ccg ctc acg                             27
Gln Gln Tyr Tyr Ser Tyr Pro Leu Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Gln Gln Tyr Tyr Ser Tyr Pro Leu Thr
1               5

<210> SEQ ID NO 27
<211> LENGTH: 399

```
<212> TYPE: DNA
<213> ORGANISM: Artificial Sequence
<220> FEATURE:
<223> OTHER INFORMATION: 'F6' antibody, light chain, variable region
<220> FEATURE:
<221> NAME/KEY: CDS
<222> LOCATION: (1)..(399)

<400> SEQUENCE: 27 atg gat tca cag gcc cag gtt ctt atg tta ctg ctg cta tgg gta tct      48
Met Asp Ser Gln Ala Gln Val Leu Met Leu Leu Leu Leu Trp Val Ser
1               5                   10                  15 ggt acc tgt ggg gac att gtg atg tca cag tct cca tcc tcc cta gct      96
Gly Thr Cys Gly Asp Ile Val Met Ser Gln Ser Pro Ser Ser Leu Ala
            20                  25                  30 gtg tca gtt gga gag aag gtt act atg agc tgc aag tcc agt cag agc     144
Val Ser Val Gly Glu Lys Val Thr Met Ser Cys Lys Ser Ser Gln Ser
35                  40                  45 ctt tta tat agt agc aat caa aag aac tac ttg gcc tgg tac cag cag     192
Leu Leu Tyr Ser Ser Asn Gln Lys Asn Tyr Leu Ala Trp Tyr Gln Gln
    50                  55                  60 aaa cca ggg cag tct cct aaa ctg ctg att tac tgg gca tcc act agg     240
Lys Pro Gly Gln Ser Pro Lys Leu Leu Ile Tyr Trp Ala Ser Thr Arg
65                  70                  75                  80 gaa tct ggg gtc cct gat cgc ttc aca ggc agt gga tct ggg aca gat     288
Glu Ser Gly Val Pro Asp Arg Phe Thr Gly Ser Gly Ser Gly Thr Asp
                85                  90                  95 ttc act ctc acc atc agc agt gtg aag gct gaa gac ctg gca gtt tat     336
Phe Thr Leu Thr Ile Ser Ser Val Lys Ala Glu Asp Leu Ala Val Tyr
            100                 105                 110 tac tgt cag caa tat tat agc tat ccg ctc acg ttc ggt gct ggg acc     384
Tyr Cys Gln Gln Tyr Tyr Ser Tyr Pro Leu Thr Phe Gly Ala Gly Thr
        115                 120                 125 aag ctg gag ctg aaa                                                  399
Lys Leu Glu Leu Lys
    130

<210> SEQ ID NO 28
<211> LENGTH: 133
<212> TYPE: PRT
<213> ORGANISM: Artificial Sequence
<220> FEATURE:
<223> OTHER INFORMATION: Synthetic Construct

<400> SEQUENCE: 28

Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Leu Thr Phe Gly Ala Gly Thr
        115                 120                 125
```

```
Lys Leu Glu Leu Lys
        130

<210> SEQ ID NO 29
<211> LENGTH: 723
<212> TYPE: DNA
<213> ORGANISM: Artificial Sequence
<220> FEATURE:
<223> OTHER INFORMATION: 'F6' antibody, light chain
<220> FEATURE:
<221> NAME/KEY: CDS
<222> LOCATION: (1)..(723)

<400> SEQUENCE: 29 atg gat tca cag gcc cag gtt ctt atg tta ctg ctg cta tgg gta tct       48
Met Asp Ser Gln Ala Gln Val Leu Met Leu Leu Leu Leu Trp Val Ser
1               5                   10                  15 ggt acc tgt ggg gac att gtg atg tca cag tct cca tcc tcc cta gct       96
Gly Thr Cys Gly Asp Ile Val Met Ser Gln Ser Pro Ser Ser Leu Ala
                20                  25                  30 gtg tca gtt gga gag aag gtt act atg agc tgc aag tcc agt cag agc      144
Val Ser Val Gly Glu Lys Val Thr Met Ser Cys Lys Ser Ser Gln Ser
            35                  40                  45 ctt tta tat agt agc aat caa aag aac tac ttg gcc tgg tac cag cag      192
Leu Leu Tyr Ser Ser Asn Gln Lys Asn Tyr Leu Ala Trp Tyr Gln Gln
        50                  55                  60 aaa cca ggg cag tct cct aaa ctg ctg att tac tgg gca tcc act agg      240
Lys Pro Gly Gln Ser Pro Lys Leu Leu Ile Tyr Trp Ala Ser Thr Arg
65                  70                  75                  80 gaa tct ggg gtc cct gat cgc ttc aca ggc agt gga tct ggg aca gat      288
Glu Ser Gly Val Pro Asp Arg Phe Thr Gly Ser Gly Ser Gly Thr Asp
                85                  90                  95 ttc act ctc acc atc agc agt gtg aag gct gaa gac ctg gca gtt tat      336
Phe Thr Leu Thr Ile Ser Ser Val Lys Ala Glu Asp Leu Ala Val Tyr
                100                 105                 110 tac tgt cag caa tat tat agc tat ccg ctc acg ttc ggt gct ggg acc      384
Tyr Cys Gln Gln Tyr Tyr Ser Tyr Pro Leu Thr Phe Gly Ala Gly Thr
            115                 120                 125 aag ctg gag ctg aaa cgg gct gat gct gca cca act gta tcc atc ttc      432
Lys Leu Glu Leu Lys Arg Ala Asp Ala Ala Pro Thr Val Ser Ile Phe
        130                 135                 140 cca cca tcc agt gag cag tta aca tct gga ggt gcc tca gtc gtg tgc      480
Pro Pro Ser Ser Glu Gln Leu Thr Ser Gly Gly Ala Ser Val Val Cys
145                 150                 155                 160 ttc ttg aac aac ttc tac ccc aaa gac atc aat gtc aag tgg aag att      528
Phe Leu Asn Asn Phe Tyr Pro Lys Asp Ile Asn Val Lys Trp Lys Ile
                165                 170                 175 gat ggc agt gaa cga caa aat ggc gtc ctg aac agt tgg act gat cag      576
Asp Gly Ser Glu Arg Gln Asn Gly Val Leu Asn Ser Trp Thr Asp Gln
                180                 185                 190 gac agc aaa gac agc acc tac agc atg agc agc acc ctc acg ttg acc      624
Asp Ser Lys Asp Ser Thr Tyr Ser Met Ser Ser Thr Leu Thr Leu Thr
            195                 200                 205 aag gac gag tat gaa cga cat aac agc tat acc tgt gag gcc act cac      672
Lys Asp Glu Tyr Glu Arg His Asn Ser Tyr Thr Cys Glu Ala Thr His
        210                 215                 220 aag aca tca act tca ccc att gtc aag agc ttc aac agg aat gag tgt      720
Lys Thr Ser Thr Ser Pro Ile Val Lys Ser Phe Asn Arg Asn Glu Cys
225                 230                 235                 240 tag                                                                  723
```

-continued

<210> SEQ ID NO 30
<211> LENGTH: 240
<212> TYPE: PRT
<213> ORGANISM: Artificial Sequence
<220> FEATURE:
<223> OTHER INFORMATION: Synthetic Construct

<400> SEQUENCE: 30

```
Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Leu Thr Phe Gly Ala Gly Thr
        115                 120                 125

Lys Leu Glu Leu Lys Arg Ala Asp Ala Ala Pro Thr Val Ser Ile Phe
    130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
            180                 185                 190

Asp Ser Lys Asp Ser Thr Tyr Ser Met Ser Ser Thr Leu Thr Leu Thr
        195                 200                 205

Lys Asp Glu Tyr Glu Arg His Asn Ser Tyr Thr Cys Glu Ala Thr His
    210                 215                 220

Lys Thr Ser Thr Ser Pro Ile Val Lys Ser Phe Asn Arg Asn Glu Cys
225                 230                 235                 240
```

<210> SEQ ID NO 31
<211> LENGTH: 33
<212> TYPE: DNA
<213> ORGANISM: Artificial Sequence
<220> FEATURE:
<223> OTHER INFORMATION: 'H6' antibody, light chain, CDR1
<220> FEATURE:
<221> NAME/KEY: CDS
<222> LOCATION: (1)..(33)

<400> SEQUENCE: 31

```
aag gcc agt cag agt gtg agt aat gat gta gct                    33
Lys Ala Ser Gln Ser Val Ser Asn Asp Val Ala
1               5                   10
```

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Lys Ala Ser Gln Ser Val Ser Asn Asp Val Ala
1               5                   10

<210> SEQ ID NO 33
<211> LENGTH: 21
<212> TYPE: DNA
<213> ORGANISM: Artificial Sequence
<220> FEATURE:
<223> OTHER INFORMATION: 'H6' antibody, light chain, CDR2
<220> FEATURE:
<221> NAME/KEY: CDS
<222> LOCATION: (1)..(21)

<400> SEQUENCE: 33 tat gca tcc aat cgc tac act                                          21
Tyr Ala Ser Asn Arg Tyr Thr
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

Tyr Ala Ser Asn Arg Tyr Thr
1               5

<210> SEQ ID NO 35
<211> LENGTH: 27
<212> TYPE: DNA
<213> ORGANISM: Artificial Sequence
<220> FEATURE:
<223> OTHER INFORMATION: 'H6' antibody, light chain, CDR3
<220> FEATURE:
<221> NAME/KEY: CDS
<222> LOCATION: (1)..(27)

<400> SEQUENCE: 35 cag cag gat tat agt tct ccg ctc acg                                  27
Gln Gln Asp Tyr Ser Ser Pro Leu Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

Gln Gln Asp Tyr Ser Ser Pro Leu Thr
1               5

<210> SEQ ID NO 37
<211> LENGTH: 381
<212> TYPE: DNA
<213> ORGANISM: Artificial Sequence
<220> FEATURE:
<223> OTHER INFORMATION: 'H6' antibody, light chain, variable region
<220> FEATURE:
<221> NAME/KEY: CDS
<222> LOCATION: (1)..(381)

<400> SEQUENCE: 37

```
atg aag tca cag acc cag gtc ttc gta ttt cta ctg ctc tgt gtg tct      48
Met Lys Ser Gln Thr Gln Val Phe Val Phe Leu Leu Leu Cys Val Ser
1               5                   10                  15 ggt gct cat ggg agt att gtg atg acc cag att ccc aaa ttc ctg ctt      96
Gly Ala His Gly Ser Ile Val Met Thr Gln Ile Pro Lys Phe Leu Leu
            20                  25                  30 gta tca gaa gga gac agg gtt acc ata acc tgc aag gcc agt cag agt     144
Val Ser Glu Gly Asp Arg Val Thr Ile Thr Cys Lys Ala Ser Gln Ser
        35                  40                  45 gtg agt aat gat gta gct tgg tac caa cag aag tca ggg cag tct cct     192
Val Ser Asn Asp Val Ala Trp Tyr Gln Gln Lys Ser Gly Gln Ser Pro
50                  55                  60 aaa ctg ctg ata tac tat gca tcc aat cgc tac act gga gtc cct gat     240
Lys Leu Leu Ile Tyr Tyr Ala Ser Asn Arg Tyr Thr Gly Val Pro Asp
65                  70                  75                  80 cgc ttc act ggc agt gga tat ggg acg gat ttc act ttc acc atc agc     288
Arg Phe Thr Gly Ser Gly Tyr Gly Thr Asp Phe Thr Phe Thr Ile Ser
                85                  90                  95 act gtg cag gct gaa gac ctg gca gtt tat ttc tgt cag cag gat tat     336
Thr Val Gln Ala Glu Asp Leu Ala Val Tyr Phe Cys Gln Gln Asp Tyr
            100                 105                 110 agt tct ccg ctc acg ttc ggt gct ggg acc aag ctg gag ctg aaa         381
Ser Ser Pro Leu Thr Phe Gly Ala Gly Thr Lys Leu Glu Leu Lys
        115                 120                 125
```

<210> SEQ ID NO 38
<211> LENGTH: 127
<212> TYPE: PRT
<213> ORGANISM: Artificial Sequence
<220> FEATURE:
<223> OTHER INFORMATION: Synthetic Construct

<400> SEQUENCE: 38

```
Met Lys Ser Gln Thr Gln Val Phe Val Phe Leu Leu Leu Cys Val Ser
1               5                   10                  15

Gly Ala His Gly Ser Ile Val Met Thr Gln Ile Pro Lys Phe Leu Leu
            20                  25                  30

Val Ser Glu Gly Asp Arg Val Thr Ile Thr Cys Lys Ala Ser Gln Ser
        35                  40                  45

Val Ser Asn Asp Val Ala Trp Tyr Gln Gln Lys Ser Gly Gln Ser Pro
50                  55                  60

Lys Leu Leu Ile Tyr Tyr Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
            100                 105                 110

Ser Ser Pro Leu Thr Phe Gly Ala Gly Thr Lys Leu Glu Leu Lys
        115                 120                 125
```

<210> SEQ ID NO 39
<211> LENGTH: 705
<212> TYPE: DNA
<213> ORGANISM: Artificial Sequence
<220> FEATURE:
<223> OTHER INFORMATION: 'H6' antibody, light chain
<220> FEATURE:
<221> NAME/KEY: CDS
<222> LOCATION: (1)..(705)

<400> SEQUENCE: 39

```
atg aag tca cag acc cag gtc ttc gta ttt cta ctg ctc tgt gtg tct    48
Met Lys Ser Gln Thr Gln Val Phe Val Phe Leu Leu Leu Cys Val Ser
1               5                   10                  15 ggt gct cat ggg agt att gtg atg acc cag att ccc aaa ttc ctg ctt    96
Gly Ala His Gly Ser Ile Val Met Thr Gln Ile Pro Lys Phe Leu Leu
                20                  25                  30 gta tca gaa gga gac agg gtt acc ata acc tgc aag gcc agt cag agt   144
Val Ser Glu Gly Asp Arg Val Thr Ile Thr Cys Lys Ala Ser Gln Ser
            35                  40                  45 gtg agt aat gat gta gct tgg tac caa cag aag tca ggg cag tct cct   192
Val Ser Asn Asp Val Ala Trp Tyr Gln Gln Lys Ser Gly Gln Ser Pro
        50                  55                  60 aaa ctg ctg ata tac tat gca tcc aat cgc tac act gga gtc cct gat   240
Lys Leu Leu Ile Tyr Tyr Ala Ser Asn Arg Tyr Thr Gly Val Pro Asp
65              70                  75                  80 cgc ttc act ggc agt gga tat ggg acg gat ttc act ttc acc atc agc   288
Arg Phe Thr Gly Ser Gly Tyr Gly Thr Asp Phe Thr Phe Thr Ile Ser
                85                  90                  95 act gtg cag gct gaa gac ctg gca gtt tat ttc tgt cag cag gat tat   336
Thr Val Gln Ala Glu Asp Leu Ala Val Tyr Phe Cys Gln Gln Asp Tyr
            100                 105                 110 agt tct ccg ctc acg ttc ggt gct ggg acc aag ctg gag ctg aaa cgg   384
Ser Ser Pro Leu Thr Phe Gly Ala Gly Thr Lys Leu Glu Leu Lys Arg
        115                 120                 125 gct gat gct gca cca act gta tcc atc ttc cca cca tcc agt gag cag   432
Ala Asp Ala Ala Pro Thr Val Ser Ile Phe Pro Pro Ser Ser Glu Gln
130                 135                 140 tta aca tct gga ggt gcc tca gtc gtg tgc ttc ttg aac aac ttc tac   480
Leu Thr Ser Gly Gly Ala Ser Val Val Cys Phe Leu Asn Asn Phe Tyr
145                 150                 155                 160 ccc aaa gac atc aat gtc aag tgg aag att gat ggc agt gaa cga caa   528
Pro Lys Asp Ile Asn Val Lys Trp Lys Ile Asp Gly Ser Glu Arg Gln
                165                 170                 175 aat ggc gtc ctg aac agt tgg act gat cag gac agc aaa gac agc acc   576
Asn Gly Val Leu Asn Ser Trp Thr Asp Gln Asp Ser Lys Asp Ser Thr
            180                 185                 190 tac agc atg agc agc acc ctc acg ttg acc aag gac gag tat gaa cga   624
Tyr Ser Met Ser Ser Thr Leu Thr Leu Thr Lys Asp Glu Tyr Glu Arg
        195                 200                 205 cat aac agc tat acc tgt gag gcc act cac aag aca tca act tca ccc   672
His Asn Ser Tyr Thr Cys Glu Ala Thr His Lys Thr Ser Thr Ser Pro
210                 215                 220 att gtc aag agc ttc aac agg aat gag tgt tag                       705
Ile Val Lys Ser Phe Asn Arg Asn Glu Cys
225                 230
```

<210> SEQ ID NO 40
<211> LENGTH: 234
<212> TYPE: PRT
<213> ORGANISM: Artificial Sequence
<220> FEATURE:
<223> OTHER INFORMATION: Synthetic Construct

<400> SEQUENCE: 40

```
Met Lys Ser Gln Thr Gln Val Phe Val Phe Leu Leu Leu Cys Val Ser
1               5                   10                  15

Gly Ala His Gly Ser Ile Val Met Thr Gln Ile Pro Lys Phe Leu Leu
                20                  25                  30

Val Ser Glu Gly Asp Arg Val Thr Ile Thr Cys Lys Ala Ser Gln Ser
            35                  40                  45
```

```
Val Ser Asn Asp Val Ala Trp Tyr Gln Gln Lys Ser Gly Gln Ser Pro
    50                  55                  60

Lys Leu Leu Ile Tyr Tyr Ala Ser Asn Arg Tyr Thr Gly Val Pro Asp
 65                  70                  75                  80

Arg Phe Thr Gly Ser Gly Tyr Gly Thr Asp Phe Thr Phe Thr Ile Ser
                 85                  90                  95

Thr Val Gln Ala Glu Asp Leu Ala Val Tyr Phe Cys Gln Gln Asp Tyr
            100                 105                 110

Ser Ser Pro Leu Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 41
<211> LENGTH: 18
<212> TYPE: DNA
<213> ORGANISM: Artificial Sequence
<220> FEATURE:
<223> OTHER INFORMATION: '9B1', '14D6' and '18A2' antibodies, heavy
      chain, CDR1
<220> FEATURE:
<221> NAME/KEY: CDS
<222> LOCATION: (1)..(18)

<400> SEQUENCE: 41 agt ggt tat tac tgg aac                                           18
Ser Gly Tyr Tyr Trp Asn
 1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic Construct

<400> SEQUENCE: 42

Ser Gly Tyr Tyr Trp Asn
 1               5

<210> SEQ ID NO 43
<211> LENGTH: 48
<212> TYPE: DNA
<213> ORGANISM: Artificial Sequence
<220> FEATURE:
<223> OTHER INFORMATION: '9B1', '14D6' and '18A2' antibodies, heavy
      chain, CDR2
<220> FEATURE:
<221> NAME/KEY: CDS
<222> LOCATION: (1)..(48)
```

-continued

```
<400> SEQUENCE: 43 tac ata agc tac gac ggt agc aat aac tac aac cca tct ctc aaa aat        48
Tyr Ile Ser Tyr Asp Gly Ser Asn Asn Tyr Asn Pro Ser Leu Lys Asn
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic Construct

<400> SEQUENCE: 44

Tyr Ile Ser Tyr Asp Gly Ser Asn Asn Tyr Asn Pro Ser Leu Lys Asn
1               5                   10                  15

<210> SEQ ID NO 45
<211> LENGTH: 30
<212> TYPE: DNA
<213> ORGANISM: Artificial Sequence
<220> FEATURE:
<223> OTHER INFORMATION: '9B1' antibody, heavy chain, CDR3
<220> FEATURE:
<221> NAME/KEY: CDS
<222> LOCATION: (1)..(30)

<400> SEQUENCE: 45 gtg gat ggt aac tcc tgg tac ttc gat gtc                                30
Val Asp Gly Asn Ser Trp Tyr Phe Asp Val
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Val Asp Gly Asn Ser Trp Tyr Phe Asp Val
1               5                   10

<210> SEQ ID NO 47
<211> LENGTH: 411
<212> TYPE: DNA
<213> ORGANISM: Artificial Sequence
<220> FEATURE:
<223> OTHER INFORMATION: '9B1' antibody, heavy chain, variable region
<220> FEATURE:
<221> NAME/KEY: CDS
<222> LOCATION: (1)..(411)

<400> SEQUENCE: 47 atg aaa gtg ttg agt ctg ttg tac ctg ttg aca gcc att cct ggt atc        48
Met Lys Val Leu Ser Leu Leu Tyr Leu Leu Thr Ala Ile Pro Gly Ile
1               5                   10                  15 ctg tct gat gta cag ctt cag gag tca gga cct ggc ctc gtg aaa cct        96
Leu Ser Asp Val Gln Leu Gln Glu Ser Gly Pro Gly Leu Val Lys Pro
                20                  25                  30 tct cag tct ctg tct ctc acc tgc tct gtc act ggc tac tcc atc acc        144
Ser Gln Ser Leu Ser Leu Thr Cys Ser Val Thr Gly Tyr Ser Ile Thr
            35                  40                  45 agt ggt tat tac tgg aac tgg atc cgg cag ttt cca gga aac aaa ctg        192
Ser Gly Tyr Tyr Trp Asn Trp Ile Arg Gln Phe Pro Gly Asn Lys Leu
        50                  55                  60 gaa tgg atg ggc tac ata agc tac gac ggt agc aat aac tac aac cca        240
```

```
Glu Trp Met Gly Tyr Ile Ser Tyr Asp Gly Ser Asn Asn Tyr Asn Pro
 65                  70                  75                  80 tct ctc aaa aat cga atc tcc atc act cgt gac aca tct aag aac cag      288
Ser Leu Lys Asn Arg Ile Ser Ile Thr Arg Asp Thr Ser Lys Asn Gln
                 85                  90                  95 ttt ttc ctg aag ttg aat tct gtg act act gag gac aca gct aca tat      336
Phe Phe Leu Lys Leu Asn Ser Val Thr Thr Glu Asp Thr Ala Thr Tyr
            100                 105                 110 tat tgt gca aga gtg gat ggt aac tcc tgg tac ttc gat gtc tgg ggc      384
Tyr Cys Ala Arg Val Asp Gly Asn Ser Trp Tyr Phe Asp Val Trp Gly
            115                 120                 125 gca ggg acc acg gtc acc gtc tcc tca                                  411
Ala Gly Thr Thr Val Thr Val Ser Ser
    130                 135

<210> SEQ ID NO 48
<211> LENGTH: 137
<212> TYPE: PRT
<213> ORGANISM: Artificial Sequence
<220> FEATURE:
<223> OTHER INFORMATION: Synthetic Construct

<400> SEQUENCE: 48

Met Lys Val Leu Ser Leu Leu Tyr Leu Leu Thr Ala Ile Pro Gly Ile
 1               5                  10                  15

Leu Ser Asp Val Gln Leu Gln Glu Ser Gly Pro Gly Leu Val Lys Pro
                 20                  25                  30

Ser Gln Ser Leu Ser Leu Thr Cys Ser Val Thr Gly Tyr Ser Ile Thr
             35                  40                  45

Ser Gly Tyr Tyr Trp Asn Trp Ile Arg Gln Phe Pro Gly Asn Lys Leu
 50                  55                  60

Glu Trp Met Gly Tyr Ile Ser Tyr Asp Gly Ser Asn Asn Tyr Asn Pro
 65                  70                  75                  80

Ser Leu Lys Asn Arg Ile Ser Ile Thr Arg Asp Thr Ser Lys Asn Gln
                 85                  90                  95

Phe Phe Leu Lys Leu Asn Ser Val Thr Thr Glu Asp Thr Ala Thr Tyr
            100                 105                 110

Tyr Cys Ala Arg Val Asp Gly Asn Ser Trp Tyr Phe Asp Val Trp Gly
            115                 120                 125

Ala Gly Thr Thr Val Thr Val Ser Ser
    130                 135

<210> SEQ ID NO 49
<211> LENGTH: 33
<212> TYPE: DNA
<213> ORGANISM: Artificial Sequence
<220> FEATURE:
<223> OTHER INFORMATION: '9B1' antibody, light chain, CDR1
<220> FEATURE:
<221> NAME/KEY: CDS
<222> LOCATION: (1)..(33)

<400> SEQUENCE: 49 aag gca agt gag gac ata tat aat cgg tta gcc                          33
Lys Ala Ser Glu Asp Ile Tyr Asn Arg Leu Ala
 1               5                  10

<210> SEQ ID NO 50
<211> LENGTH: 11
<212> TYPE: PRT
<213> ORGANISM: Artificial Sequence
<220> FEATURE:
```

```
<223> OTHER INFORMATION: Synthetic Construct

<400> SEQUENCE: 50

Lys Ala Ser Glu Asp Ile Tyr Asn Arg Leu Ala
1               5                   10

<210> SEQ ID NO 51
<211> LENGTH: 21
<212> TYPE: DNA
<213> ORGANISM: Artificial Sequence
<220> FEATURE:
<223> OTHER INFORMATION: '9B1' antibody, light chain, CDR2
<220> FEATURE:
<221> NAME/KEY: CDS
<222> LOCATION: (1)..(21)

<400> SEQUENCE: 51 ggt gca acc agt ttg gaa act                                        21
Gly Ala Thr Ser Leu Glu Thr
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic Construct

<400> SEQUENCE: 52

Gly Ala Thr Ser Leu Glu Thr
1               5

<210> SEQ ID NO 53
<211> LENGTH: 27
<212> TYPE: DNA
<213> ORGANISM: Artificial Sequence
<220> FEATURE:
<223> OTHER INFORMATION: '9B1' antibody, light chain, CDR3
<220> FEATURE:
<221> NAME/KEY: CDS
<222> LOCATION: (1)..(27)

<400> SEQUENCE: 53 caa cag tat tgg agt att ctg ctc acg                                27
Gln Gln Tyr Trp Ser Ile Leu Leu Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Construct

<400> SEQUENCE: 54

Gln Gln Tyr Trp Ser Ile Leu Leu Thr
1               5

<210> SEQ ID NO 55
<211> LENGTH: 381
<212> TYPE: DNA
<213> ORGANISM: Artificial Sequence
<220> FEATURE:
<223> OTHER INFORMATION: '9B1' antibody, light chain, variable region
<220> FEATURE:
<221> NAME/KEY: CDS
<222> LOCATION: (1)..(381)

<400> SEQUENCE: 55
```

```
atg aag ttt cct tct caa ctt ctg ctc tta ctg ctt ttt gga atc cca      48
Met Lys Phe Pro Ser Gln Leu Leu Leu Leu Leu Phe Gly Ile Pro
1               5                   10                  15 ggc atg ata tgt gac atc cag atg aca caa tct tca tcc tcc ttt tct      96
Gly Met Ile Cys Asp Ile Gln Met Thr Gln Ser Ser Ser Ser Phe Ser
                20                  25                  30 gta tct cta gga gac aga gtc acc att act tgc aag gca agt gag gac     144
Val Ser Leu Gly Asp Arg Val Thr Ile Thr Cys Lys Ala Ser Glu Asp
            35                  40                  45 ata tat aat cgg tta gcc tgg tat cag cag aaa cca gga aat gct cct     192
Ile Tyr Asn Arg Leu Ala Trp Tyr Gln Gln Lys Pro Gly Asn Ala Pro
        50                  55                  60 agg ctc tta ata tct ggt gca acc agt ttg gaa act ggg gtt cct tca     240
Arg Leu Leu Ile Ser Gly Ala Thr Ser Leu Glu Thr Gly Val Pro Ser
65                  70                  75                  80 aga ttc agt ggc agt gga tct gga aag gat tac act ctc agc att acc     288
Arg Phe Ser Gly Ser Gly Ser Gly Lys Asp Tyr Thr Leu Ser Ile Thr
                85                  90                  95 agt ctt cag act gaa gat gtt gct act tat tac tgt caa cag tat tgg     336
Ser Leu Gln Thr Glu Asp Val Ala Thr Tyr Tyr Cys Gln Gln Tyr Trp
            100                 105                 110 agt att ctg ctc acg ttc ggt gct ggg acc aag ctg gag ctg aaa         381
Ser Ile Leu Leu Thr Phe Gly Ala Gly Thr Lys Leu Glu Leu Lys
        115                 120                 125
```

<210> SEQ ID NO 56
<211> LENGTH: 127
<212> TYPE: PRT
<213> ORGANISM: Artificial Sequence
<220> FEATURE:
<223> OTHER INFORMATION: Synthetic Construct

<400> SEQUENCE: 56

```
Met Lys Phe Pro Ser Gln Leu Leu Leu Leu Leu Phe Gly Ile Pro
1               5                   10                  15

Gly Met Ile Cys Asp Ile Gln Met Thr Gln Ser Ser Ser Ser Phe Ser
                20                  25                  30

Val Ser Leu Gly Asp Arg Val Thr Ile Thr Cys Lys Ala Ser Glu Asp
            35                  40                  45

Ile Tyr Asn Arg Leu Ala Trp Tyr Gln Gln Lys Pro Gly Asn Ala Pro
        50                  55                  60

Arg Leu Leu Ile Ser Gly Ala Thr Ser Leu Glu Thr Gly Val Pro Ser
65                  70                  75                  80

Arg Phe Ser Gly Ser Gly Ser Gly Lys Asp Tyr Thr Leu Ser Ile Thr
                85                  90                  95

Ser Leu Gln Thr Glu Asp Val Ala Thr Tyr Tyr Cys Gln Gln Tyr Trp
            100                 105                 110

Ser Ile Leu Leu Thr Phe Gly Ala Gly Thr Lys Leu Glu Leu Lys
        115                 120                 125
```

<210> SEQ ID NO 57
<211> LENGTH: 27
<212> TYPE: DNA
<213> ORGANISM: Artificial Sequence
<220> FEATURE:
<223> OTHER INFORMATION: '14D6' antibody, heavy chain, CDR3
<220> FEATURE:
<221> NAME/KEY: CDS
<222> LOCATION: (1)..(27)

<400> SEQUENCE: 57

```
tgg gta ggg gac tgg tac ttc gat gtc                                    27
Trp Val Gly Asp Trp Tyr Phe Asp Val
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Construct

<400> SEQUENCE: 58

Trp Val Gly Asp Trp Tyr Phe Asp Val
1               5

<210> SEQ ID NO 59
<211> LENGTH: 408
<212> TYPE: DNA
<213> ORGANISM: Artificial Sequence
<220> FEATURE:
<223> OTHER INFORMATION: '14D6' antibody, heavy chain, variable region
<220> FEATURE:
<221> NAME/KEY: CDS
<222> LOCATION: (1)..(408)

<400> SEQUENCE: 59 atg aaa gtg ttg agt ctg ttg tac ctg ttg aca gcc att cct ggt atc       48
Met Lys Val Leu Ser Leu Leu Tyr Leu Leu Thr Ala Ile Pro Gly Ile
1               5                   10                  15 ctg tct gat gta cag ctt cag gag tca gga cct ggc ctc gtg aaa cct       96
Leu Ser Asp Val Gln Leu Gln Glu Ser Gly Pro Gly Leu Val Lys Pro
                20                  25                  30 tct cag tct ctg tct ctc acc tgc tct gtc act ggc tac tcc atc acc      144
Ser Gln Ser Leu Ser Leu Thr Cys Ser Val Thr Gly Tyr Ser Ile Thr
            35                  40                  45 agt ggt tat tac tgg aac tgg atc cgg cag ttt cca gga aac aaa ctg      192
Ser Gly Tyr Tyr Trp Asn Trp Ile Arg Gln Phe Pro Gly Asn Lys Leu
        50                  55                  60 gaa tgg atg ggc tac ata agc tac gac ggt agc aat aac tac aac cca      240
Glu Trp Met Gly Tyr Ile Ser Tyr Asp Gly Ser Asn Asn Tyr Asn Pro
65                  70                  75                  80 tct ctc aaa aat cga atc tcc atc act cgt gac aca tct aag aac cag      288
Ser Leu Lys Asn Arg Ile Ser Ile Thr Arg Asp Thr Ser Lys Asn Gln
                85                  90                  95 ttt ttc ctg aag ttg aat tct gtg act act gag gac aca gct aca tat      336
Phe Phe Leu Lys Leu Asn Ser Val Thr Thr Glu Asp Thr Ala Thr Tyr
                100                 105                 110 tac tgt gca aga tgg gta ggg gac tgg tac ttc gat gtc tgg ggc gca      384
Tyr Cys Ala Arg Trp Val Gly Asp Trp Tyr Phe Asp Val Trp Gly Ala
            115                 120                 125 ggg acc acg gtc acc gtc tcc tca                                      408
Gly Thr Thr Val Thr Val Ser Ser
        130                 135

<210> SEQ ID NO 60
<211> LENGTH: 136
<212> TYPE: PRT
<213> ORGANISM: Artificial Sequence
<220> FEATURE:
<223> OTHER INFORMATION: Synthetic Construct

<400> SEQUENCE: 60

Met Lys Val Leu Ser Leu Leu Tyr Leu Leu Thr Ala Ile Pro Gly Ile
1               5                   10                  15
```

```
Leu Ser Asp Val Gln Leu Gln Glu Ser Gly Pro Gly Leu Val Lys Pro
            20                  25                  30

Ser Gln Ser Leu Ser Leu Thr Cys Ser Val Thr Gly Tyr Ser Ile Thr
        35                  40                  45

Ser Gly Tyr Tyr Trp Asn Trp Ile Arg Gln Phe Pro Gly Asn Lys Leu
    50                  55                  60

Glu Trp Met Gly Tyr Ile Ser Tyr Asp Gly Ser Asn Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Thr Ala Thr Tyr
            100                 105                 110

Tyr Cys Ala Arg Trp Val Gly Asp Trp Tyr Phe Asp Val Trp Gly Ala
        115                 120                 125

Gly Thr Thr Val Thr Val Ser Ser
    130                 135

<210> SEQ ID NO 61
<211> LENGTH: 45
<212> TYPE: DNA
<213> ORGANISM: Artificial Sequence
<220> FEATURE:
<223> OTHER INFORMATION: '14D6' antibody, light chain, CDR1
<220> FEATURE:
<221> NAME/KEY: CDS
<222> LOCATION: (1)..(45)

<400> SEQUENCE: 61 agg gcc agc aaa agt gtc agt cca tct ggc tat agt tat atg cac      45
Arg Ala Ser Lys Ser Val Ser Pro Ser Gly Tyr Ser Tyr Met His
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic Construct

<400> SEQUENCE: 62

Arg Ala Ser Lys Ser Val Ser Pro Ser Gly Tyr Ser Tyr Met His
1               5                   10                  15

<210> SEQ ID NO 63
<211> LENGTH: 21
<212> TYPE: DNA
<213> ORGANISM: Artificial Sequence
<220> FEATURE:
<223> OTHER INFORMATION: '14D6' antibody, light chain, CDR2
<220> FEATURE:
<221> NAME/KEY: CDS
<222> LOCATION: (1)..(21)

<400> SEQUENCE: 63 ctt gca tcc aac cta gaa tct                                      21
Leu Ala Ser Asn Leu Glu Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic Construct
```

<400> SEQUENCE: 64

Leu Ala Ser Asn Leu Glu Ser
1               5

<210> SEQ ID NO 65
<211> LENGTH: 27
<212> TYPE: DNA
<213> ORGANISM: Artificial Sequence
<220> FEATURE:
<223> OTHER INFORMATION: '14D6' antibody, light chain, CDR3
<220> FEATURE:
<221> NAME/KEY: CDS
<222> LOCATION: (1)..(27)

<400> SEQUENCE: 65 cag cac agt agg gag ctt ccg ctc acg                                   27
Gln His Ser Arg Glu Leu Pro Leu Thr
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Gln His Ser Arg Glu Leu Pro Leu Thr
1               5

<210> SEQ ID NO 67
<211> LENGTH: 393
<212> TYPE: DNA
<213> ORGANISM: Artificial Sequence
<220> FEATURE:
<223> OTHER INFORMATION: '14D6' antibody, light chain, variable region
<220> FEATURE:
<221> NAME/KEY: CDS
<222> LOCATION: (1)..(393)

<400> SEQUENCE: 67 atg gag aca gac aca ctc ctg tta tgg gta ctg ctg ctc tgg gtt cca      48
Met Glu Thr Asp Thr Leu Leu Leu Trp Val Leu Leu Leu Trp Val Pro
1               5                   10                  15 ggt tcc act ggt gac att gtg ctg aca cag tct cct gct tcc tta gct      96
Gly Ser Thr Gly Asp Ile Val Leu Thr Gln Ser Pro Ala Ser Leu Ala
                20                  25                  30 gta tct ctg ggg cag agg gcc acc atc tca tgc agg gcc agc aaa agt     144
Val Ser Leu Gly Gln Arg Ala Thr Ile Ser Cys Arg Ala Ser Lys Ser
            35                  40                  45 gtc agt cca tct ggc tat agt tat atg cac tgg tac caa cag aaa cca     192
Val Ser Pro Ser Gly Tyr Ser Tyr Met His Trp Tyr Gln Gln Lys Pro
        50                  55                  60 gga cag cca ccc aaa ctc ctc atc tat ctt gca tcc aac cta gaa tct     240
Gly Gln Pro Pro Lys Leu Leu Ile Tyr Leu Ala Ser Asn Leu Glu Ser
65                  70                  75                  80 ggg gtc cct gcc agg ttc agt ggc agt ggg tct ggg aca gac ttc acc     288
Gly Val Pro Ala Arg Phe Ser Gly Ser Gly Ser Gly Thr Asp Phe Thr
                85                  90                  95 ctc aac atc cat cct gtg gag gag gag gat gct gca acc tat tac tgt     336
Leu Asn Ile His Pro Val Glu Glu Glu Asp Ala Ala Thr Tyr Tyr Cys
                100                 105                 110 cag cac agt agg gag ctt ccg ctc acg ttc ggt gct ggg acc aag ctg     384
Gln His Ser Arg Glu Leu Pro Leu Thr Phe Gly Ala Gly Thr Lys Leu

```
            115                 120                 125
gag ctg aaa                                                        393
Glu Leu Lys
    130

<210> SEQ ID NO 68
<211> LENGTH: 131
<212> TYPE: PRT
<213> ORGANISM: Artificial Sequence
<220> FEATURE:
<223> OTHER INFORMATION: Synthetic Construct

<400> SEQUENCE: 68

Met Glu Thr Asp Thr Leu Leu Leu Trp Val Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Arg Ala Ser Lys Ser
            35                  40                  45

Val Ser Pro Ser Gly Tyr Ser Tyr Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln His Ser Arg Glu Leu Pro Leu Thr Phe Gly Ala Gly Thr Lys Leu
        115                 120                 125

Glu Leu Lys
    130

<210> SEQ ID NO 69
<211> LENGTH: 21
<212> TYPE: DNA
<213> ORGANISM: Artificial Sequence
<220> FEATURE:
<223> OTHER INFORMATION: '18A2' antibody, heavy chain, CDR3
<220> FEATURE:
<221> NAME/KEY: CDS
<222> LOCATION: (1)..(21)

<400> SEQUENCE: 69 tgg gag ggg act act gac tac                                         21
Trp Glu Gly Thr Thr Asp Tyr
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic Construct

<400> SEQUENCE: 70

Trp Glu Gly Thr Thr Asp Tyr
1               5

<210> SEQ ID NO 71
<211> LENGTH: 402
<212> TYPE: DNA
<213> ORGANISM: Artificial Sequence
<220> FEATURE:
```

<223> OTHER INFORMATION: '18A2' antibody, heavy chain, variable region
<220> FEATURE:
<221> NAME/KEY: CDS
<222> LOCATION: (1)..(402)

<400> SEQUENCE: 71

```
atg aaa gtg ttg agt ctg ttg tac ctg ttg aca gcc att cct ggt atc      48
Met Lys Val Leu Ser Leu Leu Tyr Leu Leu Thr Ala Ile Pro Gly Ile
1               5                   10                  15 ctg tct gat gta cag ctt cag gag tca gga cct ggc ctc gtg aaa cct      96
Leu Ser Asp Val Gln Leu Gln Glu Ser Gly Pro Gly Leu Val Lys Pro
            20                  25                  30 tct cag tct ctg tct ctc acc tgc tct gtc act ggc tac tcc atc acc     144
Ser Gln Ser Leu Ser Leu Thr Cys Ser Val Thr Gly Tyr Ser Ile Thr
        35                  40                  45 agt ggt tat tac tgg aac tgg atc cgg cag ttt cca gga aac aaa ctg     192
Ser Gly Tyr Tyr Trp Asn Trp Ile Arg Gln Phe Pro Gly Asn Lys Leu
    50                  55                  60 gaa tgg atg ggc tac ata agc tac gac ggt agc aat aac tac aac cca     240
Glu Trp Met Gly Tyr Ile Ser Tyr Asp Gly Ser Asn Asn Tyr Asn Pro
65                  70                  75                  80 tct ctc aaa aat cga atc tcc atc act cgt gac aca tct aag aac cag     288
Ser Leu Lys Asn Arg Ile Ser Ile Thr Arg Asp Thr Ser Lys Asn Gln
                85                  90                  95 ttt ttc ctg aag ttg aat tct gtg act act gag gac aca gct aca tat     336
Phe Phe Leu Lys Leu Asn Ser Val Thr Thr Glu Asp Thr Ala Thr Tyr
            100                 105                 110 tac tgt gca aga tgg gag ggg act act gac tac tgg ggc caa ggc acc     384
Tyr Cys Ala Arg Trp Glu Gly Thr Thr Asp Tyr Trp Gly Gln Gly Thr
        115                 120                 125 act ctc aca gtc tcc tca                                              402
Thr Leu Thr Val Ser Ser
    130
```

<210> SEQ ID NO 72
<211> LENGTH: 134
<212> TYPE: PRT
<213> ORGANISM: Artificial Sequence
<220> FEATURE:
<223> OTHER INFORMATION: Synthetic Construct

<400> SEQUENCE: 72

```
Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Ser Val Thr Gly Tyr Ser Ile Thr
        35                  40                  45

Ser Gly Tyr Tyr Trp Asn Trp Ile Arg Gln Phe Pro Gly Asn Lys Leu
    50                  55                  60

Glu Trp Met Gly Tyr Ile Ser Tyr Asp Gly Ser Asn Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Thr Ala Thr Tyr
            100                 105                 110

Tyr Cys Ala Arg Trp Glu Gly Thr Thr Asp Tyr Trp Gly Gln Gly Thr
        115                 120                 125

Thr Leu Thr Val Ser Ser
    130
```

<210> SEQ ID NO 73
<211> LENGTH: 48
<212> TYPE: DNA
<213> ORGANISM: Artificial Sequence
<220> FEATURE:
<223> OTHER INFORMATION: '18A2' antibody, light chain, CDR1
<220> FEATURE:
<221> NAME/KEY: CDS
<222> LOCATION: (1)..(48)

<400> SEQUENCE: 73

```
aag tca agt cag agc ctc tta gat agt gat gga aag aca tat ttg aat      48
Lys Ser Ser Gln Ser Leu Leu Asp Ser Asp Gly Lys Thr Tyr Leu Asn
1               5                   10                  15
```

<210> SEQ ID NO 74
<211> LENGTH: 16
<212> TYPE: PRT
<213> ORGANISM: Artificial Sequence
<220> FEATURE:
<223> OTHER INFORMATION: Synthetic Construct

<400> SEQUENCE: 74

```
Lys Ser Ser Gln Ser Leu Leu Asp Ser Asp Gly Lys Thr Tyr Leu Asn
1               5                   10                  15
```

<210> SEQ ID NO 75
<211> LENGTH: 21
<212> TYPE: DNA
<213> ORGANISM: Artificial Sequence
<220> FEATURE:
<223> OTHER INFORMATION: '18A2' antibody, light chain, CDR2
<220> FEATURE:
<221> NAME/KEY: CDS
<222> LOCATION: (1)..(21)

<400> SEQUENCE: 75

```
ctg gtg tct aaa ctg gac tct                                          21
Leu Val Ser Lys Leu Asp Ser
1               5
```

<210> SEQ ID NO 76
<211> LENGTH: 7
<212> TYPE: PRT
<213> ORGANISM: Artificial Sequence
<220> FEATURE:
<223> OTHER INFORMATION: Synthetic Construct

<400> SEQUENCE: 76

```
Leu Val Ser Lys Leu Asp Ser
1               5
```

<210> SEQ ID NO 77
<211> LENGTH: 27
<212> TYPE: DNA
<213> ORGANISM: Artificial Sequence
<220> FEATURE:
<223> OTHER INFORMATION: '18A2' antibody, light chain, CDR3
<220> FEATURE:
<221> NAME/KEY: CDS
<222> LOCATION: (1)..(27)

<400> SEQUENCE: 77

```
tgg caa ggt aca cat ttt cct tac acg                                  27
Trp Gln Gly Thr His Phe Pro Tyr Thr
1               5
```

-continued

```
<210> SEQ ID NO 78
<211> LENGTH: 9
<212> TYPE: PRT
<213> ORGANISM: Artificial Sequence
<220> FEATURE:
<223> OTHER INFORMATION: Synthetic Construct

<400> SEQUENCE: 78

Trp Gln Gly Thr His Phe Pro Tyr Thr
1               5

<210> SEQ ID NO 79
<211> LENGTH: 393
<212> TYPE: DNA
<213> ORGANISM: Artificial Sequence
<220> FEATURE:
<223> OTHER INFORMATION: '18A2' antibody, light chain, variable region
<220> FEATURE:
<221> NAME/KEY: CDS
<222> LOCATION: (1)..(393)

<400> SEQUENCE: 79 atg agt cct gcc cag ttc ctg ttt ctg tta gtg ttc tgg att cgg gaa        48
Met Ser Pro Ala Gln Phe Leu Phe Leu Leu Val Phe Trp Ile Arg Glu
1               5                   10                  15 acc aac ggt gat gtt gtg atg acc cag act cca ctc act ttg tcg gtt        96
Thr Asn Gly Asp Val Val Met Thr Gln Thr Pro Leu Thr Leu Ser Val
                20                  25                  30 acc att gga caa cca gcc tcc atc tct tgc aag tca agt cag agc ctc       144
Thr Ile Gly Gln Pro Ala Ser Ile Ser Cys Lys Ser Ser Gln Ser Leu
            35                  40                  45 tta gat agt gat gga aag aca tat ttg aat tgg ttg tta cag agg cca       192
Leu Asp Ser Asp Gly Lys Thr Tyr Leu Asn Trp Leu Leu Gln Arg Pro
        50                  55                  60 ggc cag tct cca aag cgc cta atc tat ctg gtg tct aaa ctg gac tct       240
Gly Gln Ser Pro Lys Arg Leu Ile Tyr Leu Val Ser Lys Leu Asp Ser
65                  70                  75                  80 gga gtc cct gac agg ttc act ggc agt gga tca ggg aca gat ttc aca       288
Gly Val Pro Asp Arg Phe Thr Gly Ser Gly Ser Gly Thr Asp Phe Thr
                85                  90                  95 ctg aaa atc agc aga gtg gag gct gag gat ttg gga gtt tat tat tgc       336
Leu Lys Ile Ser Arg Val Glu Ala Glu Asp Leu Gly Val Tyr Tyr Cys
                100                 105                 110 tgg caa ggt aca cat ttt cct tac acg ttc ggg ggg ggg acc aag ctg       384
Trp Gln Gly Thr His Phe Pro Tyr Thr Phe Gly Gly Gly Thr Lys Leu
            115                 120                 125 gaa ata aaa                                                            393
Glu Ile Lys
    130

<210> SEQ ID NO 80
<211> LENGTH: 131
<212> TYPE: PRT
<213> ORGANISM: Artificial Sequence
<220> FEATURE:
<223> OTHER INFORMATION: Synthetic Construct

<400> SEQUENCE: 80

Met Ser Pro Ala Gln Phe Leu Phe Leu Leu Val Phe Trp Ile Arg Glu
1               5                   10                  15

Thr Asn Gly Asp Val Val Met Thr Gln Thr Pro Leu Thr Leu Ser Val
                20                  25                  30

Thr Ile Gly Gln Pro Ala Ser Ile Ser Cys Lys Ser Ser Gln Ser Leu
            35                  40                  45
```

Leu Asp Ser Asp Gly Lys Thr Tyr Leu Asn Trp Leu Leu Gln Arg Pro
    50                  55                  60

Gly Gln Ser Pro Lys Arg Leu Ile Tyr Leu Val Ser Lys Leu Asp Ser
65                  70                  75                  80

Gly Val Pro Asp Arg Phe Thr Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Trp Gln Gly Thr His Phe Pro Tyr Thr Phe Gly Gly Gly Thr Lys Leu
        115                 120                 125

Glu Ile Lys
    130

<210> SEQ ID NO 81
<211> LENGTH: 5238
<212> TYPE: DNA
<213> ORGANISM: Artificial Sequence
<220> FEATURE:
<223> OTHER INFORMATION: pFastBac1 plasmid

<400> SEQUENCE: 81

| | |
|---|---:|
| ttctctgtca cagaatgaaa attttttctgt catctcttcg ttattaatgt ttgtaattga | 60 |
| ctgaatatca acgcttattt gcagcctgaa tggcgaatgg gacgcgccct gtagcggcgc | 120 |
| attaagcgcg gcgggtgtgg tggttacgcg cagcgtgacc gctacacttg ccagcgccct | 180 |
| agcgcccgct cctttcgctt tcttcccttc ctttctcgcc acgttcgccg gctttccccg | 240 |
| tcaagctcta aatcggggc tcccttttagg gttccgattt agtgctttac ggcacctcga | 300 |
| ccccaaaaaa cttgattagg gtgatggttc acgtagtggg ccatcgccct gatagacggt | 360 |
| ttttcgccct ttgacgttgg agtccacgtt ctttaatagt ggactcttgt tccaaactgg | 420 |
| aacaacactc aaccctatct cggtctattc ttttgattta agggatttt tgccgatttc | 480 |
| ggcctattgg ttaaaaaatg agctgattta acaaaaattt aacgcgaatt ttaacaaaat | 540 |
| attaacgttt acaatttcag gtggcacttt tcggggaaat gtgcgcggaa cccctatttg | 600 |
| tttatttttc taaatacatt caaatatgta tccgctcatg agacaataac cctgataaat | 660 |
| gcttcaataa tattgaaaaa ggaagagtat gagtattcaa catttccgtg tcgcccttat | 720 |
| tcccttttt gcggcatttt gccttcctgt ttttgctcac ccagaaacgc tggtgaaagt | 780 |
| aaaagatgct gaagatcagt tgggtgcacg agtgggttac atcgaactgg atctcaacag | 840 |
| cggtaagatc cttgagagtt ttcgccccga agaacgtttt ccaatgatga gcacttttaa | 900 |
| agttctgcta tgtggcgcgg tattatcccg tattgacgcc gggcaagagc aactcggtcg | 960 |
| ccgcatacac tattctcaga atgacttggt tgagtactca ccagtcacag aaaagcatct | 1020 |
| tacggatggc atgacagtaa gagaattatg cagtgctgcc ataaccatga gtgataacac | 1080 |
| tgcggccaac ttacttctga caacgatcgg aggaccgaag gagctaaccg cttttttgca | 1140 |
| caacatgggg gatcatgtaa ctcgccttga tcgttgggaa ccggagctga atgaagccat | 1200 |
| accaaacgac gagcgtgaca ccacgatgcc tgtagcaatg gcaacaacgt tgcgcaaact | 1260 |
| attaactggc gaactactta ctctagcttc ccggcaacaa ttaatagact ggatggaggc | 1320 |
| ggataaagtt gcaggaccac ttctgcgctc ggcccttccg gctggctggt ttattgctga | 1380 |
| taaatctgga gccggtgagc gtgggtctcg cggtatcatt gcagcactgg ggccagatgg | 1440 |
| taagccctcc cgtatcgtag ttatctacac gacggggagt caggcaacta tggatgaacg | 1500 |

```
aaatagacag atcgctgaga taggtgcctc actgattaag cattggtaac tgtcagacca   1560
agtttactca tatatacttt agattgattt aaaacttcat ttttaattta aaaggatcta   1620
ggtgaagatc cttttttgata atctcatgac caaaatccct taacgtgagt tttcgttcca  1680
ctgagcgtca gacccgtag aaaagatcaa aggatcttct tgagatcctt ttttttctgcg   1740
cgtaatctgc tgcttgcaaa caaaaaaacc accgctacca gcggtggttt gtttgccgga   1800
tcaagagcta ccaactcttt ttccgaaggt aactggcttc agcagagcgc agataccaaa   1860
tactgtcctt ctagtgtagc cgtagttagg ccaccacttc aagaactctg tagcaccgcc   1920
tacataccte gctctgctaa tcctgttacc agtggctgct gccagtggcg ataagtcgtg   1980
tcttaccggg ttggactcaa gacgatagtt accggataag gcgcagcggt cgggctgaac   2040
ggggggttcg tgcacacagc ccagcttgga gcgaacgacc tacaccgaac tgagatacct   2100
acagcgtgag cattgagaaa gcgccacgct tcccgaaggg agaaaggcgg acaggtatcc   2160
ggtaagcggc agggtcggaa caggagagcg cacgagggag cttccagggg gaaacgcctg   2220
gtatctttat agtcctgtcg ggtttcgcca cctctgactt gagcgtcgat ttttgtgatg   2280
ctcgtcaggg gggcggagcc tatggaaaaa cgccagcaac gcggcctttt tacggttcct   2340
ggccttttgc tggccttttg ctcacatgtt ctttcctgcg ttatccctg attctgtgga    2400
taaccgtatt accgcctttg agtgagctga taccgctcgc cgcagccgaa cgaccgagcg   2460
cagcgagtca gtgagcgagg aagcggaaga gcgcctgatg cggtattttc tccttacgca   2520
tctgtgcggt atttcacacc gcagaccagc cgcgtaacct ggcaaaatcg gttacggttg   2580
agtaataaat ggatgccctg cgtaagcggg tgtgggcgga caataaagtc ttaaactgaa   2640
caaaatagat ctaaactatg acaataaagt cttaaactag acagaatagt tgtaaactga   2700
aatcagtcca gttatgctgt gaaaaagcat actggacttt tgttatggct aaagcaaact   2760
cttcattttc tgaagtgcaa attgcccgtc gtattaaaga ggggcgtggc caagggcatg   2820
gtaaagacta tattcgcggc gttgtgacaa tttaccgaac aactccgcgg ccgggaagcc   2880
gatctcggct tgaacgaatt gttaggtggc ggtacttggg tcgatatcaa agtgcatcac   2940
ttcttcccgt atgcccaact ttgtatagag agccactgcg gatcgtcac cgtaatctgc    3000
ttgcacgtag atcacataag caccaagcgc gttggcctca tgcttgagga gattgatgag   3060
cgcggtggca atgccctgcc tccggtgctc gccggagact gcgagatcat agatatagat   3120
ctcactacgc ggctgctcaa acctgggcag aacgtaagcc gcgagagcgc caacaaccgc   3180
ttcttggtcg aaggcagcaa gcgcgatgaa tgtcttacta cggagcaagt tcccgaggta   3240
atcggagtcc ggctgatgtt gggagtaggt ggctacgtct ccgaactcac gaccgaaaag   3300
atcaagagca gcccgcatgg atttgacttg gtcagggccg agcctacatg tgcgaatgat   3360
gcccatactt gagccaccta actttgtttt agggcgactg ccctgctgcg taacatcgtt   3420
gctgctgcgt aacatcgttg ctgctccata acatcaaaca tcgacccacg cgtaacgcg    3480
cttgctgctt ggatgcccga ggcatagact gtacaaaaaa acagtcataa caagccatga   3540
aaaccgccac tgcgccgtta ccaccgctgc gttcggtcaa ggttctggac cagttgcgtg   3600
agcgcatacg ctacttgcat tacagtttac gaaccgaaca ggcttatgtc aactgggttc   3660
gtgccttcat ccgtttccac ggtgtgcgtc acccggcaac cttgggcagc agcgaagtcg   3720
aggcatttct gtcctggctg gcgaacgagc gcaaggtttc ggtctccacg catcgtcagg   3780
cattggcggc cttgctgttc ttctacggca aggtgctgtg cacggatctg ccctggcttc   3840
aggagatcgg tagacctcgg ccgtcgcggc gcttgccggt ggtgctgacc ccggatgaag   3900
```

```
tggttcgcat cctcggtttt ctggaaggcg agcatcgttt gttcgcccag gactctagct    3960
atagttctag tggttggcct acgtacccgt agtggctatg caggggcttg ccgcccgac     4020
gttggctgcg agccctgggc cttcacccga acttgggggt tggggtgggg aaaaggaaga    4080
aacgcgggcg tattggtccc aatggggtct cggtggggta tcgacagagt gccagccctg    4140
ggaccgaacc ccgcgtttat gaacaaacga cccaacaccc gtgcgtttta ttctgtcttt    4200
ttattgccgt catagcgcgg gttccttccg gtattgtctc cttccgtgtt tcagttagcc    4260
tcccccatct cccggtaccg catgctatgc atcagctgct agcaccatgg ctcgagatcc    4320
cgggtgatca gtcttcgtc gagtgattgt aaataaaatg taatttacag tatagtattt     4380
taattaatat acaaatgatt tgataataat tcttatttaa ctataatata ttgtgttggg    4440
ttgaattaaa ggtccgtata ctccggaata ttaatagatc atggagataa ttaaaatgat    4500
aaccatctcg caaataaata agtatttac tgttttcgta acagttttgt aataaaaaaa     4560
cctataaata ttccggatta ttcataccgt cccaccatcg ggcgcggatc ccggtccgaa    4620
gcgcgcggaa ttcaaaggcc tacgtcgacg agctcactag tcgcggccgc tttcgaatct    4680
agagcctgca gtctcgacaa gcttgtcgag aagtactaga ggatcataat cagccatacc    4740
acatttgtag aggttttact tgctttaaaa aacctcccac acctccccct gaacctgaaa    4800
cataaaatga atgcaattgt tgttgttaac ttgtttattg cagcttataa tggttacaaa    4860
taaagcaata gcatcacaaa tttcacaaat aaagcatttt tttcactgca ttctagttgt    4920
ggtttgtcca aactcatcaa tgtatcttat catgtctgga tctgatcact gcttgagcct    4980
aggagatccg aaccagataa gtgaaatcta gttccaaact attttgtcat ttttaattt      5040
cgtattagct tacgacgcta cacccagttc ccatctattt tgtcactctt ccctaaataa    5100
tccttaaaaa ctccatttcc acccctccca gttcccaact attttgtccg cccacagcgg    5160
ggcattttc ttcctgttat gttttaatc aaacatcctg ccaactccat gtgacaaacc      5220
gtcatcttcg gctactttt                                                  5238
```

<210> SEQ ID NO 82
<211> LENGTH: 6442
<212> TYPE: DNA
<213> ORGANISM: Artificial Sequence
<220> FEATURE:
<223> OTHER INFORMATION: pIIIw plasmide
<220> FEATURE:
<221> NAME/KEY: misc_feature
<222> LOCATION: (5086)..(5086)
<223> OTHER INFORMATION: n is a, c, g, or t

<400> SEQUENCE: 82

```
ccctgcaggg cctgaaataa cctctgaaag aggaacttgg ttaggtacct gtggaatgtg     60
tgtcagttag ggtgtggaaa gtccccaggc tccccagcag gcagaagtat gcaaagcatg    120
catctcaatt agtcagcaac caggtgtgga aagtccccag gctccccagc aggcagaagt    180
atgcaaagca tgcatctcaa ttagtcagca accatagtcc cgcccctaac tccgcccatc    240
ccgcccctaa ctccgcccag ttccgcccat tctccgcccc atggctgact aatttttttt    300
atttatacag aggccgaggc cgcctcggcc tctgagctat tccagaagta gtgaggaggc    360
ttttttggag gcctaggctt ttgcaaaaag cttgattggg atccaccggt cgccaccatg    420
gtgagcaagg gcgaggagct gttcaccggg gtggtgccca tcctggtcga gctggacggc    480
gacgtaaacg gccacaagtt cagcgtgtcc ggcgagggcg agggcgatgc cacctacggc    540
```

```
aagctgaccc tgaagttcat ctgcaccacc ggcaagctgc ccgtgccctg gcccacccttc    600
gtgaccaccc tgacctacgg cgtgcagtgc ttcagccgct accccgacca catgaagcag    660
cacgacttct tcaagtccgc catgcccgaa ggctacgtcc aggagcgcac catcttcttc    720
aaggacgacg gcaactacaa gacccgcgcc gaggtgaagt tcgagggcga caccctggtg    780
aaccgcatcg agctgaaggg catcgacttc aaggaggacg gcaacatcct ggggcacaag    840
ctggagtaca actacaacag ccacaacgtc tatatcatgg ccgacaagca gaagaacggc    900
atcaaggtga acttcaagat ccgccacaac atcgaggacg gcagcgtgca gctcgccgac    960
cactaccagc agaacccccc catcggcgac ggccccgtgc tgctgcccga caaccactac   1020
ctgagcaccc agtccgccct gagcaaagac cccaacgaga agcgcgatca catggtcctg   1080
ctggagttcg tgaccgccgc cgggatcact ctcggcatgg acgagctgta caagtaaagc   1140
ggccgcttcg agcagacatg ataagataca ttgatgagtt tggacaaacc acaactagaa   1200
tgcagtgaaa aaaatgcttt atttgtgaaa tttgtgatgc tattgcttta tttgtaacca   1260
ttataagctg caataaacaa gttaacaaca acaattgcat tcattttatg tttcaggttc   1320
agggggaggt gtgggaggtt ttttaaagca agtaaaacct ctacaaatgt ggtaaaatcg   1380
ataaggatcc gggctggcgt aatagcgaag aggcccgcac cgatcgccct tcccaacagt   1440
tgcggtggag aagagcatgc gtgaggctcc ggtgcccgtc agtgggcaga gcgcacatcg   1500
cccacagtcc ccgagaagtt ggggggaggg tcggcaatt gaaccggtgc ctagagaagg   1560
tggcgcgggg taaactggga aagtgatgtc gtgtactggc tccgcccttt tcccgagggt   1620
gggggagaac cgtatataag tgcagtagtc gctgtgaacg ttcttttcg caacgggttt   1680
gccgccagaa cacaggtaag tgccgtgtgt ggttcccgcg ggcctggcct ctttacgggt   1740
tatgccccctt gcgtgccttg aattacttcc acctggctgc agtacgtgat tcttgatccc   1800
gagcttcggg ttggaagtgg gtgggagagt tcgaggcctt gcgcttaagg agccccttcg   1860
cctcgtgctt gagttgaggc ctggcctggg cgctggggcc gccgcgtgcg aatctggtgg   1920
caccttcgcg cctgtctcgc tgctttcgat aagtctctag ccatttaaaa ttttttgatga   1980
cctgctgcga cgcttttttt ctggcaagat agtcttgtaa atgcgggcca agatctgcac   2040
actggtatttt cggttttttgg ggccgcgggc ggcgacgggg cccgtgcgtc ccagcgcaca   2100
tgttcggcga ggcggggcct gcgagcgcgg ccaccgagaa tcggacgggg gtagtctcaa   2160
gctggccggc ctgctctggt gcctggcctc gcgccgccgt gtatcgcccc gccctgggcg   2220
gcaaggctgg cccggtcggc accagttgcg tgagcggaaa gatggccgct tcccggccct   2280
gctgcaggga gctcaaaatg gaggacgcgg cgctcgggag agcgggcggg tgagtcaccc   2340
acacaaagga aaagggcctt tccgtcctca gccgtcgctt catgtgactc cacgagtac    2400
cgggcgccgt ccaggcacct cgattagttc tcgagctttt ggagtacgtc gtctttaggt    2460
tggggggagg ggttttatgc gatggagttt ccccacactg agtgggtgga gactgaagtt    2520
aggccagctt ggcacttgat gtaattctcc ttggaatttg ccctttttga gtttggatct    2580
tggttcattc tcaagcctca gacagtggtt caaagttttt ttcttccatt tcaggtgtcg    2640
tgaggaattc tctagagctt gatcaaacaa gtttgtacaa aaaagcaggc tccgagaaa     2700
acctgtattt tcagggcatg gcacccacaa agcgcaaggg cgaatgcccc ggcgccgccc    2760
caaagaaacc caaggagcca gtccaggtcc ccaagttgct gatcaagggc ggcgtggagg    2820
tcctggaggt caagaccggc gtggacgcca tcaccgaggt ggagtgtttc ttgaaccccg    2880
agatgggcga ccccgacgac catctgcgcg ggtacagcca gcacctgacc gccgagaacg    2940
```

```
cattcgattc cgactcaccc gataagaaga tgttgccatg ctattccacc gcccgcatcc    3000
cactgcccaa cctcaacgaa gacttgacat gcggcaacct gctgatgtgg gaagccgtca    3060
ccgtgaagac cgaagtcatc ggcatcacct ccatgttgaa tctgcacgcc ggaagccaaa    3120
aggtgcacga gaacggcggc gggaagcccg tccaggggtc aaacttccat ttcttcgccg    3180
tcggcggcga tccactcgag atgcaaggcg tgttgatgaa ctatcgcacc aagtatcccc    3240
aaggcaccat cacacccaag aacccaaccg cccaaagtca ggtcatgaac accgatcaca    3300
aagcatatct cgataagaat aacgcctacc ccgtcgagtg ttggatcccc gatccatcca    3360
agaacgagaa caccegetac ttcggcacct ataccggcgg cgagaacgtc ccacccgtgt    3420
tgcacgtgac aaataccgcc acaaccgtcc tgctcgacga gcaaggcgtc ggcccactct    3480
gcaaggcaga cagcctctac gtcagcgccg ccgacatctg cggactgttc accaattcaa    3540
gcggcaccca gcaatggcgc gggttggccc gctacttcaa aatcaggctc cgcaagcgca    3600
gcgtgaagaa tccctatcca atcagttttcc tgctgtccga tttgatcaat cgccgcacac    3660
aaaaggtcga cggccagccc atgtacggca tggaaagcca agtcgaagaa gtgcgcgtct    3720
tcgacgggac cgagcagttg cccggcgatc ccgacatgat ccgctacatc gatcgccaag    3780
gccagctcca aaccaagatg gtctgagcct aggacccagc tttcttgtac aaagtggttc    3840
gatctagaat ggctagtgga tccccgggc tgcaggaatt cgatatcaag cttatcgata    3900
atcaacctct ggattacaaa atttgtgaaa gattgactgg tattcttaac tatgttgctc    3960
cttttacgct atgtggatac gctgctttaa tgcctttgta tcatgctatt gcttcccgta    4020
tggctttcat tttctcctcc ttgtataaat cctggttgct gtctctttat gaggagttgt    4080
ggcccgttgt caggcaacgt ggcgtggtgt gcactgtgtt tgctgacgca acccccactg    4140
gttggggcat tgccaccacc tgtcagctcc tttccgggac tttcgctttc ccctccccta    4200
ttgccacggc ggaactcatc gccgcctgcc ttgcccgctg ctggacaggg gctcggctgt    4260
tgggcactga caattccgtg tgtgttgtcg ggaaatcatc gtcctttcct ggctgctcg    4320 cctgtgttgc cacctggatt ctgcgcggga cgtccttctg ctacgtccct tcggccctca    4380
atccagcgga ccttccttcc cgcggcctgc tgccggctct gcggcctctt ccgcgtcttc    4440
gccttcgccc tcagacgagt cggatctccc tttgggccgc ctccccgcat cgataccgtc    4500
gggccactgc tccctaaacc tgagctagca ttatccctaa tacctgccac cccactctta    4560
atcagtggtg gaagaacggt ctcagaactg tttgtttcaa ttggccatttt aagtttagta    4620 gtaaagact ggttaatgat aacaatgcat cgtaaaacct tcagaaggaa aggagaatgt    4680
tttgtggacc actttggttt tcttttttgc gtgtggcagt tttaagttat tagtttttaa    4740
aatcagtact ttttaatgga aacaacttga ccaaaaattt gtcacagaat tttgagaccc    4800
attaaaaaag ttaaatgaga aacctgtgtg ttccttttggt caacaccgag acatttaggt    4860
gaaagacatc taattctggt tttacgaatc tggaaacttc ttgaaaatgt aattcttgag    4920
ttaacacttc tgggtggaga atagggttgt tttccccca cataattgga aggggaagga    4980
atatcattta aagctatggg agggtttctt tgattacaac actggagaga atgcagcat    5040 gttgctgatt gcctgtcact aaaacaggcc aaaaactgag tccttngggt tgcatagaaa    5100
gcttcatgtt gctaaaccaa tgttaagtga atctttggaa acaaaatgtt tccaaattac    5160
tgggatgtgc atgttgaaac gtgggttaat taactagcca tgaccaaaat cccttaacgt    5220
gagttttcgt tccactgagc gtcagacccc gtagaaaaga tcaaaggatc ttcttgagat    5280
```

```
ccttttttc  tgcgcgtaat  ctgctgcttg  caaacaaaaa  aaccaccgct  accagcggtg    5340
gtttgtttgc  cggatcaaga  gctaccaact  cttttttccga aggtaactgg  cttcagcaga    5400
gcgcagatac  caaatactgt  tcttctagtg  tagccgtagt  taggccacca  cttcaagaac    5460
tctgtagcac  cgcctacata  cctcgctctg  ctaatcctgt  taccagtggc  tgctgccagt    5520
ggcgataagt  cgtgtcttac  cgggttggac  tcaagacgat  agttaccgga  taaggcgcag    5580
cggtcgggct  gaacggggg   ttcgtgcaca  cagcccagct  tggagcgaac  gacctacacc    5640
gaactgagat  acctacagcg  tgagctatga  gaaagcgcca  cgcttcccga  agggagaaag    5700
gcggacaggt  atccggtaag  cggcagggtc  ggaacaggag  agcgcacgag  ggagcttcca    5760
gggggaaacg  cctggtatct  ttatagtcct  gtcgggtttc  gccacctctg  acttgagcgt    5820
cgatttttgt  gatgctcgtc  aggggggcgg  agcctatgga  aaaacgccag  caacgcggcc    5880
tttttacggt  tcctggcctt  ttgctggcct  tttgctcaca  tgttcttaat  taaatttttc    5940
aaaagtagtt  gacaattaat  catcggcata  gtatatcggc  atagtataat  acgactcact    6000
ataggagggc  catcatggcc  aagttgacca  gtgctgtccc  agtgctcaca  gcagggatg    6060 tggctggagc  tgttgagttc  tggactgaca  ggttggggtt  ctccagagat  tttgtggagg    6120
atgactttgc  aggtgtggtc  agagatgatg  tcaccctgtt  catctcagca  gtccaggacc    6180
aggtggtgcc  tgacaacacc  ctggcttggg  tgtgggtgag  aggactggat  gagctgtatg    6240
ctgagtggag  tgaggtggtc  tccaccaact  tcagggatgc  cagtggccct  gccatgacag    6300
agattggaga  gcagccctgg  gggagagagt  ttgccctgag  agacccagca  ggcaactgtg    6360
tgcactttgt  ggcagaggag  caggactgag  gataagaatt  gtaacaaaaa  accccgcccc    6420 ggcgggttt   tttgttaatt  aa                                                 6442
```

<210> SEQ ID NO 83
<211> LENGTH: 4242
<212> TYPE: DNA
<213> ORGANISM: Artificial Sequence
<220> FEATURE:
<223> OTHER INFORMATION: pGL4.10 plasmide

<400> SEQUENCE: 83

```
ggcctaactg  gccggtacct  gagctcgcta  gcctcgagga  tatcaagatc  tggcctcggc     60
ggccaagctt  ggcaatccgg  tactgttggt  aaagccacca  tggaagatgc  caaaaacatt    120
aagaagggcc  cagcgccatt  ctacccactc  gaagacggga  ccgccggcga  gcagctgcac    180
aaagccatga  agcgctacgc  cctggtgccc  ggcaccatcg  cctttaccga  cgcacatatc    240
gaggtggaca  ttacctacgc  cgagtacttc  gagatgagcg  ttcggctggc  agaagctatg    300
aagcgctatg  ggctgaatac  aaaccatcgg  atcgtggtgt  gcagcgagaa  tagcttgcag    360
ttcttcatgc  ccgtgttggg  tgccctgttc  atcggtgtgg  ctgtggcccc  agctaacgac    420
atctacaacg  agcgcgagct  gctgaacagc  atgggcatca  gccagcccac  cgtcgtattc    480
gtgagcaaga  aagggctgca  aaagatcctc  aacgtgcaaa  agaagctacc  gatcatacaa    540
aagatcatca  tcatggatag  caagaccgac  taccagggct  tccaaagcat  gtacaccttc    600
gtgacttccc  atttgccacc  cggcttcaac  gagtacgact  tcgtgcccga  gagcttcgac    660
cgggacaaaa  ccatcgccct  gatcatgaac  agtagtggca  gtaccggatt  gcccaagggc    720
gtagccctac  cgcaccgcac  cgcttgtgtc  cgattcagtc  atgcccgcga  ccccatcttc    780
ggcaaccaga  tcatccccga  caccgctatc  ctcagcgtgg  tgccatttca  ccacggcttc    840
ggcatgttca  ccacgctggg  ctacttgatc  tgcggctttc  gggtcgtgct  catgtaccgc    900
```

```
ttcgaggagg agctattctt gcgcagcttg caagactata agattcaatc tgccctgctg    960
gtgcccacac tatttagctt cttcgctaag agcactctca tcgacaagta cgacctaagc   1020
aacttgcacg agatcgccag cggcggggcg ccgctcagca aggaggtagg tgaggccgtg   1080
gccaaacgct tccacctacc aggcatccgc cagggctacg gcctgacaga acaaccagc    1140
gccattctga tcaccccga aggggacgac aagcctggcg cagtaggcaa ggtggtgccc    1200
ttcttcgagg ctaaggtggt ggacttggac accggtaaga cactgggtgt gaaccagcgc   1260
ggcgagctgt gcgtccgtgg ccccatgatc atgagcggct acgttaacaa ccccgaggct   1320
acaaacgctc tcatcgacaa ggacggctgg ctgcacagcg cgacatcgc ctactgggac    1380
gaggacgagc acttcttcat cgtggaccgg ctgaagagcc tgatcaaata cagggctac    1440
caggtagccc cagccgaact ggagagcatc ctgctgcaac accccaacat cttcgacgcc   1500
ggggtcgccg gcctgcccga cgacgatgcc ggcgagctgc ccgccgcagt cgtcgtgctg   1560
gaacacggta aaaccatgac cgagaaggag atcgtggact atgtggccag ccaggttaca   1620
accgccaaga agctgcgcgg tggtgttgtg ttcgtggacg aggtgcctaa aggactgacc   1680
ggcaagttgg acgcccgcaa gatccgcgag attctcatta aggccaagaa gggcggcaag   1740
atcgccgtgt aataattcta gagtcggggc ggccggccgc ttcgagcaga catgataaga   1800
tacattgatg agtttggaca aaccacaact agaatgcagt gaaaaaaatg ctttatttgt   1860
gaaatttgtg atgctattgc tttatttgta accattataa gctgcaataa acaagttaac   1920
aacaacaatt gcattcattt tatgtttcag gttcaggggg aggtgtggga ggttttttaa   1980
agcaagtaaa acctctacaa atgtggtaaa atcgataagg atccgtcgac cgatgccctt   2040
gagagccttc aacccagtca gctccttccg gtgggcgcgg ggcatgacta tcgtcgccgc   2100
acttatgact gtcttcttta tcatgcaact cgtaggacag gtgccggcag cgctcttccg   2160
cttcctcgct cactgactcg ctgcgctcgg tcgttcggct gcggcgagcg gtatcagctc   2220
actcaaaggc ggtaatacgg ttatccacag aatcagggga taacgcagga agaacatgt    2280
gagcaaaagg ccagcaaaag gccaggaacc gtaaaaaggc cgcgttgctg gcgttttcc    2340
ataggctccg cccccctgac gagcatcaca aaaatcgacg ctcaagtcag aggtggcgaa   2400
acccgacagg actataaaga taccaggcgt ttccccctgg aagctccctc gtgcgctctc   2460
ctgttccgac cctgccgctt accggatacc tgtccgcctt tctcccttcg ggaagcgtgg   2520
cgctttctca tagctcacgc tgtaggtatc tcagttcggt gtaggtcgtt cgctccaagc   2580
tgggctgtgt gcacgaaccc cccgttcagc ccgaccgctg cgccttatcc ggtaactatc   2640
gtcttgagtc caacccggta agacacgact tatcgccact ggcagcagcc actggtaaca   2700
ggattagcag agcgaggtat gtaggcgtg ctacagagtt cttgaagtgg tggcctaact    2760
acggctacac tagaagaaca gtatttggta tctgcgctct gctgaagcca gttaccttcg   2820
gaaaaagagt tggtagctct tgatccggca aacaaaccac cgctggtagc ggtggttttt   2880
ttgtttgcaa gcagcagatt acgcgcagaa aaaaggatc tcaagaagat cctttgatct   2940
tttctacggg gtctgacgct cagtggaacg aaaactcacg ttaagggatt ttggtcatga   3000
gattatcaaa aaggatcttc acctagatcc ttttaaatta aaaatgaagt tttaaatcaa   3060
tctaaagtat atatgagtaa acttggtctg acagcggccg caaatgctaa accactgcag   3120
tggttaccag tgcttgatca gtgaggcacc gatctcagcg atctgcctat ttcgttcgtc   3180
catagtggcc tgactccccg tcgtgtagat cactacgatt cgtgagggct taccatcagg   3240
```

```
cccagcgca gcaatgatgc cgcgagagcc gcgttcaccg gcccccgatt tgtcagcaat    3300
gaaccagcca gcagggaggg ccgagcgaag aagtggtcct gctactttgt ccgcctccat    3360
ccagtctatg agctgctgtc gtgatgctag agtaagaagt tcgccagtga gtagtttccg    3420
aagagttgtg gccattgcta ctggcatcgt ggtatcacgc tcgtcgttcg gtatggcttc    3480
gttcaactct ggttcccagc ggtcaagccg ggtcacatga tcacccatat tatgaagaaa    3540
tgcagtcagc tccttagggc ctccgatcgt tgtcagaagt aagttggccg cggtgttgtc    3600
gctcatggta atggcagcac tacacaattc tcttaccgtc atgccatccg taagatgctt    3660
ttccgtgacc ggcgagtact caaccaagtc gttttgtgag tagtgtatac ggcgaccaag    3720
ctgctcttgc ccggcgtcta tacgggacaa caccgcgcca catagcagta ctttgaaagt    3780
gctcatcatc gggaatcgtt cttcggggcg gaaagactca aggatcttgc cgctattgag    3840
atccagttcg atatagccca ctcttgcacc cagttgatct tcagcatctt ttactttcac    3900
cagcgtttcg gggtgtgcaa aaacaggcaa gcaaatgcc gcaagaagg gaatgagtgc       3960 gacacgaaaa tgttggatgc tcatactcgt cctttttcaa tattattgaa gcatttatca    4020
gggttactag tacgtctctc aaggataagt aagtaatatt aaggtacggg aggtattgga    4080
caggccgcaa taaatatct ttattttcat tacatctgtg tgttggtttt ttgtgtgaat      4140
cgatagtact aacatacgct ctccatcaaa acaaaacgaa acaaaacaaa ctagcaaaat    4200
aggctgtccc cagtgcaagt gcaggtgcca gaacatttct ct                        4242
```

```
<210> SEQ ID NO 84
<211> LENGTH: 1065
<212> TYPE: DNA
<213> ORGANISM: JC virus
<220> FEATURE:
<221> NAME/KEY: CDS
<222> LOCATION: (1)..(1065)
<223> OTHER INFORMATION: VP-1 gene

<400> SEQUENCE: 84 atg gcc cca aca aaa aga aaa gga gaa agg aag gac ccc gtg caa gtt        48
Met Ala Pro Thr Lys Arg Lys Gly Glu Arg Lys Asp Pro Val Gln Val
1               5                   10                  15 cca aaa ctt ctt ata aga gga gga gta gaa gtt cta gaa gtt aaa act       96
Pro Lys Leu Leu Ile Arg Gly Gly Val Glu Val Leu Glu Val Lys Thr
                20                  25                  30 ggg gtt gac tca att aca gag gta gaa tgc ttt tta act cca gaa atg      144
Gly Val Asp Ser Ile Thr Glu Val Glu Cys Phe Leu Thr Pro Glu Met
            35                  40                  45 ggt gac cca gat gag cat ctt agg ggt ttt agt aag tca ata tct ata      192
Gly Asp Pro Asp Glu His Leu Arg Gly Phe Ser Lys Ser Ile Ser Ile
        50                  55                  60 tca gat aca ttt gaa agt gac tcc cca aat agg gac atg ctt cct tgt      240
Ser Asp Thr Phe Glu Ser Asp Ser Pro Asn Arg Asp Met Leu Pro Cys
65                  70                  75                  80 tac agt gtg gcc aga att cca cta ccc aat cta aat gag gat cta acc      288
Tyr Ser Val Ala Arg Ile Pro Leu Pro Asn Leu Asn Glu Asp Leu Thr
                85                  90                  95 tgt gga aat ata ctc atg tgg gag gct gtg acc tta aaa act gag gtt      336
Cys Gly Asn Ile Leu Met Trp Glu Ala Val Thr Leu Lys Thr Glu Val
                100                 105                 110 ata ggg gtg aca agt ttg atg aat gtg cac tct aat ggg caa gca act      384
Ile Gly Val Thr Ser Leu Met Asn Val His Ser Asn Gly Gln Ala Thr
            115                 120                 125 cat gac aat ggt gca ggg aag cca gtg cag ggc acc agc ttt cat ttt      432
```

```
                His Asp Asn Gly Ala Gly Lys Pro Val Gln Gly Thr Ser Phe His Phe
                    130                 135                 140 ttt tct gtt ggg ggg gag gct tta gaa tta cag ggg gtg ctt ttt aat             480
Phe Ser Val Gly Gly Glu Ala Leu Glu Leu Gln Gly Val Leu Phe Asn
145                 150                 155                 160 tac aga aca aag tac cca gat gga aca att ttt cca aag aat gcc aca             528
Tyr Arg Thr Lys Tyr Pro Asp Gly Thr Ile Phe Pro Lys Asn Ala Thr
                    165                 170                 175 gtg caa tct caa gtc atg aac aca gag cac aag gcg tac cta gat aag             576
Val Gln Ser Gln Val Met Asn Thr Glu His Lys Ala Tyr Leu Asp Lys
                180                 185                 190 aac aaa gca tat cct gtt gaa tgt tgg gtt cct gat ccc acc aga aat             624
Asn Lys Ala Tyr Pro Val Glu Cys Trp Val Pro Asp Pro Thr Arg Asn
            195                 200                 205 gaa aac aca aga tat ttt ggg aca cta aca gga gaa aat gtt cct                 672
Glu Asn Thr Arg Tyr Phe Gly Thr Leu Thr Gly Gly Glu Asn Val Pro
        210                 215                 220 cca gtt ctt cat ata aca aac act gcc aca aca gtg ttg ctt gat gaa             720
Pro Val Leu His Ile Thr Asn Thr Ala Thr Thr Val Leu Leu Asp Glu
225                 230                 235                 240 ttt ggt gtt ggg cca ctt tgc aaa ggt gac aac tta tac ttg tca gct             768
Phe Gly Val Gly Pro Leu Cys Lys Gly Asp Asn Leu Tyr Leu Ser Ala
                245                 250                 255 gtt gat gtc tgt ggc atg ttt aca aac agg tct ggt tcc cag cag tgg             816
Val Asp Val Cys Gly Met Phe Thr Asn Arg Ser Gly Ser Gln Gln Trp
            260                 265                 270 aga gga ctc tcc aga tat ttt aag gtg cag cta agg aaa agg agg gtt             864
Arg Gly Leu Ser Arg Tyr Phe Lys Val Gln Leu Arg Lys Arg Arg Val
        275                 280                 285 aaa aac ccc tac cca att tct ttc ctt ctt act gat tta att aac aga             912
Lys Asn Pro Tyr Pro Ile Ser Phe Leu Leu Thr Asp Leu Ile Asn Arg
290                 295                 300 agg act cct aga gtt gat ggg cag cct atg tat ggc atg gat gct caa             960
Arg Thr Pro Arg Val Asp Gly Gln Pro Met Tyr Gly Met Asp Ala Gln
305                 310                 315                 320 gta gag gag gtt aga gtt ttt gag gga aca gag gag ctt cca ggg gac            1008
Val Glu Glu Val Arg Val Phe Glu Gly Thr Glu Glu Leu Pro Gly Asp
                325                 330                 335 cca gac atg atg aga tac gtt gac aaa tat gga cag ttg cag aca aaa            1056
Pro Asp Met Met Arg Tyr Val Asp Lys Tyr Gly Gln Leu Gln Thr Lys
            340                 345                 350 atg ctg taa                                                                1065
Met Leu <210> SEQ ID NO 85
<211> LENGTH: 354
<212> TYPE: PRT
<213> ORGANISM: JC virus

<400> SEQUENCE: 85

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
                20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
        50                  55                  60

Ser Asp Thr Phe Glu Ser Asp Ser Pro Asn Arg Asp Met Leu Pro Cys
```

```
                65                  70                  75                  80
        Tyr Ser Val Ala Arg Ile Pro Leu Pro Asn Leu Asn Glu Asp Leu Thr
                            85                  90                  95

Cys Gly Asn Ile Leu Met Trp Glu Ala Val Thr Leu Lys Thr Glu Val
                            100                 105                 110

Ile Gly Val Thr Ser Leu Met Asn Val His Ser Asn Gly Gln Ala Thr
                            115                 120                 125

His Asp Asn Gly Ala Gly Lys Pro Val Gln Gly Thr Ser Phe His Phe
                    130                 135                 140

Phe Ser Val Gly Gly Glu Ala Leu Glu Leu Gln Gly Val Leu Phe Asn
        145                 150                 155                 160

Tyr Arg Thr Lys Tyr Pro Asp Gly Thr Ile Phe Pro Lys Asn Ala Thr
                            165                 170                 175

Val Gln Ser Gln Val Met Asn Thr Glu His Lys Ala Tyr Leu Asp Lys
                            180                 185                 190

Asn Lys Ala Tyr Pro Val Glu Cys Trp Val Pro Asp Pro Thr Arg Asn
                            195                 200                 205

Glu Asn Thr Arg Tyr Phe Gly Thr Leu Thr Gly Gly Glu Asn Val Pro
                    210                 215                 220

Pro Val Leu His Ile Thr Asn Thr Ala Thr Thr Val Leu Leu Asp Glu
        225                 230                 235                 240

Phe Gly Val Gly Pro Leu Cys Lys Gly Asp Asn Leu Tyr Leu Ser Ala
                            245                 250                 255

Val Asp Val Cys Gly Met Phe Thr Asn Arg Ser Gly Ser Gln Gln Trp
                            260                 265                 270

Arg Gly Leu Ser Arg Tyr Phe Lys Val Gln Leu Arg Lys Arg Arg Val
                    275                 280                 285

Lys Asn Pro Tyr Pro Ile Ser Phe Leu Leu Thr Asp Leu Ile Asn Arg
                    290                 295                 300

Arg Thr Pro Arg Val Asp Gly Gln Pro Met Tyr Gly Met Asp Ala Gln
        305                 310                 315                 320

Val Glu Glu Val Arg Val Phe Glu Gly Thr Glu Glu Leu Pro Gly Asp
                            325                 330                 335

Pro Asp Met Met Arg Tyr Val Asp Lys Tyr Gly Gln Leu Gln Thr Lys
                    340                 345                 350

Met Leu

<210> SEQ ID NO 86
<211> LENGTH: 265
<212> TYPE: PRT
<213> ORGANISM: BK virus
<220> FEATURE:
<221> NAME/KEY: misc_feature
<223> OTHER INFORMATION: VP-1 protein fragment of serotype Ib having the
      sequence SEQ ID NO: 4

<400> SEQUENCE: 86

Glu Val Leu Glu Val Lys Thr Gly Val Asp Ala Ile Thr Glu Val Glu
        1               5                   10                  15

Cys Phe Leu Asn Pro Glu Met Gly Asp Pro Asn Glu Asn Leu Arg Gly
                            20                  25                  30

Phe Ser Leu Lys Leu Ser Ala Glu Asn Asp Phe Ser Ser Asp Ser Pro
                    35                  40                  45

Glu Arg Lys Met Leu Pro Cys Tyr Ser Thr Ala Arg Ile Pro Leu Pro
        50                  55                  60
```

```
Asn Leu Asn Glu Asp Leu Thr Cys Gly Asn Leu Leu Met Trp Glu Ala
 65                  70                  75                  80

Val Thr Val Gln Thr Glu Val Ile Gly Ile Thr Ser Met Leu Asn Leu
                 85                  90                  95

His Ala Gly Ser Gln Lys Val His Glu His Gly Gly Gly Lys Pro Ile
            100                 105                 110

Gln Gly Ser Asn Phe His Phe Phe Ala Val Gly Gly Asp Pro Leu Glu
        115                 120                 125

Met Gln Gly Val Leu Met Asn Tyr Arg Thr Lys Tyr Pro Glu Gly Thr
    130                 135                 140

Ile Thr Pro Lys Asn Pro Thr Ala Gln Ser Gln Val Met Asn Thr Asp
145                 150                 155                 160

His Lys Ala Tyr Leu Asp Lys Asn Asn Ala Tyr Pro Val Glu Cys Trp
                165                 170                 175

Ile Pro Asp Pro Ser Arg Asn Glu Asn Thr Arg Tyr Phe Gly Thr Phe
            180                 185                 190

Thr Gly Gly Glu Asn Val Pro Pro Val Leu His Val Thr Asn Thr Ala
        195                 200                 205

Thr Thr Val Leu Leu Asp Glu Gln Gly Val Gly Pro Leu Cys Lys Ala
    210                 215                 220

Asp Ser Leu Tyr Val Ser Ala Ala Asp Ile Cys Gly Leu Phe Thr Asn
225                 230                 235                 240

Ser Ser Gly Thr Gln Gln Trp Arg Gly Leu Ala Arg Tyr Phe Lys Ile
                245                 250                 255

Arg Leu Arg Lys Arg Ser Val Lys Asn
            260                 265

<210> SEQ ID NO 87
<211> LENGTH: 265
<212> TYPE: PRT
<213> ORGANISM: BK virus
<220> FEATURE:
<221> NAME/KEY: misc_feature
<223> OTHER INFORMATION: VP-1 protein fragment of serotype II having the
      sequence SEQ ID NO : 6

<400> SEQUENCE: 87

Glu Val Leu Glu Val Lys Thr Gly Val Asp Ala Ile Thr Glu Val Glu
1               5                   10                  15

Cys Phe Leu Asn Pro Glu Met Gly Asp Pro Asp Asn Leu Arg Gly
                20                  25                  30

Tyr Ser Leu Lys Leu Thr Ala Glu Asn Ala Phe Asp Ser Asp Ser Pro
            35                  40                  45

Asp Lys Lys Met Leu Pro Cys Tyr Ser Thr Ala Arg Ile Pro Leu Pro
 50                  55                  60

Asn Leu Asn Glu Asp Leu Thr Cys Gly Asn Leu Leu Met Trp Glu Ala
 65                  70                  75                  80

Val Thr Val Lys Thr Glu Val Ile Gly Ile Thr Ser Met Leu Asn Leu
                 85                  90                  95

His Ala Gly Ser Gln Lys Val His Glu Asn Gly Gly Gly Lys Pro Val
            100                 105                 110

Gln Gly Ser Asn Phe His Phe Phe Ala Val Gly Gly Asp Pro Leu Glu
        115                 120                 125

Met Gln Gly Val Leu Met Asn Tyr Arg Thr Lys Tyr Pro Gln Gly Thr
    130                 135                 140

Ile Thr Pro Lys Asn Pro Thr Ala Gln Ser Gln Val Met Asn Thr Asp
```

```
                145                 150                 155                 160
His Lys Ala Tyr Leu Asp Lys Asn Asn Ala Tyr Pro Val Glu Cys Trp
                    165                 170                 175

Ile Pro Asp Pro Ser Arg Asn Glu Asn Thr Arg Tyr Phe Gly Thr Tyr
                    180                 185                 190

Thr Gly Gly Glu Asn Val Pro Pro Val Leu His Val Thr Asn Thr Ala
                    195                 200                 205

Thr Thr Val Leu Leu Asp Glu Gln Gly Val Gly Pro Leu Cys Lys Ala
                    210                 215                 220

Asp Ser Leu Tyr Val Ser Ala Ala Asp Ile Cys Gly Leu Phe Thr Asn
225                 230                 235                 240

Ser Ser Gly Thr Gln Gln Trp Arg Gly Leu Ala Arg Tyr Phe Lys Ile
                    245                 250                 255

Arg Leu Arg Lys Arg Ser Val Lys Asn
                    260                 265

<210> SEQ ID NO 88
<211> LENGTH: 265
<212> TYPE: PRT
<213> ORGANISM: BK virus
<220> FEATURE:
<221> NAME/KEY: misc_feature
<223> OTHER INFORMATION: VP-1 protein fragment of serotype III having
      the sequence SEQ ID NO : 8

<400> SEQUENCE: 88

Glu Val Leu Glu Val Lys Thr Gly Val Asp Ala Ile Thr Glu Val Glu
1                   5                   10                  15

Cys Phe Leu Asn Pro Glu Met Gly Asp Pro Asp His Leu Arg Gly
                    20                  25                  30

Tyr Ser Gln His Leu Thr Ala Glu Asn Ala Phe Asp Ser Asp Ser Pro
                    35                  40                  45

Asp Lys Lys Met Leu Pro Cys Tyr Ser Thr Ala Arg Ile Pro Leu Pro
50                  55                  60

Asn Leu Asn Glu Asp Leu Thr Cys Gly Asn Leu Leu Met Trp Glu Ala
65                  70                  75                  80

Val Thr Val Lys Thr Glu Val Ile Gly Ile Thr Ser Met Leu Asn Leu
                    85                  90                  95

His Ala Gly Ser Gln Lys Val His Glu Asn Gly Gly Gly Lys Pro Val
                    100                 105                 110

Gln Gly Ser Asn Phe His Phe Phe Ala Val Gly Gly Asp Pro Leu Glu
                    115                 120                 125

Met Gln Gly Val Leu Met Asn Tyr Arg Thr Lys Tyr Pro Gln Gly Thr
                    130                 135                 140

Ile Thr Pro Lys Asn Pro Thr Ala Gln Ser Gln Val Met Asn Thr Asp
145                 150                 155                 160

His Lys Ala Tyr Leu Asp Lys Asn Asn Ala Tyr Pro Val Glu Cys Trp
                    165                 170                 175

Ile Pro Asp Pro Ser Lys Asn Glu Asn Thr Arg Tyr Phe Gly Thr Tyr
                    180                 185                 190

Thr Gly Gly Glu Asn Val Pro Pro Val Leu His Val Thr Asn Thr Ala
                    195                 200                 205

Thr Thr Val Leu Leu Asp Glu Gln Gly Val Gly Pro Leu Cys Lys Ala
                    210                 215                 220

Asp Ser Leu Tyr Val Ser Ala Ala Asp Ile Cys Gly Leu Phe Thr Asn
225                 230                 235                 240
```

-continued

Ser Ser Gly Thr Gln Gln Trp Arg Gly Leu Ala Arg Tyr Phe Lys Ile
            245                 250                 255

Arg Leu Arg Lys Arg Ser Val Lys Asn
            260                 265

<210> SEQ ID NO 89
<211> LENGTH: 265
<212> TYPE: PRT
<213> ORGANISM: BK virus
<220> FEATURE:
<221> NAME/KEY: misc_feature
<223> OTHER INFORMATION: VP-1 protein fragment of serotype IV having the
      sequence SEQ ID NO : 10

<400> SEQUENCE: 89

Glu Val Leu Glu Val Lys Thr Gly Leu Asp Ala Ile Thr Glu Val Glu
1               5                   10                  15

Cys Phe Leu Asn Pro Glu Met Gly Asp Pro Asp Asn Asp Leu Arg Gly
            20                  25                  30

Tyr Ser Leu Arg Leu Thr Ala Glu Thr Ala Phe Glu Ser Asp Ser Pro
        35                  40                  45

Asp Arg Lys Met Leu Pro Cys Tyr Ser Thr Ala Arg Ile Pro Leu Pro
50                  55                  60

Asn Leu Asn Glu Asp Leu Thr Cys Gly Ser Leu Leu Met Trp Glu Ala
65                  70                  75                  80

Val Thr Val Lys Thr Glu Val Ile Gly Ile Thr Ser Met Leu Asn Leu
                85                  90                  95

His Ala Gly Ser Gln Lys Val His Glu Asn Gly Gly Lys Pro Ile
            100                 105                 110

Gln Gly Ser Asn Phe His Phe Phe Ala Val Gly Gly Asp Pro Leu Glu
        115                 120                 125

Met Gln Gly Val Leu Met Asn Tyr Arg Thr Lys Tyr Pro Glu Gly Thr
130                 135                 140

Val Thr Pro Lys Asn Pro Thr Ala Gln Ser Gln Val Met Asn Thr Asp
145                 150                 155                 160

His Lys Ala Tyr Leu Asp Lys Asn Asn Ala Tyr Pro Val Glu Cys Trp
                165                 170                 175

Ile Pro Asp Pro Ser Arg Asn Glu Asn Thr Arg Tyr Phe Gly Thr Tyr
            180                 185                 190

Thr Gly Gly Glu Asn Val Pro Pro Val Leu His Val Thr Asn Thr Ala
        195                 200                 205

Thr Thr Val Leu Leu Asp Glu Gln Gly Val Gly Pro Leu Cys Lys Ala
        210                 215                 220

Asp Ser Leu Tyr Val Ser Ala Ala Asp Ile Cys Gly Leu Phe Thr Asn
225                 230                 235                 240

Ser Ser Gly Thr Gln Gln Trp Arg Gly Leu Pro Arg Tyr Phe Lys Ile
            245                 250                 255

Arg Leu Arg Lys Arg Ser Val Lys Asn
            260                 265

<210> SEQ ID NO 90
<211> LENGTH: 1089
<212> TYPE: DNA
<213> ORGANISM: BK virus
<220> FEATURE:
<221> NAME/KEY: CDS
<222> LOCATION: (1)..(1089)
<223> OTHER INFORMATION: VP-1 gene, serotype Ib2

-continued

```
<400> SEQUENCE: 90 atg gca ccc aca aag cgc aag ggc gaa tgc ccc ggc gcc gcc cca aag      48
Met Ala Pro Thr Lys Arg Lys Gly Glu Cys Pro Gly Ala Ala Pro Lys
1               5                   10                  15 aaa ccc aag gag cca gtc cag gtc ccc aag ttg ctg atc aag ggc ggc      96
Lys Pro Lys Glu Pro Val Gln Val Pro Lys Leu Leu Ile Lys Gly Gly
                20                  25                  30 gtg gag gtc ctg gag gtc aag acc ggc ctg gac gcc atc acc gag gtg     144
Val Glu Val Leu Glu Val Lys Thr Gly Leu Asp Ala Ile Thr Glu Val
            35                  40                  45 gag tgt ttc ttg aac ccc gag atg ggc gac ccc gac gag aac ctg cgc     192
Glu Cys Phe Leu Asn Pro Glu Met Gly Asp Pro Asp Glu Asn Leu Arg
        50                  55                  60 ggg ttc agc ttg aag ctg agc gct gag aac gac ttc agc tcc gac tca     240
Gly Phe Ser Leu Lys Leu Ser Ala Glu Asn Asp Phe Ser Ser Asp Ser
65                  70                  75                  80 ccc gac cgc aag atg ttg cca tgc tat tcc acc gcc cgc atc cca ctg     288
Pro Asp Arg Lys Met Leu Pro Cys Tyr Ser Thr Ala Arg Ile Pro Leu
                85                  90                  95 ccc aac ctc aac gaa gac ttg aca tgc ggc aac ctg ctg atg tgg gaa     336
Pro Asn Leu Asn Glu Asp Leu Thr Cys Gly Asn Leu Leu Met Trp Glu
                100                 105                 110 gcc gtc acc gtg cag acc gaa gtc atc ggc atc acc tcc atg ttg aat     384
Ala Val Thr Val Gln Thr Glu Val Ile Gly Ile Thr Ser Met Leu Asn
            115                 120                 125 ctg cac gcc gga agc caa aag gtg cac gag cac ggc ggc ggg aag ccc     432
Leu His Ala Gly Ser Gln Lys Val His Glu His Gly Gly Gly Lys Pro
        130                 135                 140 atc cag ggg tca aac ttc cat ttc ttc gcc gtc ggc ggc gat cca ctc     480
Ile Gln Gly Ser Asn Phe His Phe Phe Ala Val Gly Gly Asp Pro Leu
145                 150                 155                 160 gag atg caa ggc gtg ttg atg aac tat cgc acc aag tat ccc gaa ggc     528
Glu Met Gln Gly Val Leu Met Asn Tyr Arg Thr Lys Tyr Pro Glu Gly
                165                 170                 175 acc atc aca ccc aag aac cca acc gcc caa agt cag gtc atg aac acc     576
Thr Ile Thr Pro Lys Asn Pro Thr Ala Gln Ser Gln Val Met Asn Thr
                180                 185                 190 gat cac aaa gca tat ctc gat aag aat aac gcc tac ccc gtc gag tgt     624
Asp His Lys Ala Tyr Leu Asp Lys Asn Asn Ala Tyr Pro Val Glu Cys
            195                 200                 205 tgg atc ccc gat cca tcc cgg aac gag aac acc cgc tac ttc ggc acc     672
Trp Ile Pro Asp Pro Ser Arg Asn Glu Asn Thr Arg Tyr Phe Gly Thr
        210                 215                 220 ttt acc ggc ggc gag aac gtc cca ccc gtg ttg cac gtg aca aat acc     720
Phe Thr Gly Gly Glu Asn Val Pro Pro Val Leu His Val Thr Asn Thr
225                 230                 235                 240 gcc aca acc gtc ctg ctc gac gag caa ggc gtc ggc cca ctc tgc aag     768
Ala Thr Thr Val Leu Leu Asp Glu Gln Gly Val Gly Pro Leu Cys Lys
                245                 250                 255 gca gac agc ctc tac gtc agc gcc gcc gac atc tgc gga ctg ttc acc     816
Ala Asp Ser Leu Tyr Val Ser Ala Ala Asp Ile Cys Gly Leu Phe Thr
                260                 265                 270 aat tca agc ggc acc cag caa tgg cgc ggg ttg gcc cgc tac ttc aaa     864
Asn Ser Ser Gly Thr Gln Gln Trp Arg Gly Leu Ala Arg Tyr Phe Lys
            275                 280                 285 atc agg ctc cgc aag cgc agc gtg aag aat ccc tat cca atc agt ttc     912
Ile Arg Leu Arg Lys Arg Ser Val Lys Asn Pro Tyr Pro Ile Ser Phe
        290                 295                 300
```

-continued

| | | | | | | | | | | | | | | |
|---|---|---|---|---|---|---|---|---|---|---|---|---|---|---|
| ctg | ctg | tcc | gat | ttg | atc | aat | cgc | cgc | aca | caa | cgc | gtc | gac | ggc | cag | 960 |
| Leu | Leu | Ser | Asp | Leu | Ile | Asn | Arg | Arg | Thr | Gln | Arg | Val | Asp | Gly | Gln | |
| 305 | | | | 310 | | | | | 315 | | | | | 320 | | |

| | | | | | | | | | | | | | | |
|---|---|---|---|---|---|---|---|---|---|---|---|---|---|---|
| ccc | atg | tac | ggc | atg | gaa | agc | caa | gtc | gaa | gaa | gtg | cgc | gtc | ttc | gac | 1008 |
| Pro | Met | Tyr | Gly | Met | Glu | Ser | Gln | Val | Glu | Glu | Val | Arg | Val | Phe | Asp | |
| | | | | 325 | | | | | 330 | | | | | 335 | | |

| | | | | | | | | | | | | | | |
|---|---|---|---|---|---|---|---|---|---|---|---|---|---|---|
| ggg | acc | gag | cgg | ttg | ccc | ggc | gat | ccc | gac | atg | atc | cgc | tac | atc | gat | 1056 |
| Gly | Thr | Glu | Arg | Leu | Pro | Gly | Asp | Pro | Asp | Met | Ile | Arg | Tyr | Ile | Asp | |
| | | | 340 | | | | | 345 | | | | | 350 | | | |

| | | | | | | | | | |
|---|---|---|---|---|---|---|---|---|---|
| aag | caa | ggc | cag | ctc | caa | acc | aag | atg | ctg | tga | 1089 |
| Lys | Gln | Gly | Gln | Leu | Gln | Thr | Lys | Met | Leu | | |
| | | 355 | | | | | 360 | | | | |

<210> SEQ ID NO 91
<211> LENGTH: 362
<212> TYPE: PRT
<213> ORGANISM: BK virus

<400> SEQUENCE: 91

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe

```
            290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Val Arg Val Phe Asp
                325                 330                 335

Gly Thr Glu Arg Leu Pro Gly Asp Pro Asp Met Ile Arg Tyr Ile Asp
                340                 345                 350

Lys Gln Gly Gln Leu Gln Thr Lys Met Leu
            355                 360

<210> SEQ ID NO 92
<211> LENGTH: 362
<212> TYPE: PRT
<213> ORGANISM: BK virus
<220> FEATURE:
<221> NAME/KEY: misc_feature
<223> OTHER INFORMATION: VP-1 protein of sirotype Ib2, R93E mutant

<400> SEQUENCE: 92

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
                20                  25                  30

Val Glu Val Leu Glu Val Lys Thr Gly Leu Asp Ala Ile Thr Glu Val
                35                  40                  45

Glu Cys Phe Le

```
Ile Arg Leu Arg Lys Arg Ser Val Lys Asn Pro Tyr Pro Ile Ser Phe
        290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
                340                 345                 350

Lys Gln Gly Gln Leu Gln Thr Lys Met Leu
                355                 360

<210> SEQ ID NO 93
<211> LENGTH: 362
<212> TYPE: PRT
<213> ORGANISM: BK virus
<220> FEATURE:
<221> NAME/KEY: misc_feature
<223> OTHER INFORMATION: VP-1 protein of serotype Ib2, T192A D193K
      mutant

<400> SEQUENCE: 93

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
                20                  25                  30

Val Glu Val Leu Gl

```
                    275                 280                 285
Ile Arg Leu Arg Lys Arg Ser Val Lys Asn Pro Tyr Pro Ile Ser Phe
        290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
            355                 360

<210> SEQ ID NO 94
<211> LENGTH: 362
<212> TYPE: PRT
<213> ORGANISM: BK virus
<220> FEATURE:
<221> NAME/KEY: misc_feature
<223> OTHER INFORMATION: VP-1 protein of serotype Ib2, D199N K200N N201A
      N202A mutant

<400> SEQUENCE: 94

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asn Asn Ala Ala Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270
```

```
Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
                340                 345                 350

Lys Gln Gly Gln Leu Gln Thr Lys Met Leu
                355                 360

<210> SEQ ID NO 95
<211> LENGTH: 357
<212> TYPE: PRT
<213> ORGANISM: BK virus
<220> FEATURE:
<221> NAME/KEY: misc_feature
<223> OTHER INFORMATION: VP-1 protein of serotype Ib2, E73_S77del mutant

<400> SEQUENCE: 95

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
                20                  25                  30

Val Glu Val Leu Glu Val L

```
                      260                 265                 270
Gln Gln Trp Arg Gly Leu Ala Arg Tyr Phe Lys Ile Arg Leu Arg Lys
            275                 280                 285

Arg Ser Val Lys Asn Pro Tyr Pro Ile Ser Phe Leu Leu Ser Asp Leu
            290                 295                 300

Ile Asn Arg Arg Thr Gln Arg Val Asp Gly Gln Pro Met Tyr Gly Met
305                 310                 315                 320

Glu Ser Gln Val Glu Glu Val Arg Val Phe Asp Gly Thr Glu Arg Leu
                325                 330                 335

Pro Gly Asp Pro Asp Met Ile Arg Tyr Ile Asp Lys Gln Gly Gln Leu
            340                 345                 350

Gln Thr Lys Met Leu
            355

<210> SEQ ID NO 96
<211> LENGTH: 350
<212> TYPE: PRT
<213> ORGANISM: BK virus
<220> FEATURE:
<221> NAME/KEY: misc_feature
<223> OTHER INFORMATION: VP-1 protein of serotype Ib2, S71_D82del mutant

<400> SEQUENCE: 96

Met Ala Pro Thr Lys Arg Lys Gly Glu Cys Pro Gly Ala Ala Pro Lys
1               5                   10                  15

Lys Pro L

```
Gly Leu Phe Thr Asn Ser Ser Gly Thr Gln Gln Trp Arg Gly Leu Ala
            260                 265                 270

Arg Tyr Phe Lys Ile Arg Leu Arg Lys Arg Ser Val Lys Asn Pro Tyr
        275                 280                 285

Pro Ile Ser Phe Leu Leu Ser Asp Leu Ile Asn Arg Arg Thr Gln Arg
    290                 295                 300

Val Asp Gly Gln Pro Met Tyr Gly Met Glu Ser Gln Val Glu Glu Val
305                 310                 315                 320

Arg Val Phe Asp Gly Thr Glu Arg Leu Pro Gly Asp Pro Asp Met Ile
                325                 330                 335

Arg Tyr Ile Asp Lys Gln Gly Gln Leu Gln Thr Lys Met Leu
            340                 345                 350

<210> SEQ ID NO 97
<211> LENGTH: 362
<212> TYPE: PRT
<213> ORGANISM: BK virus
<220> FEATURE:
<221> NAME/KEY: misc_feature
<223> OTHER INFORMATION: VP-1 protein of serotype Ib2, K135A E138A H139A
      mutant

<400> SEQUENCE: 97

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val L

```
                    260                 265                 270
Asn Ser Ser Gly Thr Gln Gln Trp Arg Gly Leu Ala Arg Tyr Phe Lys
            275                 280                 285

Ile Arg Leu Arg Lys Arg Ser Val Lys Asn Pro Tyr Pro Ile Ser Phe
        290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
                340                 345                 350

Lys Gln Gly Gln Leu Gln Thr Lys Met Leu
            355                 360

<210> SEQ ID NO 98
<211> LENGTH: 357
<212> TYPE: PRT
<213> ORGANISM: BK virus
<220> FEATURE:
<221> NAME/KEY: misc_feature
<223> OTHER INFORMATION: VP-1 protein of serotype Ib2, K135_H139del
      mutant

<400> SEQUENCE: 98

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Gl

```
Val Ser Ala Ala Asp Ile Cys Gly Leu Phe Thr Asn Ser Ser Gly Thr
            260                 265                 270

Gln Gln Trp Arg Gly Leu Ala Arg Tyr Phe Lys Ile Arg Leu Arg Lys
        275                 280                 285

Arg Ser Val Lys Asn Pro Tyr Pro Ile Ser Phe Leu Leu Ser Asp Leu
    290                 295                 300

Ile Asn Arg Arg Thr Gln Arg Val Asp Gly Gln Pro Met Tyr Gly Met
305                 310                 315                 320

Glu Ser Gln Val Glu Val Arg Val Phe Asp Gly Thr Glu Arg Leu
                325                 330                 335

Pro Gly Asp Pro Asp Met Ile Arg Tyr Ile Asp Lys Gln Gly Gln Leu
            340                 345                 350

Gln Thr Lys Met Leu
        355

<210> SEQ ID NO 99
<211> LENGTH: 362
<212> TYPE: PRT
<213> ORGANISM: BK virus
<220> FEATURE:
<221> NAME/KEY: misc_feature
<223> OTHER INFORMATION: VP-1 protein of serotype Ib2, S274A S275A
      mutant

<400> SEQUENCE: 99

Met Ala Pro Thr Lys Arg Lys Gly Glu Cys Pro Gly Ala Ala Pro Lys
1               5                   10                  15

Lys Pro Lys Glu Pro Val Gln Val Pro L

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ala Ala Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360

<210> SEQ ID NO 100
<211> LENGTH: 358
<212> TYPE: PRT
<213> ORGANISM: BK virus
<220> FEATURE:
<221> NAME/KEY: misc_feature
<223> OTHER INFORMATION: VP-1 protein of serotype Ib2, S274_T277del
      mutant

<400> SEQUENCE: 100

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr

```
                225                 230                 235                 240
Ala Thr Thr Val Leu Leu Asp Glu Gln Gly Val Gly Pro Leu Cys Lys
                    245                 250                 255

Ala Asp Ser Leu Tyr Val Ser Ala Ala Asp Ile Cys Gly Leu Phe Thr
                260                 265                 270

Asn Gln Gln Trp Arg Gly Leu Ala Arg Tyr Phe Lys Ile Arg Leu Arg
                275                 280                 285

Lys Arg Ser Val Lys Asn Pro Tyr Pro Ile Ser Phe Leu Leu Ser Asp
            290                 295                 300

Leu Ile Asn Arg Arg Thr Gln Arg Val Asp Gly Gln Pro Met Tyr Gly
305                 310                 315                 320

Met Glu Ser Gln Val Glu Val Arg Val Phe Asp Gly Thr Glu Arg
                325                 330                 335

Leu Pro Gly Asp Pro Asp Met Ile Arg Tyr Ile Asp Lys Gln Gly Gln
                340                 345                 350

Leu Gln Thr Lys Met Leu
            355

<210> SEQ ID NO 101
<211> LENGTH: 362
<212> TYPE: PRT
<213> ORGANISM: BK virus
<220> FEATURE:
<221> NAME/KEY: misc_feature
<223> OTHER INFORMATION: VP-1 protein of serotype Ib2, R83A K84A mutant

<400> SEQUENCE: 101

Met Ala Pro Thr Lys Arg Lys Gly Glu C

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
            245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
            325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
            355                 360

<210> SEQ ID NO 102
<211> LENGTH: 358
<212> TYPE: PRT
<213> ORGANISM: BK virus
<220> FEATURE:
<221> NAME/KEY: misc_feature
<223> OTHER INFORMATION: VP-1 protein of serotype Ib2, R83_L86del mutant

<400> SEQUENCE: 102

Met Ala Pro Thr Lys Arg L

```
Glu Asn Val Pro Pro Val Leu His Val Thr Asn Thr Ala Thr Thr Val
225                 230                 235                 240

Leu Leu Asp Glu Gln Gly Val Gly Pro Leu Cys Lys Ala Asp Ser Leu
            245                 250                 255

Tyr Val Ser Ala Ala Asp Ile Cys Gly Leu Phe Thr Asn Ser Ser Gly
            260                 265                 270

Thr Gln Gln Trp Arg Gly Leu Ala Arg Tyr Phe Lys Ile Arg Leu Arg
        275                 280                 285

Lys Arg Ser Val Lys Asn Pro Tyr Pro Ile Ser Phe Leu Leu Ser Asp
    290                 295                 300

Leu Ile Asn Arg Arg Thr Gln Arg Val Asp Gly Gln Pro Met Tyr Gly
305                 310                 315                 320

Met Glu Ser Gln Val Glu Glu Val Arg Val Phe Asp Gly Thr Glu Arg
            325                 330                 335

Leu Pro Gly Asp Pro Asp Met Ile Arg Tyr Ile Asp Lys Gln Gly Gln
            340                 345                 350

Leu Gln Thr Lys Met Leu
            355
```